US012583918B2

(12) United States Patent
Honda et al.

(10) Patent No.: US 12,583,918 B2
(45) Date of Patent: Mar. 24, 2026

(54) THERAPEUTIC AGENT FOR UROLOGICAL CANCER WHICH IS CHARACTERIZED BY BEING ADMINISTERED WITH IL-6 INHIBITOR AND CCR2 INHIBITOR IN COMBINATION

(71) Applicants: HIROSHIMA UNIVERSITY, Hiroshima (JP); TOKYO WOMEN'S MEDICAL UNIVERSITY, Tokyo (JP); CHUGAI SEIYAKU KABUSHIKI KAISHA, Tokyo (JP)

(72) Inventors: Hiroaki Honda, Tokyo (JP); Kohei Kobatake, Hiroshima (JP)

(73) Assignees: Tokyo Women's Medical University, Tokyo (JP); Hiroshima University, Hiroshima (JP); Chugai Seiyaku Kabushiki Kaisha, Tokyo (JP)

( * ) Notice: Subject to any disclaimer, the term of this patent is extended or adjusted under 35 U.S.C. 154(b) by 1000 days.

(21) Appl. No.: 17/601,831

(22) PCT Filed: Apr. 16, 2020

(86) PCT No.: PCT/JP2020/016652
§ 371 (c)(1),
(2) Date: Oct. 6, 2021

(87) PCT Pub. No.: WO2020/213665
PCT Pub. Date: Oct. 22, 2020

(65) Prior Publication Data
US 2022/0204608 A1     Jun. 30, 2022

(30) Foreign Application Priority Data
Apr. 17, 2019     (JP) ................................. 2019-078928

(51) Int. Cl.
*C07K 16/24* (2006.01)
*A61K 31/28* (2006.01)
*A61K 31/80* (2006.01)
*A61K 39/00* (2006.01)
*A61K 39/395* (2006.01)
*A61K 45/06* (2006.01)
*A61P 13/00* (2006.01)
*A61P 13/10* (2006.01)
*A61P 35/00* (2006.01)
*C07K 16/28* (2006.01)
*A61P 13/08* (2006.01)
*A61P 13/12* (2006.01)

(52) U.S. Cl.
CPC ............ *C07K 16/248* (2013.01); *A61K 31/80* (2013.01); *A61K 39/3955* (2013.01); *A61P 35/00* (2018.01); *C07K 16/24* (2013.01); *C07K 16/2866* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,126,250 A | 6/1992 | McDonough et al. |
| 5,216,128 A | 6/1993 | Novick et al. |
| 5,530,101 A | 6/1996 | Queen et al. |
| 5,621,077 A | 4/1997 | Novick et al. |
| 5,639,455 A | 6/1997 | Shimamura et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,856,135 A | 1/1999 | Tsuchiya et al. |
| 5,888,510 A | 3/1999 | Kishimoto et al. |
| 6,074,643 A | 6/2000 | Barbera-Guillem |
| 6,121,423 A | 9/2000 | Tsuchiya et al. |
| 6,261,560 B1 | 7/2001 | Tsujinaka et al. |
| 6,309,636 B1 | 10/2001 | Do Couto |
| 6,552,083 B1 | 4/2003 | Isobe et al. |
| 6,723,319 B1 | 4/2004 | Ito et al. |
| 8,470,316 B2 | 6/2013 | Yasunami |
| 8,562,991 B2 | 10/2013 | Igawa et al. |
| 8,623,355 B2 | 1/2014 | Okada et al. |
| 8,771,686 B2 | 7/2014 | Ishida |
| 8,945,558 B2 | 2/2015 | Kobara |
| 9,017,677 B2 | 4/2015 | Mihara |
| 9,260,516 B2 | 2/2016 | Nishimoto et al. |
| 9,539,322 B2 | 1/2017 | Nishimura |
| 9,725,514 B2 | 8/2017 | Takahashi et al. |

(Continued)

FOREIGN PATENT DOCUMENTS

| | | |
|---|---|---|
| AR | 068564 | 11/2009 |
| CA | 1 332 367 | 10/1994 |

(Continued)

OTHER PUBLICATIONS

Kovaleva "Tumor Associated Macrophages in Kidney Cancer". Analytical Cellular Pathology vol. 2016, Article ID 9307549, 6 pages. (Year: 2016).*
Chen, Miao-Fen et al. "IL-6 expression regulates tumorigenicity and correlates with prognosis in bladder cancer." PloS one vol. 8,4 e61901. Apr. 30, 2013, doi:10.1371/journal.pone.0061901 (Year: 2013).*
O'Connor, Tracy et al. "CCL2-CCR2 Signaling in Disease Pathogenesis." Endocrine, metabolic & immune disorders drug targets vol. 15,2 (2015): 105-18. (Year: 2015).*
Kobatake, Kohei; Ikeda, Ken ichiro; Nakata, Yuichiro; Sera, Yasuyuki; Hayashi, Tetsutaro; et al. Cancer Science, suppl. 1109: 167. Wiley. (Jan. 2018). Abstract. (Year: 2018).*

(Continued)

*Primary Examiner* — Juliet C Switzer
*Assistant Examiner* — Katherine Ann Holtzman
(74) *Attorney, Agent, or Firm* — Fish & Richardson P.C.

(57) ABSTRACT

Therapeutic agents and treatment methods for urologic cancers, particularly urologic cancers with reduced lysine (K)-specific demethylase 6A (KDM6A) function, the agents and methods being characterized by suppressing both IL-6 activity and CCR2/CCL2 activity, are provided.

13 Claims, 3 Drawing Sheets

(56) References Cited

U.S. PATENT DOCUMENTS

| | | |
|---|---|---|
| 10,662,245 B2 | 5/2020 | Igawa et al. |
| 10,697,883 B2 | 6/2020 | Yamamura et al. |
| 10,717,781 B2 | 7/2020 | Mitsunaga et al. |
| 10,774,148 B2 | 9/2020 | Kakehi et al. |
| 10,782,290 B2 | 9/2020 | Yamamura et al. |
| 11,692,037 B2 | 7/2023 | Fujimoto et al. |
| 11,851,486 B2 | 12/2023 | Matsuoka et al. |
| 2001/0001663 A1 | 5/2001 | Kishimoto et al. |
| 2002/0119150 A1 | 8/2002 | Kirk et al. |
| 2002/0187150 A1 | 12/2002 | Mihara et al. |
| 2004/0018540 A1 | 1/2004 | Yamamura et al. |
| 2004/0028681 A1 | 2/2004 | Ito et al. |
| 2004/0071706 A1 | 4/2004 | Kishimoto et al. |
| 2004/0170626 A1 | 9/2004 | Schuurman et al. |
| 2005/0096257 A1 | 5/2005 | Shima et al. |
| 2005/0142635 A1 | 6/2005 | Tsuchiya et al. |
| 2005/0158317 A1 | 7/2005 | Blay et al. |
| 2005/0182007 A1 | 8/2005 | McSwiggen et al. |
| 2005/0261229 A1 | 11/2005 | Gillies et al. |
| 2005/0272634 A1 | 12/2005 | Bahlmann et al. |
| 2006/0039902 A1 | 2/2006 | Young et al. |
| 2006/0111316 A1 | 5/2006 | Lawless et al. |
| 2006/0134113 A1 | 6/2006 | Mihara |
| 2006/0165696 A1 | 7/2006 | Okano et al. |
| 2006/0188502 A1 | 8/2006 | Giles-Komar et al. |
| 2006/0193772 A1 | 8/2006 | Ochiai et al. |
| 2006/0251653 A1 | 11/2006 | Okuda et al. |
| 2006/0292147 A1 | 12/2006 | Yoshizaki et al. |
| 2007/0036785 A1 | 2/2007 | Kishimoto et al. |
| 2007/0134242 A1 | 6/2007 | Nishimoto et al. |
| 2007/0167425 A1 | 7/2007 | Nakade et al. |
| 2007/0280945 A1 | 12/2007 | Stevens et al. |
| 2008/0032923 A1 | 2/2008 | Kudou et al. |
| 2008/0081041 A1 | 4/2008 | Nemeth et al. |
| 2009/0022719 A1 | 1/2009 | Mihara et al. |
| 2009/0022726 A1 | 1/2009 | Zaki et al. |
| 2009/0028784 A1 | 1/2009 | Garcia-Martinez et al. |
| 2009/0269335 A1 | 10/2009 | Nakashima et al. |
| 2009/0291076 A1 | 11/2009 | Morichika et al. |
| 2010/0061986 A1 | 3/2010 | Takahashi |
| 2010/0129357 A1 | 5/2010 | Garcia-Martinez et al. |
| 2010/0247523 A1 | 9/2010 | Kano et al. |
| 2010/0298542 A1 | 11/2010 | Igawa et al. |
| 2010/0316636 A1 | 12/2010 | Radin et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga |
| 2011/0245473 A1 | 10/2011 | Igawa et al. |
| 2012/0045453 A1 | 2/2012 | Chen et al. |
| 2012/0183539 A1 | 7/2012 | Maeda |
| 2012/0225060 A1* | 9/2012 | Lee .......................... A61P 19/02 |
| | | 536/23.53 |
| 2012/0253016 A1 | 10/2012 | Igawa et al. |
| 2012/0301460 A1 | 11/2012 | Bao et al. |
| 2013/0202588 A1 | 8/2013 | Nishimura |
| 2013/0317203 A1 | 11/2013 | Igawa et al. |
| 2014/0342450 A1* | 11/2014 | Gladue ................... A61P 25/00 |
| | | 435/417 |
| 2015/0166666 A1 | 6/2015 | Igawa et al. |
| 2016/0022812 A1 | 1/2016 | Mitsunaga et al. |
| 2016/0139117 A1 | 5/2016 | Yamamura et al. |
| 2017/0121412 A1 | 5/2017 | Igawa et al. |
| 2017/0362304 A1 | 12/2017 | Fukuda et al. |
| 2018/0148509 A1 | 5/2018 | Kakehi et al. |
| 2018/0149573 A1 | 5/2018 | Yamamura et al. |
| 2018/0222986 A1 | 8/2018 | Maeda |
| 2019/0085085 A1 | 3/2019 | Igawa et al. |
| 2020/0148760 A1 | 5/2020 | Matsuoka et al. |
| 2020/0299391 A1 | 9/2020 | Fujimoto et al. |
| 2021/0017286 A1 | 1/2021 | Kakehi et al. |
| 2021/0206862 A1 | 7/2021 | Igawa et al. |
| 2021/0363238 A1 | 11/2021 | Kato |
| 2022/0041741 A1 | 2/2022 | Igawa et al. |
| 2022/0220210 A1 | 7/2022 | Takeshita et al. |
| 2022/0306755 A1 | 9/2022 | Igawa et al. |
| 2023/0159648 A1 | 5/2023 | Igawa et al. |
| 2024/0010738 A1 | 1/2024 | Igawa et al. |
| 2024/0043526 A1 | 2/2024 | Matsuoka et al. |
| 2024/0150477 A1 | 5/2024 | Kakehi et al. |
| 2024/0158518 A1 | 5/2024 | Ozawa et al. |
| 2024/0301075 A1 | 9/2024 | Igawa et al. |
| 2024/0417480 A1 | 12/2024 | Kakehi et al. |

FOREIGN PATENT DOCUMENTS

| | | |
|---|---|---|
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 648 644 | 10/2007 |
| CA | 2 700 394 | 4/2009 |
| CA | 2 700 498 | 4/2009 |
| CN | 1164194 A | 11/1997 |
| CN | 1297357 A | 5/2001 |
| CN | 1694894 A | 11/2005 |
| CN | 1849135 A | 10/2006 |
| CN | 101849006 | 9/2010 |
| CN | 102574918 | 7/2012 |
| CN | 101370525 B | 9/2013 |
| CN | 103476410 | 12/2013 |
| CN | 103476793 | 12/2013 |
| CN | 107224440 | 10/2017 |
| EP | 0 361 902 A | 4/1990 |
| EP | 0 628 639 A | 12/1994 |
| EP | 0 721 783 A1 | 7/1996 |
| EP | 0 783 893 A | 7/1997 |
| EP | 0 791 359 A | 8/1997 |
| EP | 0 811 384 A1 | 12/1997 |
| EP | 0 931 544 A2 | 7/1999 |
| EP | 0 983 767 A | 3/2000 |
| EP | 1 004 315 A | 5/2000 |
| EP | 1 074 268 A | 2/2001 |
| EP | 1 108 435 A1 | 6/2001 |
| EP | 1 197 210 A1 | 4/2002 |
| EP | 1 334 731 A | 8/2003 |
| EP | 1 374 900 A | 1/2004 |
| EP | 1 562 968 A0 | 8/2005 |
| EP | 1 690 550 A | 8/2006 |
| EP | 1 707 215 A | 10/2006 |
| EP | 1 728 801 A | 12/2006 |
| EP | 1 733 740 A | 12/2006 |
| EP | 1 941 907 A | 7/2008 |
| EP | 1 941 908 A | 7/2008 |
| EP | 1 967 207 A | 9/2008 |
| EP | 1 967 209 A | 9/2008 |
| EP | 1 990 060 A | 11/2008 |
| EP | 2 025 346 A1 | 2/2009 |
| EP | 2 123 302 A | 11/2009 |
| EP | 2 174 667 A | 4/2010 |
| EP | 2 194 066 A | 6/2010 |
| EP | 2 196 220 A | 6/2010 |
| EP | 2 202 245 A | 6/2010 |
| EP | 2 206 775 A | 7/2010 |
| EP | 2 275 443 A | 1/2011 |
| EP | 2 305 306 A | 4/2011 |
| EP | 2 330 193 A | 6/2011 |
| EP | 2 578 233 A | 4/2013 |
| EP | 2 639 305 A | 9/2013 |
| EP | 3 009 518 A1 | 4/2016 |
| EP | 3 483 283 A1 | 5/2019 |
| ES | 2276525 T | 6/2007 |
| FR | 2694767 A | 2/1994 |
| JP | H02-163096 | 6/1990 |
| JP | H06-505253 A | 6/1994 |
| JP | H06-237772 A | 8/1994 |
| JP | H07-046998 A | 2/1995 |
| JP | H08-208514 A | 8/1996 |
| JP | H11-89582 A | 4/1999 |
| JP | H11-180873 A | 7/1999 |
| JP | 3345419 B2 | 8/2002 |

(56) References Cited

FOREIGN PATENT DOCUMENTS

| JP | 2003-525243 A | 8/2003 |
|---|---|---|
| JP | 2004/028926 | 1/2004 |
| JP | 2005-524606 A | 8/2005 |
| JP | 2005-281235 A | 10/2005 |
| JP | 2006-503001 A | 1/2006 |
| JP | 2006-512325 A | 4/2006 |
| JP | 2006-524685 A | 11/2006 |
| JP | 2007-528691 A | 10/2007 |
| JP | 2008-037875 A | 2/2008 |
| JP | 2008-037876 A | 2/2008 |
| JP | 2008-538931 A | 11/2008 |
| JP | 2008-297315 A | 12/2008 |
| JP | 4468578 B2 | 5/2010 |
| JP | 2010-527615 A | 8/2010 |
| JP | 2012-500020 | 1/2012 |
| JP | 2013/541594 | 11/2013 |
| JP | 5530635 B2 | 6/2014 |
| KR | 2006/0010765 | 2/2006 |
| KR | 2007/0035482 | 3/2007 |
| RU | 2127117 C1 | 3/1999 |
| RU | 2147442 | 4/2000 |
| RU | 2195960 | 1/2003 |
| RU | 2430111 | 9/2011 |
| TW | 2008/038985 A | 1/2008 |
| TW | 2010/21829 | 6/2010 |
| TW | 2013/02219 | 1/2013 |
| WO | WO 92/12729 A1 | 8/1992 |
| WO | WO 92/19759 | 11/1992 |
| WO | WO 93/08817 A1 | 5/1993 |
| WO | WO 94/20488 A1 | 9/1994 |
| WO | WO 94/28159 A1 | 12/1994 |
| WO | WO 95/09873 A1 | 4/1995 |
| WO | WO 96/011020 | 4/1996 |
| WO | WO 96/12503 | 5/1996 |
| WO | WO 96/25174 A1 | 8/1996 |
| WO | WO 98/36061 A2 | 8/1998 |
| WO | WO 98/42377 | 10/1998 |
| WO | WO 99/08707 | 2/1999 |
| WO | WO 99/47170 | 9/1999 |
| WO | WO 99/58572 | 11/1999 |
| WO | WO 99/60013 A2 | 11/1999 |
| WO | WO 00/10607 A1 | 3/2000 |
| WO | WO 01/05394 A1 | 1/2001 |
| WO | WO 01/45678 A2 | 6/2001 |
| WO | WO 01/64214 A2 | 9/2001 |
| WO | WO 02/03492 A1 | 1/2002 |
| WO | WO 02/34292 | 5/2002 |
| WO | WO 02/080969 | 10/2002 |
| WO | WO 03/048205 A2 | 6/2003 |
| WO | WO 03/105861 A1 | 12/2003 |
| WO | WO 2004/007701 A1 | 1/2004 |
| WO | WO 2004/039826 A1 | 5/2004 |
| WO | WO 2004/045507 A2 | 6/2004 |
| WO | WO 2004/045512 A2 | 6/2004 |
| WO | WO 2004/045520 A2 | 6/2004 |
| WO | WO 2004/071404 A2 | 8/2004 |
| WO | WO 2004/073741 A1 | 9/2004 |
| WO | WO 2004/096273 | 11/2004 |
| WO | WO 2005/028514 A1 | 3/2005 |
| WO | WO 2005/037315 | 4/2005 |
| WO | WO 2005/044848 A1 | 5/2005 |
| WO | WO 2005/061000 | 7/2005 |
| WO | WO 2005/080429 | 9/2005 |
| WO | WO 2005/090405 | 9/2005 |
| WO | WO 2005/107800 A1 | 11/2005 |
| WO | WO 2006/009092 A1 | 1/2006 |
| WO | WO 2006/023144 | 3/2006 |
| WO | WO 2006/070286 | 7/2006 |
| WO | WO 2006/072954 A2 | 7/2006 |
| WO | WO 2006/119115 | 11/2006 |
| WO | WO 2007/024715 A2 | 3/2007 |
| WO | WO 2007/043641 | 4/2007 |
| WO | WO 2007/046489 | 4/2007 |
| WO | WO 2007/058194 | 5/2007 |
| WO | WO 2007/061029 | 5/2007 |
| WO | WO 2007/067976 A2 | 6/2007 |
| WO | WO 2007/074880 | 7/2007 |
| WO | WO 2007/076927 A1 | 7/2007 |
| WO | WO 2007/086490 | 8/2007 |
| WO | WO 2007/114319 | 10/2007 |
| WO | WO 2007/116962 | 10/2007 |
| WO | WO 2007/137984 | 12/2007 |
| WO | WO 2007/143168 | 12/2007 |
| WO | WO 2008/020079 | 2/2008 |
| WO | WO 2008/090901 | 7/2008 |
| WO | WO 2008/144763 A2 | 11/2008 |
| WO | WO 2009/010539 | 1/2009 |
| WO | WO 2009/014263 | 1/2009 |
| WO | WO 2009/041613 | 4/2009 |
| WO | WO 2009/041621 | 4/2009 |
| WO | WO 2009/041643 | 4/2009 |
| WO | WO 2009/044774 | 4/2009 |
| WO | WO 2009/125825 | 10/2009 |
| WO | WO 2009/148148 | 12/2009 |
| WO | WO 2010/021697 | 2/2010 |
| WO | WO 2010/035769 | 4/2010 |
| WO | WO 2010/065078 | 6/2010 |
| WO | WO 2010/107108 | 9/2010 |
| WO | WO 2010/115868 | 10/2010 |
| WO | WO 2011/013786 | 2/2011 |
| WO | WO 2011/149046 | 12/2011 |
| WO | WO 2011/149051 | 12/2011 |
| WO | WO 2011/154139 A2 | 12/2011 |
| WO | WO 2012/063875 | 5/2012 |
| WO | WO 2012/064627 | 5/2012 |
| WO | WO 2012/094703 | 7/2012 |
| WO | WO 2012/118750 | 9/2012 |
| WO | WO 2014/200018 | 12/2014 |
| WO | WO 2016/027859 | 2/2016 |
| WO | WO 2016/104777 | 6/2016 |
| WO | WO-2016104777 A1 * | 6/2016 | ............. A61K 31/28 |
| WO | WO 2016/136933 | 9/2016 |
| WO | WO 2016/186154 | 11/2016 |
| WO | WO 2018/008750 A1 | 1/2018 |
| WO | WO 2018/203545 | 11/2018 |
| WO | WO 2019/078344 A1 | 4/2019 |
| WO | WO 2019/151418 A1 | 8/2019 |
| WO | WO 2020/202839 | 10/2020 |
| WO | WO 2022/191306 | 9/2022 |
| WO | WO 2023/095852 A1 | 6/2023 |
| WO | WO 2023/140269 A1 | 7/2023 |

OTHER PUBLICATIONS

Park. "H3K27 Demethylase JMJD3 Employs the NF-κB and BMP Signaling Pathways to Modulate the Tumor Microenvironment and Promote Melanoma Progression and Metastasis". Cancer Res (2016) 76 (1): 161-170. https://doi.org/10.1158/0008-5472.CAN-15-0536 (Year: 2016).*

Ntziachristos, P., Tsirigos, A., Welstead, G. et al. Contrasting roles of histone 3 lysine 27 demethylases in acute lymphoblastic leukaemia. Nature 514, 513-517 (2014). (Year: 2014).*

Zehui. "Different expression patterns of histone H3K27 demethylases in renal cell carcinoma and bladder cancer". Cancer Biomarkers, vol. 18, No. 2, pp. 125-131, 2017. Abstract. (Year: 2017).*

Ando et al., "Tocilizumab, a Proposed Therapy for the Cachexia of Interleukin6-Expressing Lung Cancer," PLOS One, Jul. 1, 20140, 9(7):e102436. doi: 10.1371/journal.pone.0102436. eCollection 2014.

"Interleukin 6-wikipedia", Feb. 22, 2019, XP055598802, Retrieved from the Internet Jun. 24, 2019: URL:https://protect-us.mimecast.com/s/6UxpCmZ28nsApl8JnGhTki?domain=en.wikipedia.org.

Armour et al., "Recombinant human IgG molecules lacking Fcγ receptor I binding and monocyte triggering activities," Eur J Immunol, Aug. 1999, 29(8):2613-2624.

Srivastava et al., "Potassium Channel IGR.4.1 as an Immune Target in Multiple Sclerosis," N Engl J Med, Jul. 12, 2012, 367(2):115-123. doi:10.1056/NEJMoa1110740.

U.S. Appl. No. 18/820,608, Kakehi et al., filed Aug. 30, 2024.

U.S. Appl. No. 18/956,095, Igawa et al., filed Nov. 22, 2024.

U.S. Appl. No. 18/975,370, Igawa et al., filed Dec. 10, 2024.

U.S. Appl. No. 18/975,370, Igawa et al., Dec. 10, 2024.

(56)　　　　　References Cited

OTHER PUBLICATIONS

Airoldi et al., "IL-12 can target human lung adenocarcinoma cells and normal bronchial epithelial cells surrounding tumor lesions," PLoS One, Jul. 1, 2009, 4(7):e6119, 11 pages.
Akira et al., "The evidence for interleukin-6 as an autocrine growth factor in malignancy," Semin Cancer Biol, Feb. 1992, 3(1):17-26.
Alvarez et al., "Tumor necrosis factor-α exerts interleukin-6-dependent and -independent effects on cultured skeletal muscle cells," Biochim Biophys Acta, Jan. 30, 2002, 1542(1-3):66-72.
Ano et al., "Transcription Factors GATA-3 and RORγt are Important for Determining the Phenotype of Allergic Airway Inflammation in a Murine Model of Asthma," J Immunol, Feb. 1, 2013, 190(3):1056-1065. doi: 10.4049/jimmunol.1202386. Epub Jan. 4, 2013.
Armstrong et al., "Melanoma-Derived Interleukin 6 Inhibits In Vivo Melanoma Growth," J Invest Dermatol, Mar. 1994, 102(3):278-284.
Ashizawa et al., "Clinical significance of interleukin-6 (IL-6) in the spread of gastric cancer: role of IL-6 as a prognostic factor," Gastric Cancer, May 2005, 8(2):124-131.
Barton-Davis et al., "Viral mediated expression of insulin-like growth factor I blocks the aging-related loss of skeletal muscle formation," Proc Natl Acad Sci USA, Dec. 22, 1998, 95(26):15603-15607.
Beck et al., "Brief Report: Alleviation of Systemic Manifestations of Castleman's Disease by Monoclonal Anti-Interleukin-6 Antibody," N Engl J Med, Mar. 3, 1994, 330(9):602-605.
Becker, "Molecular Immunological Approaches to Biotherapy of Human Cancers—A Review. Hypothesis and Implications," Anticancer Res. Mar.-Apr. 2006, 26(2A):1113-1134.
Bellomo, "The Cytokine Network in the Critically Ill," Anaesth Intensive Care, Aug. 1992, 20(3):288-302.
Benda et al., "Interleukin-6 in islet xenograft rejection." Transpl Int. Mar. 2001, 14(2):63-71.
Berger et al., "Disruption of the Lcn2 gene in mice suppresses primary mammary tumor formation but does not decrease lunch metastasis," Proc Natl Acad Sci USA, Feb. 16, 2010, 107(7):2995-3000. doi: 10.1073/pnas.1000101107. Epub Feb. 1, 2010.
Bertagnolli et al., "IL-4-Supported Induction of Cytolytic T Lymphocytes Requires IL-2 and IL-6." Cell Immunol, Apr. 1, 1991, 133(2):327-341.
Besse et al., "Phase 2 Study of Frontline Bortezomib in Patients with Advanced Non-Small Cell Lung Cancer," Lung Cancer, Apr. 2012, 76(1):78-83. doi: 10.1016/j.lungcan.2011.09.006. Epub Dec. 18, 2011.
Biswas et al., "Involvement of IL-6 in the paracrine production of VEGF in ocular HSV-1 infection," Exp Eye Res, Jan. 2006, 82(1):46-54. Epub Jul. 11, 2005.
Bogdanovich et al., "Functional improvement of dystrophic muscle by myostatin blockade." Nature, Nov. 28, 2002, 420(6914):418-421.
Bond et al., "Synergistic upregulation of metalloproteinase-9 by growth factors and inflammatory cytokines: an absolute requirement for transcription factor NF-κB," Febs Lett, Sep. 11, 1998, 435(1):29-34.
Borg et al., "15-Deoxyspergualin inhibits interleukin 6 production in in vitro stimulated human lymphocytes," Transpl Immunol, Jun. 1996, 4(2):133-143.
Bork, "Powers and Pitfalls in Sequence Analysis: The 70% Hurdle," Genome Res, Apr. 2000, 10(4):398-400.
Bork et al., "Go hunting in sequence databases but watch out for the traps," Trends Genet, Oct. 1996, 12(10):425-427.
Borsellino et al., "Blocking Signaling through the Gp130 Receptor Chain by Interleukin-6 and Oncostatin M Inhibits PC-3 Cell Growth and Sensitizes the Tumor Cells to Etoposide and Cisplatin-Mediated Cytotoxicity," Cancer, Jan. 1, 1999, 85(1):134-144.
Brenner, "Errors in genome annotation," Trends Genet, Apr. 1999, 15(4):132-133.
Bromberg, "The IL-6/Jak/Stat3 Pathway: Targeting Metastatic Breast Cancer Research Update," posted on 2/29/2009, retrieved on Mar. 10, 2013, retrieved from URL <http://www.mountainsofhopefoundation.org/foundation-news/60-the-il-6jakstat3-pathway-. . .>, 4 pages.

Burska et al., "Gene expression analysis in RA: towards personalized medicine," Pharmacogenomics J, Apr. 2014. 14(2):93-106.
Cabillic et al., "Interleukin-6 and vascular endothelial growth factor release by renal cell carcinoma cells impedes lymphocyte-dendritic cell cross-talk," Clin Exp Immunol, Dec. 2006. 146(3):518-523.
Campbell et al., "Essential Role for Interferon-γ and Interleukin-6 in autoimmune Insulin-dependent Diabetes in NOD/Wehi Mice," J Clin Invest, Feb. 1991, 87(2):739-742.
Campbell et al., "Evidence for IL-6 Production by and Effects on the Pancreatic β-Cell," J Immunol, Aug. 15, 1989, 143(4):1188-1191.
Campo et al., "Comparative activity of Sant7 and anti-IL-6, IL-6R monoclonal antibodies in a murine model of B cell lymphoma," Cytokine, Sep. 7, 2005, 31(5):368-374.
Campochiaro, "Retinal and Choroidal Neovascularization," J Cell Physiol, Sep. 2000, 184(3):301-310.
Capelo et al., "Visceral adiposity is associated with cytokines and decrease in lung function in women with persistent asthma," Rev Port Pneumol, Sep.-Oct. 2016 22(5):255-261. doi: 10.1016/j.rppnen.2016.02.005. Epub Mar. 29, 2016.
Ceyhan et al., "Neural invasion in pancreatic cancer: A mutual tropism between neurons and cancer cells," Biochem Biophys Res Commun, Sep. 26, 2008, 374(3):442-447. Epub Jul. 18, 2008.
Charge et al., "Cellular and Molecular Regulation of Muscle Regeneration," Physiol Rev, Jan. 2004, 84(1):209-238.
Cheong et al., "Peritoneal healing and adhesion formation/reformation," Hum Reprod Update, Nov.-Dec. 2001, 7(6):556-566.
Choi et al., "IL-6 protects pancreatic islet beta cells from pro-inflammatory cytokines-induced cell death and functional impairment in vitro and in vivo," Transpl Immunol, Jun.-Jul. 2004, 13(1):43-53.
Chu et al., "Therapeutic potential of anti-IL-6 therapies for granulocytic airway inflammation in asthma," Allergy Asthma Clin Immunol, Apr. 2, 2015, 11(1):14. doi: 10.1186/s13223-015-0081-1. eCollection 2015.
Chung et al., "Serum Interleukin-6 Levels Reflect the Disease Status of Colorectal Cancer," J Surg Oncol, Aug. 2003, 83(4):222-226.
Chuntharapai et al., "Generation of Monoclonal Antibodies to Chemokine Receptors," Methods Enzymol, 1997, 288:15-27.
ClinicalTrials.gov [online], "A Phase 2a Study to Evaluate the Effects of Sirukumab in Subjects With Severe Poorly Controlled Asthma," NCT02794519, first posted Jun. 9, 2016, retrieved on Jul. 8, 2021, retrieved at URL <https://clinicaltrials.gov/ct2/show/NCT02794519>, 14 pages.
Culig et al., "Interleukin-6 regulates androgen receptor activity and prostate cancer cell growth," Mol Cell Endocrinol, Nov. 29, 2002, 197(1-2):231-238.
Dangott et al., "Dietary Creatine Monohydrate Supplementation Increases Satellite Cell Mitotic Activity During Compensatory Hypertrophy," Int J Sports Med, Jan. 2000, 21(1):13-16.
Darr et al., "Hindlimb suspension suppresses muscle growth and satellite cell proliferation," J Appl Physiol, Nov. 1989, 67(5):1827-1834.
Davies et al., "The HGF/SF Antagonist NK4 Reverses Fibroblast- and HGF-Induced Prostate Tumor Growth and Angiogenesis In Vivo," Int J Cancer, Sep. 1, 2003, 106(3):348-354.
De Vita et al., "Serum levels of interleukin-6 as a prognostic factor in advanced non-small cell lung cancer," Oncol Rep, May-Jun. 1998, 5(3):649-652.
Demir et al., "Nerve-Cancer Interactions in the Stromal Biology of Pancreatic Cancer," Frontiers in Physiology, 2012, 3(97):1-22.
Ding et al., "The change of plasma interleukin-6 level and cardiac protective effect of monoclonal antibody to IL-6 during myocardial infarction reperfusion," Chinese Journal of Cardiology, 1999, 27(1):29-32 (with English abstract).
Doerks et al., "Protein annotation: detective work for function prediction," Trends Genet, Jun. 1998, 14(6):248-250.
Doganci et al., "The IL-6R α chain controls lung CD4+CD25+ Treg development and function during allergic airway inflammation in vivo," J Clin Invest, Feb. 2005, 115(2):313-325.
Duluc et al., "Tumor-associated leukemia inhibitory factor and IL-6 skew monocyte differentiation into tumor-associated macrophage-like cells," Blood, Dec. 15, 2007, 110(13):4319-4330. Epub Sep. 11, 2007.

(56)             References Cited

OTHER PUBLICATIONS

Ebos et al., "Accelerated metastasis after short-term treatment with a potent inhibitor of tumor angiogenesis," Cancer Cell, Mar. 3, 2009, 15(3):232-239. doi: 10.1016/j.ccr.2009.01.021.

Eder et al., "Targeting the androgen receptor in hormone-refractory prostate cancer—new concepts," Future Oncol, Feb. 2005, 1(1):93-101.

Esty et al., "Abstract No. AB109: 346 Anti-IL-6 treatment in two pediatric patients with severe persistent asthma with the IL4R[576] variant," Presented at The AAAAI/WAO Joint Congress, Orlando, FL, Mar. 4, 2018; J Allergy Clin Immunol, 141(2), retrieved from URL <https://aaaai.confex.com/aaaai/wao18/webprogram/Paper34378.html>, 1 page.

Feaver et al., "Abstract No. 439: The Anti-IL-6 Antibody Sirukumab Inhibits Vascular Inflammation in a Human Surrogate Model of Atherosclerosis," Presented at 2014 ACR/ARHP Annual Meeting, Boston, MA, Nov. 14-19, 2014; American College of Rheumatology Meeting Abstracts, 2014, p. S187.

Finkel et al., "Negative Inotropic Effects of Cytokines on the Heart Mediated by Nitric Oxide," Science, Jul. 17, 1992, 257(5068):387-389.

Fisniku et al., "Protective Effects of PG490-88 on Chronic Allograft Rejection by Changing Intragraft Gene Expression Profiles," Transplant Proc, May 2005, 37(4):1962-1964.

Ford et al., "Evidence that Production of Interleukin 6 within the Rejecting Allograft Coincides with Cytotoxic T Lymphocyte Development," Transplantation, Mar. 1991, 51(3):656-661.

Fraunberger et al., "Cytokine and Cytokine-Receptor Profiles After Liver and Heart Transplantation," Transplant Proc, Jun. 1995, 27(3):2023-2027.

Fredj et al., "Role of Interleukin-6 in Cardiomyocyte/Cardiac Fibroblast Interactions During Myocyte Hypertrophy and Fibroblast Proliferation," J Cell Physiol, Aug. 2005, 204(2):428-436.

Fuchs et al., "Role of interleukin-6 for LV remodeling and survival after experimental myocardial infarction," FASEB J, Nov. 2003, 17(14):2118-2120. Epub Sep. 4, 2003.

Fujita et al., "Anti-Interleukin-6 Receptor Antibody Prevents Muscle Atrophy in Colon-26 Adenocarcinoma-Bearing Mice with Modulation of Lysosomal and ATP-Ubiquitin-Dependent Proteolytic Pathways," Int J Cancer, Nov. 27, 1996, 68(5):637-643.

Fujiwara et al., "1. Control of Tumor immunity by B cells and Th2 cytokines," Annual Review Meneki, 1999, pp. 257-269 (with English translation).

Furukawa et al., "Cytokine Gene Expression During the Development of Graft Coronary Artery Disease in Mice," Jpn Circ J, Oct. 1999, 63(10):775-782.

Gao et al., "Mutations in the EGFR kinase domain mediate STAT3 activation via IL-6 production in human lung adenocarcinomas," J Clin Invest, Dec. 2007, 117(12):3846-3856.

Garry et al., "Myogenic stem cell function is impaired in mice lacking the forkhead/winged helix protein MNF," Proc Natl Acad Sci USA, May 9, 2000, 97(10):5416-5421.

Garry et al., "Persistent Expression of MNF Identifies Myogenic Stem Cells in Postnatal Muscles," Dev Biol, Aug. 15, 1997, 188(2):280-294.

Ghosh et al., "Missing Pieces in the NF-κB Puzzle," Cell, Apr. 2002, vol. 109, Suppl:S81-S96.

Giugliano et al., "Verapamil inhibits interleukin-6 and vascular endothelial growth factor production in primary cultures of keloid fibroblasts," Br J Plast Surg, Dec. 2003, 56(8):804-809.

Greenberg et al., "Interleukin 6 Reduces Lipoprotein Lipase Activity in Adipose Tissue of Mice in Vivo and in 3T3-L1 Adipocytes: A Possible Role for Interleukin 6 in Cancer Cachexia," Cancer Res, Aug. 1, 1992, 52(15):4113-4116.

Greten et al., "IKKβ Links Inflammation and Tumorigenesis in a Mouse Model of Colitis-Associated Cancer," Cell, Aug. 6, 2004, 118(3):285-296.

Grossniklaus et al., "Perspective—Choroidal Neovascularization," Am J Ophthalmol, Mar. 2004, 137(3):496-503.

Guice et al., "Anti-Tumor Necrosis Factor Antibody Augments Edema Formation in Caerulein-Induced Acute Pancreatitis," J Surg Res, Dec. 1991, 51(6):495-499.

Guillen et al., "Cytokine signaling during myocardial infarction: sequential appearance of IL-1β and IL-6," Am J Physiol, Aug. 1995, 269(2 Pt 2):R229-R235.

Gwechenberger et al., "Cardiac Myocytes Produce Interleukin-6 in Culture and in Viable Border Zone of Reperfused Infarctions," Circulation, Feb. 2, 1999, 99(4):546-551.

Habara et al., "The biological effects of antiadhesion agents on activated RAW264.7 macrophages," J Biomed Mater Res, Sep. 15, 2002, 61(4):628-633.

Hanahan et al., "Hallmarks of Cancer: The Next Generation," Cell, Mar. 4, 2011, 144(5):646-674. doi: 10.1016/j.cell.2011.02.013.

Hashizume et al., "IL-6 plays an essential role in neutrophilia under inflammation," Cytokine, Apr. 2011, 54(1):92-99. doi: 10.1016/j.cyto.2011.01.007. Epub Feb. 2, 2011.

Hashizume et al., "Various actions of IL-6—Significance of IL-6 in autoimmune and inflammatory diseases," Folia Pharmacol Jpn, 2014, 144(4):172-177 (with English translation).

Hatzi et al., "N-myc oncogene overexpression down-regulates IL-6; evidence that IL-6 inhibits angiogenesis and suppresses neuroblastoma tumor growth," Oncogene, May 16, 2002, 21(22):3552-3561.

Hirai et al., "Perineural Invasion in Pancreatic Cancer," Pancreas, Jan. 2002, 24(1):15-25.

Hirota et al., "Continuous activation of gp130, a signal-transducing receptor component for interleukin 6-related cytokines, causes myocardial hypertrophy in mice," Proc Natl Acad Sci USA, May 23, 1995, 92(11):4862-4866.

Hirota et al., "Loss of a gp130 Cardiac Muscle Cell Survival Pathway Is a Critical Event in the Onset of Heart Failure during Biomechanical Stress," Cell, Apr. 16, 1999, 97(2):189-198.

Hocking et al., "Mechanisms of Pulmonary Edema Induced by Tumor Necrosis Factor-α," Circ Res, Jul. 1990, 67(1):68-77.

Hoffmann et al., "Inhibitory effects of verapamil isomers on the proliferation of choroidal endothelial cells," Graefes Arch Clin Exp Ophthalmol, Mar. 2006, 244(3):376-381. Epub Aug. 9, 2005.

Holmdahl, "The Role of Fibrinolysis in Adhesion Formation," Eur J Surg Suppl, 1997, (Supp 577):24-31.

Hong et al., "Interleukin-6 and its receptor in cancer: implications for translational therapeutics," Cancer, Nov. 1, 2007, 110(9):1911-1928.

Horinaga et al., "Clinical and Pathologic Significance of Activation of Signal Transducer and Activator of Transcription 3 in Prostate Cancer," Urology, Sep. 2005, 66(3):671-675.

Hornick et al., "Chapter 5 Chronic Rejection in the Heart," Methods Mol Biol, 2006, 333:131-44.

Huang et al., "Inhibition of STAT3 activity with AG490 decreases the invasion of human pancreatic cancer cells in vitro," Cancer Sci, Dec. 2006, 97(12):1417-1423. Epub Oct. 19, 2006.

Huang et al., "Inhibitory effect of AG490 on invasion and metastasis of human pancreatic cancer cells in vitro," Clin J Oncol, Dec. 2006, 28(12):890-893 (with English abstract).

Hudes et al., "Preliminary results of a phase I study: a chimeric monoclonal anti IL-6 antibody CNTO 328 in combination with docetaxel in patients with hormone refractory prostate cancer," Presented at 2007 ASCO Annual Meeting Proceedings, Chicago, IL, Jun. 2, 2007; Journal of Clinical Oncology (Post-Meeting Edition), Jun. 20, 2007, 25(18S):15521, 2 pages.

Idezawa et al., "Interleukin-6 Functions as an Autocrine Invasion Factor of Human Pancreatic Cancer Cells," Yamanashi Med J, 2004, 19(2):53-67.

Idezawa et al., "Interleukin-6 Functions as an Autocrine Invasion Factor of Human Pancreatic Cancer Cells," Yamanashi Med J, 2005, 20(2):xxxvi, 1 page (with English translation).

Ito et al.,"Regulation of damage to islets transplanted into the liver by IL-6 receptor antibody," Journal of Japan Surgical Society, 2006, 107(special extra issue 2):387(#PS-014-5) (English translation only).

Ito et al., "Induction of interleukin-6 by interferon alfa and its abrogation by a serine protease inhibitor in patients with chronic hepatitis C," Hepatology, Apr. 1996, 23(4):669-675.

Itoh et al., "Abstract No. 2838: Anti-IL-6 Receptor Antibody Down-Regulates Pro-Inflammatory Cytokine Production of Gr-1[+]

(56) References Cited

OTHER PUBLICATIONS

CD11b⁺ Cells and Prevents Early Loss of Islet Grafts in the Liver of Mice in Association with Engraftments," Poster, Presented at World Transplant Congress, Boston, MA, Jul. 22-27, 2006; Transplantation, Jul. 15, 2006, 82(1-Suppl 3):990, 1 page.

Izawa et al., "PE-269: Critical Role of Interleukin-6 and its Cross-talk with ATIR Signaling in Acute Rejection of Murine Cardiac Allografts," Poster, Presented at the 71st Annual Scientific Meeting of the Japanese Circulation Society, Kobe, Japan, Mar. 15-17, 2007; Circulation Journal, 2007, 71(Suppl.1):392.

Izawa et al., "Abstract No. 1084: Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," Poster, Present at American Transplant Congress 2007, San Francisco, CA, May 5-9, 2007; American Journal of Transplantation, 2007, (Suppl. 11):426.

Jejurikar et al., "Skeletal Muscle Denervation Increases Satellite Cell Susceptibility to Apoptosis," Plast Reconstr Surg, Jul. 2002, 110(1):160-168.

Jeron et al., "Systemic Immunosuppression Fails to Suppress Cardiac Cytokine Induction in Pressure Overload Hypertrophy in Rats," Immunobiology, Mar. 2002, 205(1):51-60.

Jones et al., "Disuse atrophy and exercise rehabilitation in humans profoundly affects the expression of genes associated with the regulation of skeletal muscle mass," FASEB J, Jun. 2004, 18(9):1025-1027. Epub Apr. 14, 2004.

Kallen et al., "New developments in IL-6 dependent biology and therapy: where do we stand and what are the options," Expert Opin Investig Drugs, Sep. 1999, 8(9):1327-1349.

Kami et al., "Gene Expression of Receptors for IL-6, LIF, and CNTF in Regenerating Skeletal Muscles," J Histochem Cytochem, Sep. 2000, 48(9):1203-1213.

Kamohara et al., "No. 2529: Activity of IL-6 on the growth and metastasis of pancreatic cancer cells, and the expression regulatory mechanism by stromal cells," The Japanese journal of gastroenterological surgery, Jul. 1, 2006, 39(7):1356 (with English translation).

Kan et al., "P-0539: The effect of anti-cancer agents on CD4⁺ FoxP3⁺ regulatory T cell," Poster, Presented at 68th Annual Meeting of the Japanese Cancer Association, Pacifico Yokohama, Japan, Oct. 1-3, 2009, p. 286.

Kanda et al., "Interleukin-6 and Cardiovascular Diseases," Jpn Heart J, Mar. 2004, 45(2):183-193.

Karin et al., "NF-κB at the crossroads of life and death," Nat Immunol, Mar. 2002, 3(3):221-227.

Karin et al., "NF-κB in Cancer: From Innocent Bystander to Major Culprit," Nat Rev Cancer, Apr. 2002, 2(4):301-310.

Kato, "A case of bronchial asthma in where IL-6 is considered to have been involved in making it refractory," Shindan to Chiryo Sha Inc., Oct. 10, 2018, 106(10):1287-1291 (with English translation).

Kayahara et al., "The Nature of Neural Invasion by Pancreatic Cancer," Pancreas, Oct. 2007, 35(3):218-223.

Kayahara et al., "Neural Invasion and Lymph Node Metastasis in the Head of the Pancreas Carcinoma," The Japanese Society of Gastroenterological Surgery, Mar. 1991, 24(3):813-817 (with English abstract).

Kim et al., "Carcinoma-produced factors activate myeloid cells through TLR2 to stimulate metastasis," Nature, Jan. 1, 2009, 457(7225):102-106. doi: 10.1038/nature07623.

Kitahara et al., "The in vivo Anti-tumor Effect of Human Recombinant Interleukin-6," Jpn J Cancer Res, Oct. 1990, 81(10):1032-1038.

Kitazawar et al., "Interleukin-1 Receptor Antagonist and Tumor Necrosis Factor Binding Protein Decrease Osteoclast Formation and Bone Resorption in Ovariectomized Mice," J Clin Invest, Dec. 1994, 94(6):2397-2406.

Klein et al., "Interleukin-6 in human multiple myeloma," Blood, Feb. 15, 1995, 85(4):863-872.

Knulst et al., "Cytokine detection and modulation in acute graft vs host disease in mice," Mediators Inflamm, 1994, 3(1):33-40.

Kobara et al., "Antibody against interleukin-6 receptor attenuates left ventricular remodelling after myocardial infarction in mice," Cardiovasc Res, Aug. 1, 2010, 87(3):424-430. Epub Mar. 7, 2010.

Kobara et al., "Abstract No. 851: Inhibition of Interleukin-6 Signaling Attenuates Left Ventricular Remodeling after Myocardial Infarction in Mice," Presented at The 78th Annual Scientific Session of the American-Heart-Association, Dallas, TX, Nov. 13-16, 2005; Circulation, Oct. 25, 2005, 112(17 Suppl S):U216, 2 pages.

Koch et al., "IL-6 activated integrated BATF/IRF4 functions in lymphocytes are T-bet-independent and reversed by subcutaneous immunotherapy," Sci Rep, Apr. 30, 2013, 3:1754, 9 pages. doi: 10.1038/srep01754.

Koide et al., "Establishment of Perineural Invasion Models and Analysis of Gene Expression Revealed an Invariant Chain (CD74) as a Possible Molecule Involved in Perineural Invasion in Pancreatic Cancer," Clin Cancer Res, Apr. 15, 2006, 12(8):2419-2426.

Konopatskaya et al., "Abstract No. 1749-B836: VEGF₁₆₅b, an Endogenous C-Terminal Splice Varian of VEGF, Inhibits Retinal Neovascularisation in Mice," Poster, Presented at 2006 Association for Research in Vision and Ophthalmology Annual Meeting, Ft. Lauderdale, FL, Apr. 30-May 4, 2006; Mol Vis, May 26, 2006, 12:626-632.

Kosaka et al., "Interferon-γ is a therapeutic target molecule for prevention of postoperative adhesion formation," Nat Med, Apr. 2008, 14(4):437-441. doi: 10.1038/nm1733. Epub Mar. 16, 2008.

Kurdi et al., "Increased expression of IL-6 and LIF in the hypertrophied left ventricle of TGR(mRen2)27 and SHR rats," Mol Cell Biochem, Jan. 2005, 269(1-2):95-101.

Kurek et al., "The Role of Leukemia Inhibitory Factor in Skeletal Muscle Regeneration," Muscle Nerve, Jul. 1997, 20(7):815-822.

Kurek et al., "Up-Regulation of Leukaemia Inhibitory Factor and Interleukin-6 in Transected Sciatic Nerve and Muscle Following Denervation," Neuromuscul Disord, Mar. 1996, 6(2):105-114.

Kuroda et al., "Prevention of Cancer Cachexia by a Novel Nuclear Factor κB Inhibitor in Prostate Cancer," Clin Cancer Res, Aug. 1, 2005, 11(15):5590-5594.

La Tulippe et al., "Comprehensive Gene Expression Analysis of Prostate Cancer Reveals Distinct Transcriptional Programs Associated with Metastatic Disease," Cancer Res, Aug. 1, 2002, 62(15):4499-4506.

Lancaster et al., "Identification of genes associated with ovarian cancer metastasis using microarray expression analysis," Int J Gynecol Cancer, Sep.-Oct. 2006, 16(5):1733-1745.

Lee et al., "Interleukin-6 Protects LNCaP Cells from Apoptosis Induced by Androgen Deprivation Through the Stat 3 Pathway," Prostate, Aug. 1, 2004, 60(3):178-186.

Li et al., "Phase II Study of the Proteasome Inhibitor Bortezomib (PS-341, Velcade®) in Chemotherapy-Naive Patients with Advanced Stage in Non-Small Cell Lung Cancer (NSCLC)," Lung Cancer, Apr. 2010, 68(1):89-93. doi: 10.1016/j.lungcan.2009.05.009. Epub Jun. 12, 2009.

Liao et al., "Tissue Infiltration," Tumor Metastasis, Shanxi Science and Technology Press, Feb. 2007, pp. 15-16 (with English translation).

Lin et al., "Critical role of IL-6 in dendritic cell-induced allergic inflammation of asthma," J Mol Med (Berl), Jan. 2016, 94(1):51-59. doi: 10.1007/s00109-015-1325-8. Epub Aug. 2, 2015.

nlm.nih.gov [online], "Liver Metastases," U.S. National Library of Medicine—National Institutes of Health (NIH), MedlinePlus Medical Encyclopedia, retrieved on Nov. 22, 2014, retrieved from URL <http://www.nlm.nih.gov/medlineplus/ency/article/000277.html>, 3 pages.

Luo et al., "A Proteasome Inhibitor Effectively Prevents Mouse Heart Allograft Rejection," Transplantation, Jul. 27, 2001, 72(2):196-202.

Maeda et al., "Abstract No. 630: Role of IKKβ / NF-κB Activation for Development of Liver Metastasis," Presented at The 58th Annual Meeting of the American Association for the Study of Liver Diseases, Boston, MA, Nov. 2-6, 2007; Hepatology, Oct. 2007, 46(4):518A, 1 page.

Maeda et al., "IKKβ Couples Hepatocyte Death to Cytokine-Driven Compensatory Proliferation that Promotes Chemical Hepatocarcinogenesis," Cell, Jul. 1, 2005, 121(7):977-990.

(56)             References Cited

OTHER PUBLICATIONS

Maeda et al., "Ikappa B Kinaseβ/Nuclear Factor-κB Activation Controls the Development of Liver Metastasis by Way of Interleukin-6 Expression," Hepatology, Dec. 2009, 50(6):1851-1860.

Marten et al., "Bortezomib is Ineffective in an Orthotopic Mouse Model of Pancreatic Adenocarcinoma," Mol Cancer Ther, Nov. 2008, 7(11):3624-3631. doi: 10.1158/1535-7163.MCT-08-0393.

Martignoni et al., "Role of Mononuclear Cells and Inflammatory Cytokines in Pancreatic Cancer-Related Cachexia," Clin Cancer Res, Aug. 15, 2005, 11(16):5802-5808.

Massoud et al., "An asthma-associated IL4R variant exacerbates airway inflammation by promoting conversion of regulatory T cells to TH17-like cells," Nat Med, Sep. 2016, 22(9):1013-1022. doi: 10.1038/nm.4147. Epub Aug. 1, 2016.

Masui et al., "Expression of IL-6 receptor in pancreatic cancer: involvement in VEGF induction," Anticancer Res, Nov.-Dec. 2002, 22(6C):4093-4100.

Matsuda et al., "Establishment of an interleukin 6 (IL 6)/B cell stimulatory factor 2-dependent cell line and preparation of anti-IL6 monoclonal antibodies," Eur J Immunol, Jun. 1988, 18(6):951-956.

Matsushita et al., "Interleukin-6/soluble interleukin-6 receptor complex reduces infarct size via inhibiting myocardial apoptosis," Lab Invest, Oct. 2005, 85(10):1210-1223.

Matzaraki et al., "Evaluation of serum procalcitonin and interleukin-6 levels as markers of liver metastasis," Clin Biochem, Mar. 2007, 40(5-6):336-342. Epub Jan. 10, 2007.

Mauro, "Satellite Cell of Skeletal Muscle Fibers," J Biophys Biochem Cytol, Feb. 1961, 9:493-495.

McCormick et al., "Role of Satellite Cells in Altering Myosin Expression During Avian Skeletal Muscle Hypertrophy," Dev Dyn, Jan. 1994, 199(1):52-63.

Meng et al., "Abstract 165: Acquired Resistance to Chemotherapy in Human Cholangiocarcinoma Is Mediated By An Interleukin-6 (IL-6) Dependent Activation of the X-Linked Inhibitor of Apoptosis (xiap) Protein," Gastroenterology, 2005, 128(4):Supplement 2, p. A-30.

Meng et al., "Over-expression of interleukin-6 enhances cell survival and transformed cell growth in human malignant cholangiocytes," J Hepatol, Jun. 2006, 44(6):1055-1065. Epub Dec. 13, 2005.

cancer.gov [online], "Metastatic Cancer: Questions and Answers," National Cancer Institute, U.S. National Institutes of Health (NIH), retrieved on Nov. 22, 2014, retrieved via Internet Archive: Wayback Machine URL <http:/web.archive.org/web/20100110123630/http://www.cancer.gov/cancertopics/factsheet. . . 3 pages.

Michalaki et al., "Serum levels of IL-6 and TNF-α correlate with clinicopathological features and patient survival in patients with prostate cancer," Br J Cancer, Jun. 14, 2004, 90(12):2312-2316.

Ming et al., "IL-6 enhances the generation of cytolytic T lymphocytes in the allogenic mixed leucocyte reaction," Clin Exp Immunol, Jul. 1992, 89(1):148-153.

Mitsunaga et al., "Nerve invasion distance is dependent on laminin γ2 in tumors of pancreatic cancer," International Journal of Cancer, Aug. 2010, 127(4)805-819.

Mitsunaga et al., "Detail Histologic Analysis of Nerve Plexus Invasion in Invasive Ductal Carcinoma of the Pancreas and Its Prognostic Impact," Am J Surg Pathol, Nov. 2007, 31(11):1636-1644.

Miyamoto et al., "Interleukin-6 Inhibits Radiation Induced Apoptosis in Pancreatic Cancer Cells," Anticancer Res, Jul.-Aug. 2001, 21(4A):2449-2456.

Moss et al., "Satellite Cells as the Source of Nuclei in Muscles of Growing Rats," Anat Rec, Aug. 1971, 170(4):421-435.

Mozdziak et al., "Quantitation of Satellite Cell Proliferation in Vivo Using Image Analysis," Biotech Histochem, Sep. 1994, 69(5):249-252.

Mozdziak et al., "Unloading of juvenile muscle results in a reduced muscle size 9 wk after reloading," J Appl Physiol, Jan. 2000, 88(1):158-164.

Mozdziak et al., "Muscle regeneration during hindlimb unloading results in a reduction in muscle size after reloading," J Appl Physiol, Jul. 2001, 91(1):183-190.

Mozdziak et al., "Hindlimb suspension reduces muscle regeneration," Eur J Appl Physiol Occup Physiol, Jul. 1998, 78(2):136-140.

Mukaida et al., "Cytokines and immune network," Rinsho Kensa, 1991, 35(5):447-452 (with English translation).

Mulhearn et al., "Using the Immunophenotype to Predict Response to Biologic Drugs in Rheumatoid Arthritis," J Pers Med, Oct. 2, 2019, 9(4):46, 15 pages.

Murata et al., "Possible Implication of Cytokines in the Pathophysiology of Acute Pancreatitis," Latest Medicine, 1992, 47(11):49-56 (with English translation).

Murphy, "Abstract No. 476.6: The effect of mechanical stretch on proliferation and differentiation of C2C12 cells," Presented at Experimental Biology 2004, Washington, DC, Apr. 17-21, 2004; FASEB J, 18:A743, 1 page.

Nagai et al., "No. 90: Suppression of experimental choroid neovascularization by inhibition of interleukin-6 receptor," Inflammation and Regeneration, Jul. 2006, 26(4):367.

Nakamura, "The basics and clinical aspects of angiogenesis—II. angiogenesis and tumors—8. Invasion/Metastasis/Tumor suppression of angiogenesis-inhibitory factor NK4," Presented at The 120th Annual JAMS Symposium, Apr. 2, 2022, pp. 57-66.

Nakashima et al., "Serum Interleukin 6 as a Prognostic Factor in Patients with Prostate Cancer," Clin Cancer Res, Jul. 2000, 6(7):2702-2706.

Narita et al., "Gemcitabine selectively depletes CD11b$^+$Gr-1$^+$ immature myeloid cells in tumor-bearing mice and enhances anti-tumor immune response," Society for Fundamental Cancer Immunology, 2006, 10:49 (with English translation).

seer.cancer.gov [online], "Cancer Stat Facts: Pancreas Cancer," National Cancer Institute, retrieved on Apr. 25, 2017, retrieved at URL <https://seer.cancer.gov/statfacts/html/pancreas.html> 9 pages.

Naugler et al., "Gender Disparity in Liver Cancer Due to Sex Differences in MyD88-Dependent IL-6 Production," Science, Jul. 6, 2007, 317(5834):121-124.

Negoro et al., "Activation of JAK/STAT pathway transduces cytoprotective signal in rat acute myocardial infarction," Cardiovasc Res, Sep. 2000, 47(4):797-805.

Ngo et al., "Computational Complexity, Protein Structure Prediction, and the Levinthal Paradox," The Protein Folding Problem and Tertiary Structure Prediction, 1994, Chapter 14, pp. 433-506.

Nishimoto et al., "Anti-interleukin 6 receptor antibody treatment in rheumatic disease," Ann Rheum Dis, Nov. 2000, 59(suppl I):i21-i27.

Nishimoto et al., "Inhibition of IL-6 for the treatment of inflammatory diseases," Curr Opin Pharmacol, Aug. 2004, 4(4):386-391.

Ogata et al., "Early administration of IL-6RA does not prevent radiation-induced lung injury in mice," Radiation Oncology, 2010, 5:26, 6 pages.

Ogata et al., "Anti-IL-6 receptor antibody does not ameliorate radiation pneumonia in mice," Exp Ther Med, Aug. 2012, 4(2):273-276.

Ohashi et al., "Interferon γ and plasminogen activator inhibitor 1 regulate adhesion formation after partial hepatectomy," Br J Surg, Mar. 2014, 101(4):398-407. doi: 10.1002/bjs.9405.

Ohsugi et al., "Pharmacological and Clinical Profile of Humanized Anti-human IL-6 Receptor Antibody (Tocilizumab), a Therapeutic Drug for Castleman's Disease," Folia Pharmacol Jpn, Dec. 2005, 126(6):419-425 (with English translation).

Ohtsuka et al., "Relation of Circulating Interleukin-6 to Left Ventricular Remodeling in Patients with Reperfused Anterior Myocardial Infarction," Clin Cardiol, Jul. 2004, 27(7):417-420.

Okada et al., "Experimental Implication of Celiac Ganglionotropic Invasion of Pancreatic-Cancer Cells Bearing c-ret Proto-Oncogene with Reference to Glial-Cell-Line-Derived Neurotrophic Factor (GDNF)," Int J Cancer, Mar. 31, 1999, 81(1):67-73.

Okada et al., "Elevated Serum Interleukin-6 Levels in Patients with Pancreatic Cancer," Jpn J Clin Oncol, Jan. 1998, 28(1):12-15.

Okada et al., "IL-6/BSF-2 Functions as a Killer Helper Factor in the in Vitro Induction of Cytotoxic T Cells," J Immunol, Sep. 1, 1988, 141(5):1543-1549.

(56)        References Cited

OTHER PUBLICATIONS

Okamoto et al., "P-066: Inhibition of Interleukin-6 Signaling Attenuates Left Ventricular Remodeling After Experimental Myocardial Infarction," Presented at The 9th Annual Scientific Meeting of the Japanese Heart Failure Society, Tokyo, Japan, Oct. 11-13, 2005; Journal of Cardiac Failure, Nov. 25, 2005, 11(9 Supple 1):S317, 3 pages.

Okamoto et al., "Interleukin-6 as a Paracrine and Autocrine Growth Factor in Human Prostatic Carcinoma Cells In Vitro," Cancer Res, Jan. 1, 1997, 57(1):141-146.

Okazaki et al., "Characterization of anti-mouse interleukin-6 receptor antibody," Immunol Lett, Dec. 3, 2002, 84(3):231-240.

Ono et al., "The effect of IL-6 on the des-gamma-carboxy prothrombin synthesis in human hepatoma cells," Gastroenterol Jpn, Dec. 1992, 27(6):745-750.

Ono et al., "Cytokine Gene Expression After Myocardial Infarction in Rat Hearts," Circulation, Jul. 14, 1998, 98(2):149-156.

Ozaki et al., "Effectiveness of multimodality treatment for resectable pancreatic cancer," Int J Pancreatol, Aug.-Nov. 1990, 7(1-3):195-200.

Ozaki et al., "The prognostic significance of lymph node metastasis and intrapancreatic perineural invasion in pancreatic cancer after curative resection," Surg Today, 1999, 29(1):16-22.

Paez-Ribes et al., "Antiangiogenic therapy elicits malignant progression of tumors to increased local invasion and distant metastasis," Cancer Cell, Mar. 3, 2009, 15(3):220-231. doi: 10.1016/j.ccr. 2009.01.027.

Park et al., "Interleukin-6 Protects MIN6 β Cells from Cytokine-Induced Apoptosis," Ann NY Acad Sci, Nov. 2003, 1005:242-249.

Patel et al., "Endogenous Interleukin-6 Enhances the Renal Injury, Dysfunction, and Inflammation Caused by Ischemia/Reperfusion," The Journal Pharmacology and Experimental Therapeutics, May 2005, 312(3):1170-1178.

Paul et al., "Immunologic Aspects of Clinical Transplantation," Fundamental Immunology, 3rd ed., 1993, Chapter 31, pp. 1124-1125.

Paule, "Reappraisal of the Concept of Hormone Therapy in Metastatic Prostate Cancer and Implications for Treatment," Eur Urol, Jun. 2005, 47(6):729-735. Epub Mar. 28, 2005.

Pauleikhoff et al., "Neovascular Age-Related Macular Degeneration," Retina, Dec. 2005, 25(8):1065-1084.

Peters et al., "Plasma IL6 levels, metabolic dysfunction, and asthma severity: a cross-sectional analysis of two cohorts," Lancet Respir Med, Jul. 2016, 4(7):574-584. doi: 10.1016/S2213-2600(16)30048-0. Epub Jun. 6, 2016.

Phillips, "The challenge of gene therapy and DNA delivery," J Pharm Pharmacol, Sep. 2001, 53(9):1169-1174.

Pikarsky et al., "NF-κB functions as a tumour promoter in inflammation-associated cancer," Nature, Sep. 23, 2004, 431(7007):461-466. Epub Aug. 25, 2004.

Pirollo et al., "Targeted Delivery of Small Interfering RNA: Approaching Effective Cancer Therapies," Cancer Res, Mar. 1, 2008, 68(5):1247-1250.

Poli et al., "Interleukin-6 deficient mice are protected from bone loss caused by estrogen depletion," EMBO J, Mar. 1, 1994, 13(5):1189-1196.

Porgador et al., "Interleukin 6 Gene Transfection into Lewis Lung Carcinoma Tumor Cells Suppresses the Malignant Phenotype and Confers Immunotherapeutic Competence against Parental Metastatic Cells," Cancer Res, Jul. 1, 1992, 52(13):3679-3686.

Puhakka et al., "Interleukin-6 and Tumor Necrosis Factor Alpha in Relation to Myocardial Infarct Size and Collagen Formation," J Card Fail, Aug. 2003, 9(4):325-332.

"Q&A—What is pancreatic islet transplantation," de wakaru himan to tounyoubyou, 2004, 3(6):982-984.

Quentmeier et al., "Role of IL-6, IL-2, and IL-4 in the in vitro induction of cytotoxic T cells," J Immunol, Nov. 15, 1992, 149(10):3316-3320.

Ramzy et al., "Cardiac allograft vasculopathy: a review," Can J Surg, Aug. 2005, 48(4):319-327.

Reed et al., "A neurokinin 1 receptor antagonist decreases postoperative peritoneal adhesion formation and increases peritoneal fibrinolytic activity," Proc Natl Acad Sci USA, Jun. 15, 2004, 101(24):9115-9120. Epub Jun. 8, 2004.

anzctr.org.au [online], "A clinical trial of Tocilizumab in participants with asthma," Reg. No. ACTRN12614000123640, registered Feb. 3, 2014, retrieved on Jul. 8, 2021, retrieved from URL https://www.anzctr.org.au/Trial/Registration/TrialReview.aspx?id= 365668, 8 pages.

Revez et al., "The Role of the Interleukin-6 Pathway in Asthma," Thesis for the degree of Doctor of Philosophy, The University of Queensland, Faculty of Medicine, 2018, pp. 78-115, retrieved on Mar. 13, 2019, retrieved from URL<https://espace.library.uq.edu. au/view/UQ:5f9d90b/s43414462_final_thesis.pdf>, 241 pages.

Rikiishi et al., "The roles of cytokine in organ-specific tumor metastasis," Hum Cell, Mar. 1993, 6(1):21-28 (Abstract only).

Saba et al., "Effects of Interleukin-6 and its Neutralizing Antibodies on Peritoneal Adhesion Formation and Wound Healing," Am Surg, Jul. 1996, 62(7):569-572.

Sacchi et al., "Treatment with Monoclonal Antibody to a Lewis Lung Carcinoma-Associated Antigen: Different Effects on Primary Tumor and its Metastases," Cancer Treat Rep, Sep. 1985, 69(9):985-991.

Salgado et al., "Circulating Interleukin-6 Predicts Survival in Patients with Metastatic Breast Cancer," Int J Cancer, Feb. 20, 2003, 103(5):642-646.

Sanayama et al., "Prediction of Therapeutic Responses to Tocilizumab in Patients with Rheumatoid Arthritis," Arthritis Rheumatol, Jun. 2014, 66(6):1421-1431.

Sansone et al., "IL-6 triggers malignant features in mammospheres from human ductal breast carcinoma and normal mammary gland," J Clin Invest, Dec. 2007, 117(12):3988-4002.

Sarkar et al., "Back to the Future: COX-2 Inhibitors for Chemoprevention and Cancer Therapy," Mini Rev Med Chem, Jun. 2007, 7(6):599-608.

Schultz, "Satellite Cell Proliferative Compartments in Growing Skeletal Muscles," Dev Biol, Apr. 10, 1996, 175(1):84-94.

Schultz et al., "Acute effects of hindlimb unweighting on satellite cells of growing skeletal muscle," J Appl Physiol, Jan. 1994, 76(1):266-270.

Schultz et al., "Response of Satellite Cells to Focal Skeletal Muscle Injury," Muscle Nerve, Mar.-Apr. 1985, 8(3):217-222.

Seddon et al., "Progression of Age-Related Macular Degeneration," Arch Ophthalmol, Jun. 2005, 123(6):774-782.

Shang et al., "IL-6 and TNF-α promote metastasis of lung cancer by inducing epithelial-mesenchymal transition," Oncol Lett, Jun. 2017, 13(6):4657-4660.

Shewach et al., "Gemcitabine and radiosensitization in human tumor cells," Invest New Drugs, 1996, 14(3):257-263.

Shimazaki et al., "Human myeloma model and antitumor effect of anti-human IL-6 receptor antibody," Rinsho Ketsueki, Apr. 1997, 38(4):281-284 (English translation only).

Shimizu et al., "KRP-203, a Novel Synthetic Immunosuppressant, Prolongs Graft Survival and Attenuates Chronic Rejection in Rat Skin and Heart Allografts," Circulation, Jan. 18, 2005, 111(2):222-229. Epub Jan. 10, 2005.

Shimizu et al., "Cancer Anti-angiogenic Therapy," Biol Pharm Bull, May 2004, 27(5):599-605.

Shinriki et al., "Humanized anti-interleukin-6 receptor antibody suppresses tumor angiogenesis and in vivo growth of human oral squamous cell carcinoma," Clin Cancer Res, Sep. 1, 2009, 15(17):5426-5434.

Sideleva et al., "Obesity and Asthma—An Inflammatory Disease of Adipose Tissue Not the Airway," Am J Respir Crit Care Med, Oct. 1, 2012, 186(7):598-605. doi: 10.1164/rccm.201203-0573OC. Epub Jul. 26, 2012.

Skolnick et al., "From genes to protein structure and function: novel applications of computational approaches in the genomic era," Trends Biotechnol, Jan. 2000, 18(1):34-39.

Skurkovich et al., "Anticytokine therapy—new approach to the treatment of autoimmune and cytokine-disturbance diseases," Oncology and Immunopathology, 2003, 2(4):71-80 (with English abstract).

(56)             References Cited

OTHER PUBLICATIONS

Sleeman et al., "Cancer metastasis as a therapeutic target," Eur J Cancer, May 2010, 46(7):1177-1180. doi: 10.1016/j.ejca.2010.02.039. Epub Mar. 20, 2010.

Smith et al., "The challenges of genome sequence annotation or 'The devil is in the details'," Nat Biotechnol, Nov. 1997, 15(12):1222-1223.

Smith et al., "Anti-Interleukin-6 Monoclonal Antibody Induces Regression of Human Prostate Cancer Xenografts in Nude Mice," Prostate, Jun. 15, 2001, 48(1):47-53.

Snow, "Myogenic Cell Formation in Regenerating Rat Skeletal Muscle Injured by Mincing," Anat Rec, Jun. 1977, 188(2):181-199.

Snow, "Satellite Cell Response in Rat Soleus Muscle Undergoing Hypertrophy Due to Surgical Ablation of Synergists," Anat Rec, Aug. 1990, 227(4):437-446.

Sparano et al., "Modulation of Th1 and Th2 cytokine profiles and their association with advanced head and neck squamous cell carcinoma," Otolaryngol Head Neck Surg, Nov. 2004, 131(5):573-576.

Stan et al., "In vivo inhibition of angiogenesis and growth of the human U-87 malignant glial tumor by treatment with an antibody against basic fibroblast growth factor," J Neurosurg, Jun. 1995, 82(6):1044-1052.

Steeg, "Tumor metastasis: mechanistic insights and clinical challenges," Nat Med, Aug. 2006, 12(8):895-904.

Steeg et al., "Metastasis: a therapeutic target for cancer," Nat Clin Pract Oncol, Apr. 2008, 5(4):206-219. Epub Feb. 5, 2008.

Strassmann et al., "Evidence for the Involvement of Interleukin 6 in Experimental Cancer Cachexia," J Clin Invest, May 1992, 89(5):1681-1684.

Studebaker et al., "Fibroblasts Isolated from Common Sites of Breast Cancer Metastasis Enhance Cancer Cell Growth Rates and Invasiveness in an Interleukln-6-Dependent Manner," Cancer Res, Nov. 1, 2008, 68(21):9087-9095.

Sugahara et al., "Expression of Interleukin-6 in Human Intrahepatic Biliary Tract and its Pathologic Significance; An Immunohistochemical and In Situ Hybridization Study," Journal of the Juzen Medical Society, 1996, 105(6):819-833 (with English abstract).

Suzuki et al., "Gemcitabine Selectively Eliminates Splenic Gr-1$^+$/CD11b$^+$ Myeloid Suppressor Cells in Tumor-Bearing Animals and Enhances Antitumor Immune Activity," Clin Cancer Res, Sep. 15, 2005, 11(18):6713-6721.

Suzuki et al., "Anti-inflammatory mechanism of tocilizumab, a humanized anti-IL-6R antibody: effect on the expression of chemokine and adhesion molecule," Rheumatol Int, Jan. 2010, 30(3):309-315. doi: 10.1007/s00296-009-0953-0. Epub May 23, 2009.

Takahashi et al., "Antiproteases in preventing the invasive potential of pancreatic cancer cells," JOP, Jul. 9, 2007, 8(4 Suppl):501-508.

Takeda et al., "Murine Tumor Cells Metastasizing Selectively in the Liver: Ability to Produce Hepatocyte-activating Cytokines Interleukin-1 and/or -6," Jpn J Cancer Res, Nov. 1991, 82(11):1299-1308.

Takizawa et al., "Growth inhibition of human lung cancer cell lines by interleukin 6 in vitro: a possible role in tumor growth via an autocrine mechanism," Cancer Res, Sep. 15, 1993, 53(18):4175-4181.

Tanaka et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Res, Apr. 1, 1997, 57(7):1335-1343.

Tantraworasin et al., "Prognostic factors of tumor recurrence in completely resected non-small cell lung cancer," Cancer Manag Res, Jun. 6, 2013, 5:77-84. doi: 10.2147/CMAR.S45642. Print 2013.

Tisdale, "Biology of Cachexia," J Natl Cancer Inst, Dec. 3, 1997, 89(23):1763-1773.

Tobe et al., "Animal Model—Targeted Disruption of the FGF2 Gene Does Not Prevent Choroidal Neovascularization in a Murine Model," Am J Pathol, Nov. 1998, 153(5):1641-1646.

Trikha et al., "Targeted Anti-Interleukin-6 Monoclonal Antibody Therapy for Cancer: A Review of the Rationale and Clinical Evidence," Clin Cancer Res, Oct. 15, 2003, 9(13):4653-4665.

Tsuchiya, "Therapeutic Antibody," Presented at Credit Suisse Seminar at Fuji-Gotemba Laboratories, Chugai Pharmaceutical Co., Ltd., Sep. 22, 2006, p. 21 (with English translation).

Tsujinaka et al., "Interleukin 6 Receptor Antibody Inhibits Muscle Atrophy and Modulates Proteolytic Systems in Interleukin 6 Transgenic Mice," J Clin Invest, Jan. 1, 1996, 97(1):244-249.

Ulich et al., "Rapid Communication—Intratracheal Injection of Endotoxin and Cytokines, II. Interleukin-6 and Transforming Growth Factor Beta Inhibit Acute Inflammation," Am J Pathol, May 1991, 138(5):1097-1101.

Valantine, "Cardiac Allograft Vasculopathy After Heart Transplantation: Risk Factors and Management," J Heart Lung Transplant, May 2004, 23(5 Suppl):S187-S193.

Vidal et al., "Making sense of antisense," Eur J Cancer, Dec. 2005, 41(18):2812-2818. Epub Nov. 9, 2005.

Vincent et al., "5-Fluorouracil Selectively Kills Tumor-Associated Myeloid-Derived Suppressor Cells Resulting in Enhanced T Cell-Dependent Antitumor Immunity," Cancer Res, Apr. 15, 2010, 70(8):3052-3061. doi: 10.1158/0008-5472.CAN-09-3690. Epub Apr. 13, 2010.

Wang et al., "Mechanical load-dependent regulation of satellite cell and fiber size in rat soleus muscle," Am J Physiol Cell Physiol, Apr. 2006, 290(4):C981-C989. Epub Nov. 16, 2005.

Wang et al., "Phase II Study of Panobinostat and Bortezomib in Patients with Pancreatic Cancer Progressing on Gemcitabine-Based Therapy," Anticancer Res, Mar. 2012, 32(3):1027-1032.

Wang et al., "IL-6 pathway-driven investigation of response to IL-6 receptor inhibition in rheumatoid arthritis," BMJ Open, Aug. 19, 2013, 3(8):e003199, 10 pages.

Wang et al., "Endogenous and Exogenous IL-6 Inhibit Aeroallergen-Induced Th2 Inflammation," J Immunol, Oct. 1, 2000, 165(7):4051-4061.

Warren et al., "Physiological role of tumor necrosis factor $\alpha$ in traumatic muscle injury," FASEB J, Oct. 2002, 16(12):1630-1632. Epub Aug. 7, 2002.

Webber et al., "Heart and lung transplantation in children," Lancet, Jul. 1, 2006, 368(9529):53-69.

Wei et al., "Keratinocyte Growth Factor Combined with a Sodium Hyaluronate Gel Inhibits Postoperative Intra-Abdominal Adhesions," Int J Mol Sci, Sep. 22, 2016, 17(10):1611, 17 pages. doi: 10.3390/ijms17101611.

Wells, "Additivity of Mutational Effects in Proteins," Biochemistry, Sep. 18, 1990, 29(37):8509-8517.

Weyand et al., "Serial Interleukin-6 Blood Levels Early After Cardiac Transplantation," Transplant Proc, Dec. 1992, 24(6):2546, 1 page.

Wilansky, "Echocardiography in the Assessment of Complications of Myocardial Infarction," Tex Heart Inst J, 1991, 18(4):237-242.

Wong et al., "Progress in heart transplantation," Cardiovasc Pathol, Jul.-Aug. 2005, 14(4):176-180.

Wright et al., "Neutrophil biomarkers predict response to therapy with tumor necrosis factor inhibitors in rheumatoid arthritis," J Leukoc Biol, Mar. 2017, 101(3):785-779.

Xing et al., "The Effect of Interleukin-6 on the Proliferation of Prostate Cancer Cells in Vitro and the Modulation of This Procedure," J Tongji Med Univ, 2001, 21(3):225-227.

Yamakawa et al., "P022: Astrocytes Promote the Proliferation of Lung Cancer Cells In Brain Metastases via Inflammatory cytokines, especially IL-6," Neuroscience, Jun. 1, 2009, 48(2/3):216.

Yamamoto et al., "Regulatory Mechanisms for Production of IFN-$\gamma$ and TNF by Antitumor T Cells or Macrophages in the Tumor-Bearing State," J Immunol, Mar. 1, 1995, 154(5):2281-2290.

Yamauchi-Takihara et al., "Hypoxic Stress Induces Cardiac Myocyte-Derived Interleukin-6," Circulation, Mar. 1, 1995, 91(5):1520-1524.

Yan et al., "(II) Abdominal discomfort and pain," Theory and Practice of Oncology, Shandong Science and Technology Press, Jul. 2006, 2 pages (with English translation).

Yang et al., "Enhanced induction of antitumor T-cell responses by cytotoxic T lymphocyte-associated molecule-4 blockade: the effect

(56) References Cited

OTHER PUBLICATIONS is manifested only at the restricted tumor-bearing stages," Cancer Res, Sep. 15, 1997, 57(18):4036-4041.

Yoshio-Hoshino et al., "Establishment of a New Interleukin-6 (IL-6) Receptor Inhibitor Applicable to the Gene Therapy for IL-6-Dependent Tumor," Cancer Res, Feb. 1, 2007, 67(3):871-875.

Yue et al., "Cytokine expression increases in nonmyocytes from rats with postinfarction heart failure," Am J Physiol, Jul. 1998, 275(1 Pt 2):H250-H258.

Zaki et al., "CNTO 328, A monoclonal antibody to IL-6, inhibits human tumor-induced cachexia in nude mice," Int J Cancer, Sep. 10, 2004, 111(4):592-595.

Zangari et al., "Immunomodulatory drugs in multiple myeloma," Expert Opin Investig Drugs, Nov. 2005, 14(11):1411-1418.

Zhang et al., "Serum Interleukin-6 Levels Correlate to Tumor Progression and Prognosis in Metastatic Breast Carcinoma," Anticancer Res, Mar.-Apr. 1999, 19(2B):1427-1432.

USPTO Non-Final Office Action in U.S. Appl. No. 15/553,609, dated Sep. 4, 2018, 20 pages.

Abramson et al., "Blocking the effects of IL-1 in rheumatoid arthritis protects bone and cartilage," Rheumatology (Oxford), Sep. 2002, 41(9):972-980.

Bendele et al., "Effects of interleukin 1 receptor antagonist alone and in combination with methotrexate in adjuvant arthritic rats," J Rheumatol, Jun. 1999, 26(6):1225-1229.

Hashizume et al., "Interleukin-6 regulates anti-arthritic effect of methotrexate via reduction of SLC19A1 expression in a mouse arthritis model," Arthritis Res Ther, Apr. 30, 2012, 14(2):R96.

Jones et al., "Replacing the complementarity-determining regions in a human antibody with those from a mouse," Nature, May 29-Jun. 4, 1986, 321(6069):522-525.

Maeda et al., "Essential roles of Ikkβ/Nf-κB Activation for Development of Liver Metastasis in Mice," Gastroenterology, Abstracts from the 107th Annual Meeting of the American Gastroenterological Association May 19-24, 2006;130(4) Suppl 2, Abstract A 750, 3 pages.

U.S. Appl. No. 18/096,066, Igawa et al., filed Jan. 12, 2023.

Digiacomo et al., "Tumor Hypoxia As an Enhancer of Inflammation-Mediated Metastasis: Emerging Therapeutic Strategies," Target Oncol, Apr. 2018, 13(2):157-173.

Sawa-Wejksza et al., "Tumor-Associated Macrophages as Target for Antitumor Therapy," Arch Immunol Ther Exp (Warsz), Apr. 2018, 66(2):97-111.

U.S. Appl. No. 18/411,372, Kakehi et al., filed Jan. 12, 2024.

U.S. Appl. No. 18/330,420, Kakehi et al., filed Jun. 7, 2023.

U.S. Appl. No. 18/340,168, Matsuoka et al., filed Jun. 23, 2023.

U.S. Appl. No. 16/756,404, Fujimoto et al., filed Apr. 15, 2020.

U.S. Appl. No. 16/983,115, Kakehi et al., filed Aug. 3, 2020.

U.S. Appl. No. 18/712,917, Ozawa et al., filed May 23, 2024.

U.S. Appl. No. 18/729,273, Ozawa et al., filed Jul. 16, 2024.

Yoshida et al., "Anti-interleukin-6 receptor antibody prevents loss of bone structure and bone strength in collagen-induced arthritis mice," Scand J Rheumatol, Sep. 2018, 47(5):384-391.

U.S. Appl. No. 12/094,644, Nakashima et al., filed Feb. 27, 2009 (abandoned).

U.S. Appl. No. 12/680,112, Igawa et al., filed Jun. 23, 2010 (abandoned).

U.S. Appl. No. 13/959,489, Igawa et al., filed Aug. 5, 2013 (abandoned).

U.S. Appl. No. 15/263,617, Igawa et al., filed Sep. 13, 2016 (abandoned).

U.S. Appl. No. 16/041,976, Igawa et al., filed Jul. 23, 2018 (abandoned).

U.S. Appl. No. 17/097,298, Igawa et al., filed Nov. 13, 2020.

U.S. Appl. No. 13/524,528, Igawa et al., filed Jun. 15, 2012 (abandoned).

U.S. Appl. No. 16/838,415, Igawa et al., filed Apr. 2, 2020 (abandoned).

U.S. Appl. No. 17/509,128, Igawa et al., filed Oct. 25, 2021.

U.S. Appl. No. 17/437,448, Takeshita et al., filed Sep. 9, 2021.

U.S. Appl. No. 13/387,292, Maeda, filed Apr. 3, 2012 (abandoned).

U.S. Appl. No. 15/877,894, Maeda, filed Jan. 23, 2018.

U.S. Appl. No. 16/609,053, Matsuoka et al., filed Oct. 28, 2019.

U.S. Appl. No. 16/963,311, Kato, filed Jul. 20, 2020.

U.S. Appl. No. 16/609,053, Matsuoka et al., filed Dec. 28, 2019.

U.S. Appl. No. 16/838,415, Igawa et al., filed Apr. 2, 2020.

ACTEMRA (tocilizumab), Highlights of Prescribing Information, as revised in Aug. 2017, 1 page.

Abdalla et al., "Current Challenges of Cancer Anti-angiogenic Therapy and the Promise of Nanotherapeutics," Theranostics, Jan. 1, 2018, 8(2):533-548. doi: 10.7150/thno.21674. eCollection 2018.

Akira et al., "Interleukin-6 in Biology and Medicine," Adv Immunol, 1993, 54:1-78.

Almand et al., "Clinical Significance of Defective Dendritic Cell Differentiation in Cancer," Clin Cancer Res, May 2000, 6(5):1755-66.

Almand et al., "Increased Production of Immature Myeloid Cells in Cancer Patients: A Mechanism of Immunosuppression in Cancer," J Immunol, Jan. 1, 2001, 166(1):678-89.

Ando et al., "Tocilizumab, a Proposed Therapy for the Cachexia of Interleukin6-Expressing Lung Cancer," PLOS One, Jul. 10, 2014, 9(7):e102436. doi: 10.1371/journal.pone.0102436. eCollection 2014.

Annual Report 2012 (Integrated Edition including CSR Report), Chugai Pharmaceutical Co. Ltd., Mar. 27, 2013.

"Interleukin 6-wikipedia", Feb. 22, 2019, XP055598802, Retrieved from the Internet Jun. 24, 2019: URL:https://protect-us.mimecast.com/s/6UxpCmZ28nsAp18JnGhTki?domain=en.wikipedia.org.

Araki et al., "Clinical Improvement in a Patient with Neuromyelitis Optica following Therapy with the Anti-IL-6 Receptor Monoclonal Antibody Tocilizumab," Mod Rheumatol, 2013, 23:827-831.

Araki et al., "Emerging Disease-modifying Therapies for Neuromyelitis Optica Spectrum Disorder," The medical frontline, 2016, 71(6):1159-1167 (with English translation).

Araki et al., "Efficacy of the anti-IL-6 receptor antibody tocilizumab in neuromyelitis optica—A pilot study," Neurology, Apr. 15, 2014, 82(15):1302-1306. doi: 10.1212/WNL.0000000000000317. Epub Mar. 14, 2014.

Aricha et al., "Blocking of IL-6 Suppresses Experimental Autoimmune Myasthenia Gravis," J Autoimmun, Mar. 2011, 36:135-141.

Arima et al., "Regional Neural Activation Defines a Gateway for Autoreactive T Cells to Cross the Blood-Brain Barrier," Cell, Feb. 3, 2012, 148(3):447-457.

Armour et al., "Recombinant human IgG molecules lacking Fcγ receptor I binding and monocyte triggering activities," Eur J Immunol, Aug. 1999, 29(8):2613-2624.

Audenet et al., "The evolution of bladder cancer genomics: What have we learned and how can we use it?", Urol Oncol, Jul. 2018, 36(7):313-320.

Balint et al., "Alterations of the peripheral B cell compartment in paediatric-onset multiple sclerosis," Journal of Neurology, May 2011, vol. 258, Suppl 1, pp. S202, Abstract No. P732.

Barkhof et al., "Comparison of MRI criteria at first presentation to predict conversion to clinically definite multiple sclerosis," Brain, Nov. 1997, 120(Pt 11):2059-2069.

Bartelds et al., "Clinical response to adalimumab: relationship to anti-adalimumab antibodies and serum adalimumab concentrations in rheumatoid arthritis," Ann Rheum Dis, Jul. 2007, 66(7):921-926. Epub Feb. 14, 2007.

Bender et al., "Immunogenicity, efficacy and adverse events of adalimumab in RA patients," Rheumatol Int, Jan. 2007, 27(3):269-274. Epub Sep. 28, 2006.

Besada, "Potential patient benefit of a subcutaneous formulation of a tocilizumab for the treatment of rheumatoid arthritis: a critical review," Patient Preference and Adherence, Aug. 1, 2014, 8:1051-1059. doi: 10.2147/PPA. S34958. eCollection 2014.

Bonapace et al., "Cessation of CCL2 inhibition accelerates breast cancer metastasis by promoting angiogenesis," Nature, Nov. 6, 2014, 515(7525):130-133.

Brown et al., "Tolerance to Single, but Not Multiple, Amino Acid Replacements in Antibody $V_H$ CDR2," J Immunol, May 1, 1996, 156(9):3285-3291.

(56) References Cited

OTHER PUBLICATIONS

Chau et al., "HuM291 (Nuvion), A Humanized Fc Receptor-Nonbinding Antibody Against CD3, Anergizes Peripheral Blood T Cells as Partial Agonist of the T Cell Receptor," Transplantation, Apr. 15, 2001, 71(7):941-950.

Chien et al., "Significant structural and functional change of an antigen-binding site by a distant amino acid substitution: Proposal of a structural mechanism," Proc Natl Acad Sci USA, Jul. 1989, 86(14):5532-5536.

Chihara et al., "Autoantibody producing cells in neuromyelitis optica," Journal of Clinical and Experimental Medicine, Feb. 11, 2012, 240:534-535 (with English translation).

Chihara et al., "Interleukin 6 signaling promotes anti-aquaporin 4 autoantibody production from plasmablasts in neuromyelitis optica," Proc Natl Acad Sci USA, Mar. 1, 2011, 108(9):3701-3706. doi:10.1073/pnas.1017385108. Epub Feb. 14, 2011.

Chirino et al., "Minimizing the immunogenicity of protein therapeutics," Drug Discov Today, Jan. 15, 2004, 9(2):82-90.

Choy, "Inhibiting Interleukin-6 in Rheumatoid Arthritis," Curr Rheumatol Rep, Oct. 2008, 10(5):413-417.

Christensen et al., "Systemic Inflammation in Progressive Multiple Sclerosis Involves Follicular T-Helper, Th17- and Activated B-Cells and Correlates with Progression," PLoS One, Mar. 2013, 8(3):e57820. doi:10.1371/journal.pone.0057820. Epub Mar. 1, 2013.

Chu et al., "Accumulation of Succinimide in a Recombinant Monoclonal Antibody in Mildly Acidic Buffers Under Elevated Temperatures," Pharm Res, Jun. 2007, 24(6):1145-1156. Epub Mar. 24, 2007.

Chugai NMO Clinical Trial Webinar "Sakura Star Study," webinar dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf, 18 pages.

Chugai Pharmaceutical, "A phase I, multiple-dose study of SA237," Study JapicCTI-No. 121786; submitted to Clinicaltrials.jp on Jan. 31, 2014; downloaded from clinicaltrials.jp archive on Sep. 5, 2019 as https://www.clinicaltrials.jp/cti-user/trial/Show.jsp, 5 pages.

Chugai Pharmaceutical, "A phase I, multiple-dose study of SA237," Study JapicCTI-No. 121786; submitted to Clinicaltrials.jp on Jun. 19, 2012; downloaded from clinicaltrials.jp archive on Sep. 5, 2019 as https://www.clinicaltrials.jp/cti-user/trial/Show.jsp, 5 pages.

Chugai Pharmaceutical, "A phase I, multiple-dose study of SA237," Study JapicCTI-No. 121786; submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V_3=View#StudyPageTop, 6 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 1; submitted to ClinicalTrials.gov on Feb. 25, 2014; downloaded from ClinicalTrials. gov archive on Sep. 4, 2019 as https://clinicaltrials.gov/ct2/history/NCT02073279?V_1=View#StudyPageTop, 6 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.

(56) References Cited

OTHER PUBLICATIONS

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11-View#StudyPageTop, 10 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.

Chugai Seiyaku Kabushiki Kaisha, Presentation of the results of the phase III international clinical trial of Satralizumab in neuromyelitis optica spectrum disorder at the European Committee for Treatment and Research in Multiple Sclerosis (ECTRIMS), Oct. 15, 2018 (with English translation).

Cocco et al., "In Vitro Generation of Long-lived Human Plasma Cells," J Immunol, Dec. 15, 2012, 189(12):5773-5785. doi:10.4049/jimmunol.1103720. Epub Nov. 16, 2012.

Cole et al., "Human IgG2 Variants of Chimeric Anti-CD3 Are Nonmitogenic to T Cells," J Immunol, Oct. 1, 1997, 159(7):3613-3621.

Cordoba et al., "Non-enzymatic hinge region fragmentation of antibodies in solution," J Chromatogr B Analyt Technol Biomed Life Sci, Apr. 25, 2005, 818(2):115-121.

Costa et al., "Efficacy of tocilizumab in a patient with refractory psoriatic arthritis," Clin Rheumatol, Sep. 2014, 33(9):1355-1357. doi: 10.1007/s10067-014-2603-5. Epub Apr. 8, 2014.

Dall'acqua et al., "Protein Structure and Folding: Properties of Human IgG1s Engineered for Enhanced Binding to the Neonatal Fc Receptor (FcRn)," J Biol Chem, Aug. 18, 2006, 281(33):23514-23524. Epub Jun. 21, 2006.

Damschroder et al., "Framework shuffling of antibodies to reduce immunogenicity and manipulate functional and biophysical properties," Mol Immunol, Apr. 2007, 44(11):3049-3060. Epub Jan. 22, 2007.

Davies et al., "Affinity improvement of single antibody VH domains: residues in all three hypervariable regions affect antigen binding," Immunotechnology. Sep. 1996, 2(3):169-179.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-3084.

Dillon et al., "Structural and Functional Characterization of Disulfide Isoforms of the Human IgG2 Subclass," J Biol Chem, Jun. 6, 2008, 283(23):16206-16215. Epub Mar. 12, 2008.

Ewert et al., "Stability improvement of antibodies for extracellular and intracellular applications: CDR grafting to stable frameworks and structure-based framework engineering," Methods, Oct. 2004, 34(2):184-199.

F. Hoffmann-La Roche Ltd., "Efficacy and Safety Study of Satralizumab (SA237) as Add-on Therapy to Treat Participants With Neuromyelitis Optica (NMO) and NMO Spectrum Disorder (NMOSD)," Study NCT02028884, first posted on clinicaltrialsregister.eu on Jan. 7, 2014 and last updated on Apr. 13, 2021; downloaded from clinicaltrialsregister.eu archive on May 19, 2021, https://clinicaltrials.gov/ct2/show/NCT02028884.

F. Hoffmann-La Roche Ltd., "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, first posted on clinicaltrialsregister.eu on Feb. 27, 2014 and last updated on Mar. 24, 2021; downloaded from clinicaltrialsregister.eu archive on May 19, 2021, https://clinicaltrials.gov/ct2/show/study/NCT02073279?show_locs=Y#locn.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search/trial/2013-003752-21/DE, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 23, 2021, https://www.clinicaltrialsregister.eu/ctr-search/trial/2013-003752-21/DE, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctr-search/trial/2013-003752-21/HU, 6 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Hungary; submitted to clinicaltrialsregister.eu on Feb. 25, 2015; downloaded from clinicaltrialsregister.eu archive on Sep. 23, 2021, https://www.clinicaltrialsregister.eu/ctr-search/trial/2013-003752-21/HU, 6 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Italy; submitted to clinicaltrialsregister.eu on Feb. 6, 2014; downloaded from clinicaltrialsregister.eu archive on Sep. 23, 2021, https://www.clinicaltrialsregister.eu/ctr-search/trial/2013-003752-21/IT, 5 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.

F. Hoffmann-La Roche Ltd., "A multicenter, randomized, addition to baseline treatment, double-blind, placebo-controlled, Phase 3

(56) References Cited

OTHER PUBLICATIONS study to evaluate the efficacy and safety of Satralizumab (SA237) in patients with neuromyelitis optica (NMO) and NMO spectrum disorder (NMOSD)," Study EudraCT 2013-003752-21 in Poland; submitted to clinicaltrialsregister.eu on Jul. 4, 2014; downloaded from clinicaltrialsregister.eu archive on Sep. 23, 2021, https://www.clinicaltrialsregister.eu/ctr-search/trial/2013-003752-21/PL, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Spain; submitted to clinicaltrialsregister.eu on Mar. 11, 2015; downloaded from clinicaltrialsregister.eu archive on Sep. 23, 2021, https://www.clinicaltrialsregister.eu/ctr-search/trial/2013-003752-21/ES, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/GB, 6 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in the United Kingdom; submitted to clinicaltrialsregister.eu on Oct. 15, 2013; downloaded from clinicaltrialsregister.eu archive on Sep. 23, 2021, https://www.clinicaltrialsregister.eu/ctr-search/trial/2013-003752-21/GB, 6 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search/trial/2015-005431-41/HR, 6 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Dec. 3, 2021, https://www.clinicaltrialsregister.eu/ctr-search/trial/2015-005431-41/HR, 6 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.

Furuya et al., "Interleukin-6 as a Potential Therapeutic Target for Pulmonary Arterial Hypertension," Int J Rheumatol, Aug. 2010, 2010:720305. doi: 10.1155/2010/720305. Epub Aug. 2, 2010.

Gessner et al., "The IgG Fc receptor family," Ann Hematol, Jun. 1998, 76(6):231-248.

Ghetie et al., "Increasing the serum persistence of an IgG fragment by random mutagenesis," Nat Biotechnol, Jul. 1997, 15(7):637-640.

Guerne et al., "Synovium as a Source of Interleukin 6 In Vitro—Contribution to Local and Systemic Manifestations of Arthritis," J Clin Invest, Feb. 1989, 83(2):585-592.

Guyre et al., "Increased potency of Fc-receptor-targeted antigens," Cancer Immunol Immunother, Nov.-Dec. 1997, 45(3-4):146-148.

Hanes et al., "Picomolar affinity antibodies from a fully synthetic naive library selected and evolved by ribosome display," Nat Biotechnol, Dec. 2000, 18(12):1287-1292.

Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-923. doi: 10.1007/s00296-009-1075-4. Epub Jul. 29, 2009.

Hinton et al., "An Engineered Human IgG1 Antibody with Longer Serum Half-Life," J Immunol, Jan. 1, 2006, 176(1):346-356.

Hirano et al., "Excessive production of interleukin 6/B cell stimulatory factor-2 in rheumatoid arthritis," Eur J Immunol, Nov. 1988, 18(11):1797-1801.

Hirano et al., "Complementary DNA for a Novel Human Interleukin (BSF-2) that Induces B Lymphocytes to Produce Immunoglobulin," Nature, Nov. 1986, 324:73-76.

Hirata et al., "Characterization of IL-6 Receptor Expression by Monoclonal and Polyclonal Antibodies," J Immunol, Nov. 1, 1989, 143:2900-2906.

Hisanaga et al., "Neuro-Behcet disease and neuro-Sweet disease," Clinical Neurology, 2012, 52:1234-1236 (with English abstract).

Holt et al., "Domain antibodies: proteins for therapy," Trends Biotechnol, Nov. 2003, 21(11):484-490.

Honda et al., "Marginal zone B cells exacerbate endotoxic shock via interleukin-6 secretion induced by $Fc\alpha/\mu R$-coupled TLR4 signalling," Nat Commun, May 5, 2016, 7:11498. doi: 10.1038/ncomms11498.

Hosokawa et al., "The Response to Treatment with Interferon beta-1 b in Patients with Multiple Sclerosis," Shinkei Chiryo, 2008, 25:589-595 (with English translation).

Houssiau et al., "Interleukin-6 in Synovial Fluid and Serum of Patients with Rheumatoid Arthritis and Other Inflammatory Arthritides," Arthritis Rheum, Jun. 1988, 31(6):784-788.

Houzen et al., "Increased prevalence, incidence, and female predominance of multiple sclerosis in northern Japan," J Neurol Sci, Dec. 15, 2012, 323(1-2):117-122. doi:10.1016/j.jns.2012.08.032. Epub Sep. 17, 2012.

Huang et al., "A Monoclonal Anti-Human IL-6 Receptor Antibody Inhibits the Proliferation of Human Myeloma Cells," Hybridoma, Oct. 1993, 12:621-630.

Huizinga et al., "Sarilumab, a fully human monoclonal antibody against $IL-6R\alpha$ in patients with rheumatoid arthritis and an inadequate response to methotrexate: efficacy and safety results from the randomised Saril-Ra-Mobility Part A trial," Ann Rheum Dis, Sep. 2014, 73(9):1626-1634. doi: 10.1136/annrheumdis-2013-204405. Epub Dec. 2, 2013.

Hwang et al., "Use of human germline genes in a CDR homology-based approach to antibody humanization," Methods, May 2005, 36(1):35-42.

Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.

Iijima et al., "Tocilizumab improves systemic rheumatoid vasculitis with necrotizing crescentic glomerulonephritis," Mod Rheumatol, Jan. 2015, 25(1):138-142. doi: 10.3109/14397595.2013.874748. Epub Feb. 18, 2014.

Ishikawa et al., "DNA microarray analysis of SLE related genes that respond to IL-6 blockade with tocilizumab, an anti-IL-6 receptor monoclonal antibody," Annals of the Rheumatic Diseases, Jun. 24, 2006, 65 (suppl 2):474. SAT0079.

(56)        References Cited

OTHER PUBLICATIONS

Ito et al., "The His-probe method: effects of histidine residues introduced into the complementarity-determining regions of antibodies on antigen-antibody interactions at different pH values," FEBS Lett, Aug. 31, 1992, 309(1):85-88.

Jacob et al., "Detrimental role of granulocytecolony stimulating factor in neuromyelitis optica: clinical case and histological evidence," Mult Scler, Dec. 2012, 18(12):1801-1803. doi: 10.1177/1352458512443994. Epub Apr. 11, 2012.

Japanese Society of Neurological Therapeutics, "Standard Neurological Therapeutics: Neuromyelitis Optica (NMO)," Nov. 1, 2013, Shinkeichiryo, vol. 30, No. 6, pp. 777-794 (with English translation).

Jego et al., "Interleukin-6 is a growth factor for nonmalignant human plasmablasts," Blood, Mar. 15, 2001, 97(6):1817-1822.

Johnson et al., "Cation exchange—HPLC and mass spectrometry reveal C-terminal amidation of an IgG1 heavy chain," Anal Biochem, Jan. 1, 2007, 360(1):75-83. Epub Oct. 30, 2006.

Jones et al., "Identification and removal of a promiscuous CD4+ T cell epitope from the C1 domain of factor VIII," J Thromb Haemost. May 2005, 3(5):991-1000.

Jourdan et al., "An in vitro model of differentiation of memory B cells into plasmablasts and plasma cells including detailed phenotypic and molecular characterization," Blood, Dec. 10, 2009, 114(25):5173-5181. doi:10.1182/blood-2009-07-235960.

Kakuron, Section 9 "Opticospinal Multiple Sclerosis," Tahatsusei Kokasho Chiryo Guideline, 2010, pp. 104-109 (with English translation).

Kampan et al., "Immunotherapeutic Interleukin-6 or Interleukin-6 Receptor in Cancer: Challenges and Opportunities," Curr Med Chem, Nov. 1, 2018, 25(36):4785-4806.

Kim et al., "Antibody Engineering for the Development of Therapeutic Antibodies," Mol Cells, Aug. 31, 2005, 20(1):17-29.

Kishimoto, "Interleukin-6 and its Receptor in Autoimmunity," J Autoimmun, Apr. 1992, 5 Suppl A:123-132.

Kishimoto, "The biology of interleukin-6," Blood, Jul. 1989, 74(10):1-10.

Kobatake et al., "Kdm6a Deficiency Activates Inflammatory Pathways, Promotes M2 Macrophage Polarization, and Causes Bladder Cancer in Cooperation with p53 Dysfunction," Clin Cancer Res, Apr. 15, 2020, 26(8):2065-2079.

Kondo et al., "A case of overlap syndrome successfully treated with tocilizumab: a hopeful treatment strategy for refractory dermatomyositis," Rheumatology, Oct. 2014, 53(10):1907-1908. doi: 10.1093/rheumatology/keu234. Epub May 23, 2014.

Kotake et al., "Interleukin-6 and Soluble Interleukin-6 Receptors in the Synovial Fluids from Rheumatoid Arthritis Patients Are Responsible for Osteoclast-like Cell Formation," J Bone Miner Res, Jan. 1996, 11(1):88-95.

Krieckaert et al., "Immunogenicity of Biologic Therapies—We Need Tolerance," Nat Rev Rheumatol, Oct. 2010, 6:558-559. doi: 10.1038/nrrheum.2010.153.

Lechner et al., "Characterization of Cytokine-Induced Myeloid-Derived Suppressor Cells from Normal Human Peripheral Blood Mononuclear Cells," J Immunol, Aug. 15, 2010, 185(4):2273-2284. doi:0.4049/jimmunol.1000901. Epub Jul. 19, 2010.

Ler et al., "Loss of tumor suppressor KDM6A amplifies PRC2-regulated transcriptional repression in bladder cancer and can be targeted through inhibition of EZH2," Sci Transl Med, Feb. 22, 2017, (378):eaai8312, 13 pages.

Lotz et al., "B Cell Stimulating Factor 2/Interleukin 6 is a Costimulant for Human Thymocytes and T Lymphocytes," J Exp Med, Mar. 1988, 167:1253-1258.

Lucchinetti et al., "Heterogeneity of Multiple Sclerosis Lesions: Implications for the Pathogenesis of Demyelination," Ann Neurol, Jun. 2000, 47(6):707-717.

Maccallum et al., "Antibody-antigen Interactions: Contact Analysis and Binding Site Topography," J Mol Biol, Oct. 11, 1996, 262(5):732-745.

Madhok et al., "Serum interleukin 6 levels in rheumatoid arthritis: correlations with clinical and laboratory indices of disease activity," Ann Rheum Dis, Mar. 1993, 52(3):232-234.

Maini et al., "Double-Blind Randomized Controlled Clinical Trial of the Interleukin-6 Receptor Antagonist, Tocilizumab, in European Patients With Rheumatoid Arthritis Who Had an Incomplete Response to Methotrexate," Arthritis Rheum, Sep. 2006, 54(9):2817-2829.

Matsumoto et al., "Interleukin-10-Producing Plasmablasts Exert Regulatory Function in Autoimmune Inflammation," Immunity, Dec. 18, 2014, 41(6):1040-1051. doi:10.1016/j.immuni.2014.10.016. Epub Nov. 4, 2014.

Maynard et al., "Antibody Engineering," Annu Rev Biomed Eng, Aug. 2000, 2:339-376.

Mihara et al., "Tocilizumab inhibits signal transduction mediated by both mIL-6R and siL-6R, but not by the receptors of other members of IL-6 cytokine family," Int Immunopharmacol, Nov. 2005, 5(12):1731-1740.

Mihara et al., "Anti-Interleukin 6 Receptor Antibody Inhibits Murine AA Amyloidosis," J Rheumatol, Jun. 2004, 31(6):1132-1138.

Miller et al., "Differential diagnosis of suspected multiple sclerosis: a consensus approach," Mult Scler, Nov. 2008, 14(9):1157-1174. doi:10.1177/1352458508096878. Epub Sep. 19, 2008.

Mori et al., "Novel models of cancer-related anemia in mice inoculated with IL-6-producing tumor cells," Biomed Res, Feb. 2009, 30(1):47-51.

Motozawa et al., "Unique circumferential peripheral keratitis in relapsing polychondritis," Medicine, Oct. 2017, 96(41):e7951. doi: 10.1097/MD.0000000000007951.

Nakamura et al., "Clinical Features of Multiple Sclerosis with High Plasmablast Frequency in Peripheral Blood," Abstract for Poster Session, Multiple Sclerosis, Keystone Symposia on Molecular and Cellular Biology, Big Sky, Montana, distributed Jan. 11, 2013.

Nakamura et al., "Clinical Features of Multiple Sclerosis with High Plasmablast Frequency in Peripheral Blood," Abstract, Multiple Sclerosis, Keystone Symposia on Molecular and Cellular Biology, Big Sky, Montana, published online Dec. 11, 2012.

Nakamura et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, 2013, presented Jan. 14, 2013.

Nakamura et al., "Clinical Characteristics of Multiple Sclerosis with High Peripheral Blood Plasmablast Frequency," Meeting Abstract, 54th Annual Meeting of the Japanese Society of Neurology, Tokyo, Japan, 2013, published Apr. 30, 2013 (with English translation).

Nakamura et al., "Clinical Features of Multiple Sclerosis with High Plasmablast Frequency in Peripheral Blood," Poster Session, 54th Annual Meeting of the Japanese Society of Neurology, Tokyo, Japan, 2013, presented Jun. 1, 2013.

Nakamura et al., "IL-6-dependent Plasmablasts in Pathological Conditions of Relapsing-Remitting Multiple Sclerosis," Jpn J Clin Immunol, 2013, 36:345, W5-5 (with English translation).

Nakamura et al., "Plasmablast in the Pathology of Multiple Sclerosis," Jpn J Clin Immunol, 2015, 38(5):403-411 (with English summary).

Narazaki et al., "Therapeutic effect of tocilizumab on two patients with polymyositis," Rheumatology, Jul. 2011, 50(7):1344-1346. doi: 10.1093/rheumatology/ker152. Epub Apr. 22, 2011.

Nishimoto et al., "Clinical Studies in Patients With Castleman's Disease, Crohn's Disease, and Rheumatoid Arthritis in Japan," Clin Rev Allergy Immunol, Jun. 2005, 28(3):221-230.

Nishimoto et al., "Interleukin 6: from bench to bedside," Nat Clin Pract Rheumatol, Nov. 2006, 2(11):619-626.

Nishimoto et al., "Expressions of immune response related genes were normalized after tocilizumab treatment in rheumatoid arthritis (RA) patients," Annals of the Rheumatic Diseases, 2013, 71 (suppl 3), 380, [FRI0198].

Nishimoto et al., "Humanized Anti-Interleukin-6 Receptor Antibody Treatment of Multicentric Castleman Disease," Blood, Oct. 15, 2005, 106:2627-2632.

Novick et al., "Monoclonal Antibodies to the Soluble Human IL-6 Receptor: Affinity Purification, ELISA, and Inhibition of Ligand Binding," Hybridoma, Feb. 1991, 10:137-146.

(56)            References Cited

OTHER PUBLICATIONS

Ohno et al., "Antigen-binding specificities of antibodies are primarily determined by seven residues of $V_H$," Proc Natl Acad Sci USA, May 1985, 82(9):2945-2949.

Ohsugi, "Current Antibody Drugs—Developments/Manufacturing Technology/Scope of Patents," Pharm Stage, 2007, 7(5):13-18 (with English translation).

Okabe, "Proprietary Innovative Antibody Engineering Technologies in Chugai Pharmaceutical," Information Meeting on Antibody Engineering Technologies, Dec. 18, 2012, 78 pages.

Okiyama et al., "Therapeutic Effects of Interleukin-6 Blockade in a Murine Model of Polymyositis That Does Not Require Interleukin-17A," Arthritis Rheum, Aug. 2009, 60(8):2505-2512.

Onda et al., "Lowering the Isoelectric Point of the Fv Portion of Recombinant Immunotoxins Leads to Decreased Nonspecific Animal Toxicity without Affecting Antitumor Activity," Cancer Res, Jul. 1, 2001, 61(13):5070-5077.

Padlan et al., "Structure of an antibody-antigen complex: Crystal structure of the HyHEL-10 Fab-lysozyme complex," Proc Natl Acad Sci USA, Aug. 1989, 86(15):5938-5942.

Paul, Chapter 26 "Chemokines," Fundamental Immunology, 5th ed., 2003, pp. 801-840.

Pavlou et al., "The therapeutic antibodies market to 2008," Eur J Pharm Biopharm, Apr. 2005, 59(3):389-396.

Perez-Sanchez et al., "Diagnostic potential of NETosis-derived products for disease activity, atherosclerosis and therapeutic effectiveness in rheumatoid arthritis," J Autoimmun, Aug. 2017, 82:31-40. doi: 10.1016/j.jaut.2017.04.007. Epub Apr. 29, 2017.

Pini et al., "Design and Use of a Phage Display Library—Human Antibodies with Subnonomolar Affinity Against a Marker of Angiogenesis Eluted from a Two-Dimensional Gel," J Biol Chem, Aug. 21, 1998, 273(34):21769-21776.

Polman et al., "Diagnostic Criteria for Multiple Sclerosis: 2010 Revisions to the McDonald Criteria," Ann Neurol, Jan. 11, 2011, 69:292-302.

Rajpal et al., "A general method for greatly improving the affinity of antibodies by using combinatorial libraries," Proc Natl Acad Sci USA, Jun. 14, 2005, 102(24):8466-8471. Epub Jun. 6, 2005.

Reddy et al., "Elimination of Fc Receptor-Dependent Effector Functions of a Modified IgG4 Monoclonal Antibody to Human CD4," J Immunol, Feb. 15, 2000, 164(4):1925-1933.

Reichert, "Antibodies to Watch in 2014," mAbs, Jul.-Aug. 2014, 6:799-802. doi: 10.4161/mabs.29282. Epub May 19, 2014.

Reichert et al., "Monoclonal antibody successes in the clinic," Nat Biotechnol, Sep. 2005, 23(9):1073-1078.

Roitt et al., Immunology, M., Mir, 2000, p. 110.

Rothe et al., "Ribosome display for improved biotherapeutic molecules," Expert Opin Biol Ther, Feb. 2006, 6(2):177-187.

Rudikoff et al., "Single amino acid substitution altering antigen-binding specificity," Proc Natl Acad Sci USA, Mar. 1982, 79(6):1979-1983.

Ruiz-Limon et al., "Tocilizumab improves the proatherothrombotic profile of rheumatoid arthritis patients modulating endothelial dysfunction, NETosis, and inflammation," Transl Res, May 2017, 183:87-103. doi: 10.1016/j.trsl.2016.12.003. Epub Dec. 9, 2016.

Saadoun et al., "Neutrophil protease inhibition reduces neuromyelitis optica-immunoglobulin G-induced damage in mouse brain," Ann Neurol, Mar. 2012, 71(3):323-333. doi: 10.1002/ana.22686. Epub Feb. 28, 2012.

Sack et al., "Interleukin-6 in synovial fluid is closely associated with chronic synovitis in rheumatoid arthritis," Rheumatol Int, Jun. 1993, 13(2):45-51.

Salfeld, "Isotype selection in antibody engineering," Nat Biotechnol, Dec. 2007, 25(12):1369-1372.

Sato et al., "Reshaping a Human Antibody to Inhibit the Interleukin 6-dependent Tumor Cell Growth," Cancer Res, Feb. 15, 1993, 53(4):851-856.

Sebba et al., "Tocilizumab: The first interleukin-6-receptor inhibitor," Am J Health Syst Pharm, Aug. 1, 2008, 65(15):1413-1418. doi: 10.2146/ajhp070449.

Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-9046. doi: 10.1073/pnas.0802218105. Epub Jun. 24, 2008.

Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-439. doi: 10.1007/s10165-011-0416-9. Epub Feb. 9, 2011.

Shimizu et al., "IFNβ-1b May Severely Exacerbate Japanese Optic-Spinal MS in Neuromyelitis Optica Spectrum," Neurology, Sep. 8, 2010, 75:1423-1427.

Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.

Shire et al., "Challenges in the Development of High Protein Concentration Formulations," J Pharm Sci, Jun. 2004, 93(6):1390-1402.

Silpa-Archa et al., "Outcome of tocilizumab treatment in refractory ocular inflammatory diseases," Acta Ophthalmol, Sep. 2016, 94(6):e400-e406. doi: 10.1111/aos.13015. Epub Mar. 24, 2016.

Srivastava et al., "Potassium Channel IGR.4.1 as an Immune Target in Multiple Sclerosis," N Engl J Med, Jul. 12, 2012, 367(2):115-123. doi:10.1056/NEJMoal110740.

Strand et al., "Biologic therapies in rheumatology: lessons learned, future directions," Nat Rev Drug Discov, Jan. 2007, 6(1):75-92.

Sumida et al., "Anti-IL-6 receptor mAb eliminates myeloid-derived suppressor cells and inhibits tumor growth by enhancing T-cell responses," Eur J Immunol, Aug. 2012, 42(8):2060-2072. doi: 10.1002/eji.201142335.

Suzuki et al., "Anti-murine IL-6 receptor antibody inhibits IL-6 effects in vivo," Immunol Lett, Sep. 1991, 30(1):17-21.

Taga et al., "Receptors for B Cell Stimulatory Factor 2," J Exp Med, Oct. 1, 1987, 166:967-981.

Taga et al., "Interleukin-6 Triggers the Association of its Receptor with a Possible Signal Transducer, gp130," Cell, Aug. 11, 1989, 58:573-581.

Takeshita et al., "The effect of NMO-IgG and anti-IL-6 receptor monoclonal antibody (SA237) for the Blood-Brain Barrier," abstract for presentation No. O-08-6, 60th Annual Meeting of the Japanese Society of Neurology, Feb. 18, 2019 <URL:http://www. neurology-jp.org/neuro2019/abstract/pdf/adoption_03.pdf> [retrieval date Apr. 20, 2020] (with English abstract).

Takeshita et al., "The effect of NMO-IgG and anti-IL-6 receptor monoclonal antibody (SA237) for the Blood-Brain Barrier," Rinsho Shinkeigaku, 2019, vol. 59, Supplement 224 O-08-6.

Takeshita et al., "Effects of neuromyelitis optica-IgG at the blood-brain barrier in vitro," Neurol Neuroimmunol Neuroinflamm, Dec. 19, 2016, 4(1):e311.

Takkinen et al., Chapter 38 "Affinity and Specificity Maturation by CDR Walking," Antibody Engineering, Springer Lab Manuals 2001, pp. 540-545.

Tamura et al., "Soluble interleukin-6 receptor triggers osteoclast formation by interleukin 6," Proc Natl Acad Sci USA, Dec. 15, 1993, 90(24):11924-11928.

Tan et al., "Engineering the isoelectric point of a renal cell carcinoma targeting antibody greatly enhances scFv solubility," Immunotechnology, Oct. 1998, 4(2):107-114.

Tanaka et al., "Therapeutic Targeting of the Interleukin-6 Receptor," Annu Rev Pharmacol Toxicol, 2012, 52:199-219. doi: 10.1146/annurev-pharmtox-010611-134715. Epub Sep. 9, 2011.

Teeling et al., "The Biological Activity of Human CD20 Monoclonal Antibodies Is Linked to Unique Epitopes on CD20," J Immunol, Jul. 1, 2006, 177(1):362-371.

Tintore et al., "Isolated Demyelinating Syndromes: Comparison of Different MR Imaging Criteria to Predict Conversion to Clinically Definite Multiple Sclerosis," Am J Neuroradiol, Apr. 2000, 21(4):702-706.

Uchida et al., "Increased cerebrospinal fluid metalloproteinase-2 and interleukin-6 are associated with albumin quotient in neuromyelitis optica: Their possible role on blood-brain barrier disruption," Mult Scler, Jul. 2017, 23(8): 1072-1084.

(56) References Cited

OTHER PUBLICATIONS

Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-428.

Van Der Meulen et al., "The H3K27me3 demethylase UTX in normal development and disease," Epigenetics, May 2014, 9(5):658-668.

Van Haaften et al., "Somatic mutations of the histone H3K27 demethylase gene *UTX* in human cancer," Nat Genet, May 2009, 41(5):521-523.

Van Walle et al., "Immunogenicity screening in protein drug development," Expert Opin Biol Ther, Mar. 2007, 7(3):405-418.

Waubant et al., "Clinical Characteristics of Responders to Interferon Therapy for Relapsing MS," Neurology, Jul. 21, 2003, 61:184-189.

Wang et al., "UTX Mutations in Human Cancer," Cancer Cell, Feb. 11, 2019, 35(2):168-176.

Weber, "Why does cancer therapy lack effective anti-metastasis drugs?," Cancer Lett, Jan. 28, 2013, 328(2):207-211. doi: 10.1016/j.canlet.2012.09.025. Epub Oct. 8, 2012.

Wingerchuk et al., "Revised diagnostic criteria for neuromyelitis optica," Neurology, May 22, 2006, 66:1485-1489.

Wingerchuk et al., "International consensus diagnostic criteria for neuromyelitis optica spectrum disorders," Neurology, Jul. 14, 2015, 85:177-189.

Wingerchuk et al., "The spectrum of neuromyelitis optica," Lancet Neurol, Sep. 2007, 6(9):805-815.

Wu et al., "Humanization of a Murine Monoclonal Antibody by Simultaneous Optimization of Framework and CDR Residues," J Mol Biol, Nov. 19, 1999, 294(1):151-162.

Wu et al., "Development of Motavizumab, an Ultra-potent Antibody for the Prevention of Respiratory Syncytial Virus Infection in the Upper and Lower Respiratory Tract," J Mol Biol, May 4, 2007, 368(3):652-665. Epub Feb. 20, 2007.

Wu et al., "Predictive Value of CD44 in Muscle-Invasive Bladder Cancer and Its Relationship with IL-6 Signaling," Ann Surg Oncol, Nov. 2018, 25(12):3518-3526.

Yamamura, "Anti-IL-6 receptor therapy for neuromyelitis optica," Neurological Therapeutics, Oct. 31, 2016, 33(5):S120 (with English translation).

Yamamura, "Anti-IL-6 receptor therapy for neuromyelitis optica," 34th Annual Meeting of Japanese Society of Neurological Therapeutics, Nov. 4, 2016 (with English translation).

Yamamura, "Treatment failures in NMO are due to specific immunologic mechanisms," 9th Annual International Roundtable Conference on NMO, Mar. 13, 2017.

Yamamura et al., "A double-blind placebo-controlled study of satralizumab (SA237), a recycling anti-IL-6 receptor monoclonal antibody, as add-on therapy for neuromyelitis optica (NMO) and NMO spectrum disorder (NMOSD)," European Journal of Neurology, 2018, 25 (Suppl. 2), p. 536, abstract EPR3103 for presentation given on Jun. 16, 2018). EPR3103 (https://ipp-ean18.netkey.at/index.php?p=recorddetail&rid=f16clff3-f5ec-4b71-8a99-7c39bdc90418&t)).

Yamasaki et al., "Cloning and Expression of the Human Interleukin-6 (BSF-2/IFNβ) Receptor," Science, Aug. 12, 1988, 241:825-828.

Yokota et al., "Clinical Study of Tocilizumab in Children With Systemic-Onset Juvenile Idiopathic Arthritis," Clin Rev Allergy Immunol, Jun. 2005, 28(3):231-238.

USPTO Restriction Requirement in U.S. Appl. No. 14/897,498, dated Dec. 18, 2017, 7 pages.

USPTO Non-Final Office Action in U.S. Appl. No. 14/897,498, dated Jun. 22, 2018, 16 pages.

USPTO Final Office Action in U.S. Appl. No. 14/897,498, dated Jan. 30, 2019, 15 pages.

USPTO Non-Final Office Action in U.S. Appl. No. 14/897,498, dated Aug. 21, 2019, 10 pages.

International Search Report in International Application No. PCT/JP2020/016652, mailed Jun. 16, 2020, 3 pages.

International Preliminary Report on Patentability in International Application No. PCT/JP2020/016652, mailed Sep. 28, 2021, 7 pages.

Roca et al., "CCL2 and interleukin-6 promote survival of human CD11b+ peripheral blood mononuclear cells and induce M2-type macrophage polarization," J Biol Chem, Dec. 4, 2009, 284(49):34342-34354.

U.S. Appl. No. 18/633,674, Igawa et al., filed Apr. 12, 2024.

U.S. Appl. No. 18/651,896, Igawa et al., filed May 1, 2024.

U.S. Appl. No. 17/829,641, Igawa et al., filed Jun. 1, 2022.

U.S. Appl. No. 18/280,970, Ozawa et al., filed Sep. 8, 2023.

U.S. Appl. No. 18/464,407, Igawa et al., filed Sep. 11, 2023.

U.S. Appl. No. 18/478,148, Maeda, filed Sep. 29, 2023.

* cited by examiner

A

B

A

B

THERAPEUTIC AGENT FOR UROLOGICAL CANCER WHICH IS CHARACTERIZED BY BEING ADMINISTERED WITH IL-6 INHIBITOR AND CCR2 INHIBITOR IN COMBINATION

CROSS-REFERENCE TO RELATED APPLICATIONS

This application is the National Stage of International Application No. PCT/JP2020/016652, filed Apr. 16, 2020, which claims the benefit of Japanese Application No. 2019-078928, filed Apr. 17, 2019.

TECHNICAL FIELD

The present invention relates to therapeutic agents for urologic cancers, particularly urologic cancers with reduced lysine (K)-specific demethylase 6A (KDM6A) function, the agents being characterized in that an IL-6 inhibitor and a CCR2 inhibitor are administered in combination.

BACKGROUND ART

Bladder cancer is a malignant tumor of urothelial cells, and its incidence is increasing with the aging of the population. Early superficial cancer can be treated by transurethral resection of the bladder tumor, but this is characterized by being prone to recurrence. In addition, the prognosis of advanced muscle invasive cancer and metastatic cases has not been improved, and there is a demand for new treatment methods based on molecular pathology.

UTX (ubiquitously transcribed tetratricopeptide repeat X chromosome, also known as lysine (K)-specific demethylase 6A (KDM6A)) is a demethylase for histone H3K27, and its loss-of-function mutations have been reported in various human tumors (NPL 1). Among the mutations, bladder cancer is the most common, prostate cancer and penile cancer are also high in proportion, and UTX function deficiency is considered to be deeply involved in tumor onset in urology area (NPL 2 and NPL 3).

As for article showing the involvement of Utx in the onset of bladder cancer, there is a report of an experimental model of transplantation into immunodeficient mice using a human bladder cancer cell line carrying an Utx mutation (NPL 4); however, this is the result of performing xenotransplantation using cultured cells, and it is difficult to say that it is a model reflecting Utx function deficiency in vivo. So far, studies focusing on bladder cancer and performing production and analyses of bladder-specific Utx-deficient (Utx$^{\Delta/\Delta}$) mice by using a genetic modification technique have not been reported.

IL-6 is a cytokine also referred to as B cell stimulating factor 2 (BSF2) or interferon (β2. It was discovered as a differentiation factor involved in the activation of B lymphoid cells (NPL 5), and was later revealed to be a multifunctional cytokine that affects the functions of various cells (NPL 6). IL-6 has been reported to induce maturation of T lymphoid cells (NPL 7).

CCL2 is a chemokine related to innate immunity, Th2 effector response, CD4+ T cell differentiation, and such, and is also referred to as CC-chemokine ligand 2, monocyte chemotactic protein 1, and MCP-1 (NPL 8). CCR2 is known as a receptor for CCL2.

So far, it has been reported that blocking of IL-6 in vitro in the sphere-forming cells (sMB49), which were obtained after suspension-culturing of mouse bladder cancer MB49 cells, caused reduction in the infiltration ability of the sphere-forming MB49 cells (NPL 9).

In addition, it has been reported that administering an anti-IL-6 antibody and an anti-CCL2 antibody to mice with invasive breast cancer resulted in suppressed cancer infiltration and extended survival time (NPL 10).

However, the therapeutic effect of the combination use of an IL-6 inhibitor and a CCR2 inhibitor on bladder cancer has not been reported.

CITATION LIST

Non-Patent Literature

[NPL 1] van Haaften et al. Nature Genetics, volume 41, number 5, 2009
[NPL 2] Van der Meulen et al. Epigenetics, volume 9, Issue 5, 2014
[NPL 3] Lu Wang, et al., UTX mutation in Human Cancer. Cancer Cell, 2019
[NPL 4] Ler et al, Science Translational Medicine, 9, eaai8321 (2017)
[NPL 5] Hirano, T. et al., Nature (1986) 324, 73-76
[NPL 6] Akira, S. et al., Adv. in Immunology (1993) 54, 1-78
[NPL 7] Lotz, M. et al., J. Exp. Med. (1988) 167, 1253-1258
[NPL 8] Paul, W. E., Fundamental Immunology, 5th Edition, Lippincott Williams & Wilkins, (Philadelphia, 2003) p. 801-840
[NPL 9] Annals of Surgical Oncology, November 2018, vol. 25, Issue 12, pp 3518-3526
[NPL 10] Nature, Vol. 515, 6, 2014, 130-133

SUMMARY OF INVENTION

Technical Problem

The present invention was achieved in view of the above circumstances. An objective of the present invention is to provide novel therapeutic agents for urologic cancers.

Solution to Problem

The present inventors conducted dedicated research to solve the above-mentioned problems. As a result, the present inventors found that for urologic cancers, particularly urologic cancers with reduced lysine (K)-specific demethylase 6A (KDM6A) function, tumor growth can be significantly inhibited by suppressing both CCL2/CCR2 activity and IL-6 activity.

The present invention is based on such findings, and specifically includes the following.

[1] A therapeutic and/or prophylactic agent for urologic cancer comprising an IL-6 inhibitor, wherein the agent is for administration in combination with a CCR2 inhibitor.

[2] A therapeutic and/or prophylactic agent for urologic cancer comprising a CCR2 inhibitor, wherein the agent is for administration in combination with an IL-6 inhibitor.

[3] A therapeutic and/or prophylactic agent for urologic cancer, comprising a combination of an IL-6 inhibitor and a CCR2 inhibitor.

[4] The therapeutic and/or prophylactic agent of any one of [1] to [3], wherein the IL-6 inhibitor is an anti-IL-6 antibody or an anti-IL-6 receptor antibody.

[5] The therapeutic and/or prophylactic agent of [4], wherein the anti-IL-6 antibody and the anti-IL-6 receptor antibody are chimeric antibodies, humanized antibodies, or human antibodies.

[6] The therapeutic and/or prophylactic agent of any one of [1] to [5], wherein the CCR2 inhibitor is a CCL2 inhibitor.

[7] The therapeutic and/or prophylactic agent of any one of [1] to [6], wherein the CCR2 inhibitor is an anti-CCL2 antibody or a propagermanium.

[8] The therapeutic and/or prophylactic agent of [7], wherein the CCL2 antibody is a chimeric antibody, a humanized antibody, or a human antibody.

[9] The therapeutic and/or prophylactic agent of any one of [1] to [8], wherein the cancer is bladder cancer, prostate cancer, or kidney cancer.

[10] The therapeutic and/or prophylactic agent of any one of [1] to [9], wherein the cancer is bladder cancer.

[11] The therapeutic and/or prophylactic agent of any one of [1] to [10], wherein the cancer is a cancer with reduced lysine (K)-specific demethylase 6A (KDM6A) expression or function.

[12] The therapeutic and/or prophylactic agent of any one of [1] to [11], wherein the cancer is a cancer having a mutation in the KDM6A gene.

[13] The therapeutic and/or prophylactic agent of [12], wherein the mutation in the KDM6A gene is a loss-of-function mutation.

[14] The therapeutic and/or prophylactic agent of any one of [1] to [13], wherein the cancer is a cancer with reduced p53 expression or function.

[15] The therapeutic and/or prophylactic agent of any one of [1] to [14], wherein the cancer is a cancer having a mutation in the p53 gene.

[16] The therapeutic and/or prophylactic agent of any one of [1] to [10], which is for administration to an individual determined to have reduced KDM6A function, reduced KDM6A expression, and/or a KDM6A gene mutation.

[17] The therapeutic and/or prophylactic agent of any one of [1] to [10] and [16], which is for administration to an individual determined to have reduced p53 expression, reduced p53 function, and/or a p53 gene mutation.

The present invention further comprises the following embodiments.

[18] An IL-6 inhibitor for use in treatment and/or prevention of urologic cancer in combination with a CCR2 inhibitor.

[19] A CCR2 inhibitor for use in treatment and/or prevention of urologic cancer in combination with an IL-6 inhibitor.

[20] A combination of an IL-6 inhibitor and a CCR2 inhibitor for use in treatment and/or prevention of urologic cancer.

[21] A method of treatment and/or prevention of urologic cancer, the method comprising administering an effective amount of an IL-6 inhibitor to an individual and administering an effective amount of a CCR2 inhibitor to the individual.

[22] A method of treatment and/or prevention of urologic cancer, the method comprising administering an effective amount of a combination of an IL-6 inhibitor and a CCR2 inhibitor to an individual.

[23] Use of an IL-6 inhibitor in the manufacture of a therapeutic and/or prophylactic agent for urologic cancer which is for administration in combination with a CCR2 inhibitor.

[24] Use of a CCR2 inhibitor in the manufacture of a therapeutic and/or prophylactic agent for urologic cancer which is for administration in combination with an IL-6 inhibitor.

[25] Use of a combination of an IL-6 inhibitor and a CCR2 inhibitor in the manufacture of a therapeutic and/or prophylactic agent for urologic cancer.

[26] The inhibitor, combination, method of treatment, method of prevention, or use of any one of [18] to [25], wherein the IL-6 inhibitor is an anti-IL-6 antibody or an anti-IL-6 receptor antibody.

[27] The inhibitor, combination, method of treatment, method of prevention, or use of [26], wherein the anti-IL-6 antibody and anti-IL-6 receptor antibody are chimeric antibodies, humanized antibodies, or human antibodies.

[28] The inhibitor, combination, method of treatment, method of prevention, or use of any one of [18] to [27], wherein the CCR2 inhibitor is a CCL2 inhibitor.

[29] The inhibitor, combination, method of treatment, method of prevention, or use of any one of [18] to [27], wherein the CCR2 inhibitor is an anti-CCL2 antibody or propagermanium.

[30] The inhibitor, combination, method of treatment, method of prevention, or use of [29], wherein the anti-CCL2 antibody is a chimeric antibody, humanized antibody, or a human antibody.

[31] The inhibitor, combination, method of treatment, method of prevention, or use of any one of [18] to [30], wherein the cancer is bladder cancer, prostate cancer, or kidney cancer.

[32] The inhibitor, combination, method of treatment, method of prevention, or use of any one of [18] to [31], wherein the cancer is bladder cancer.

[33] The inhibitor, combination, method of treatment, method of prevention, or use of any one of [18] to [32], wherein the cancer is a cancer with reduced lysine (K)-specific demethylase 6A (KDM6A) expression or function.

[34] The inhibitor, combination, method of treatment, method of prevention, or use of any one of [18] to [33], wherein the cancer is a cancer having a mutation in the KDM6A gene.

[35] The inhibitor, combination, method of treatment, method of prevention, or use of [34], wherein the mutation in the KDM6A gene is a loss-of-function mutation.

[36] The inhibitor, combination, method of treatment, method of prevention, or use of any one of [18] to [35], wherein the cancer is a cancer with reduced p53 expression or function.

[37] The inhibitor, combination, method of treatment, method of prevention, or use of any one of [18] to [36], wherein the cancer is a cancer having a genetic mutation in p53.

[38] The inhibitor, combination, method of treatment, method of prevention, or use of any one of [18] to [32], which is for administration to an individual determined to have reduced KDM6A function, reduced KDM6A expression, and/or a KDM6A gene mutation.

[39] The inhibitor, combination, method of treatment, method of prevention, or use of any one of [18] to [32] and [38], which is for administration to an individual determined to have reduced p53 expression, reduced p53 function, and/or a p53 gene mutation.

Effects of the Invention

The present invention provides novel therapeutic agents for urologic cancers.

Figure 1:
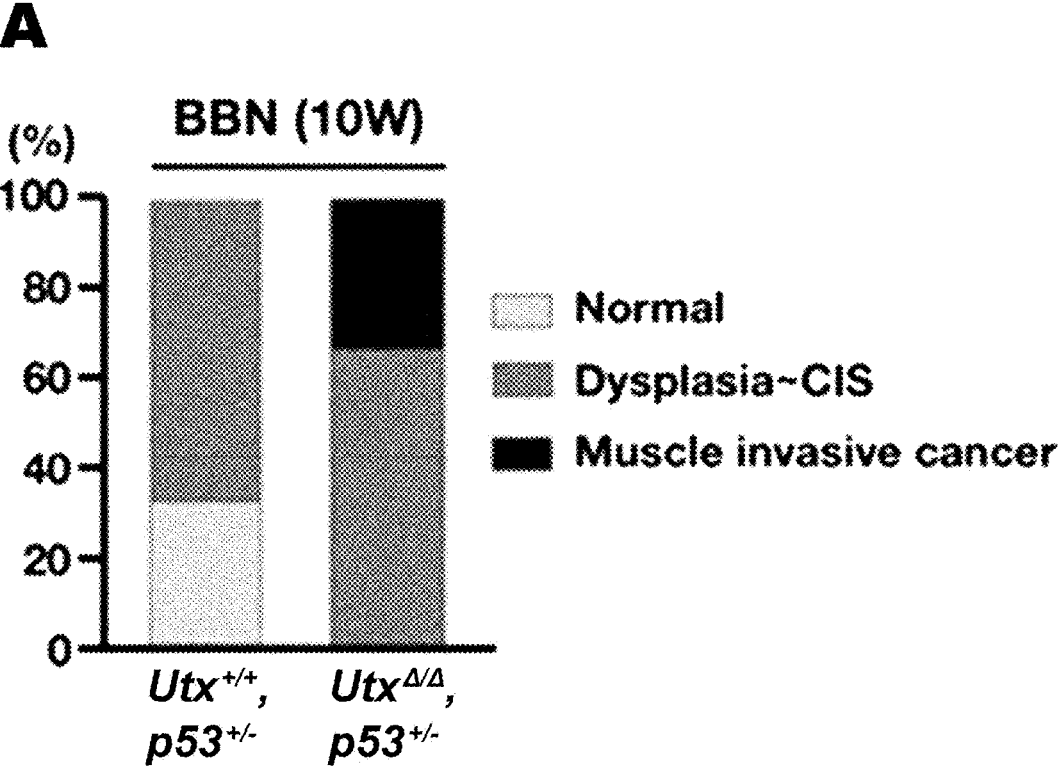
In FIG. 1, A shows the proportions of normal tissue (Normal), dysplasia to carcinoma in situ (Dysplasia~CIS), and cancer infiltrated into the muscle layer (Muscle invasive cancer) in the bladder of control mice (Utx$^{+/+}$, p53$^{+/-}$ mice)
Figure 1:
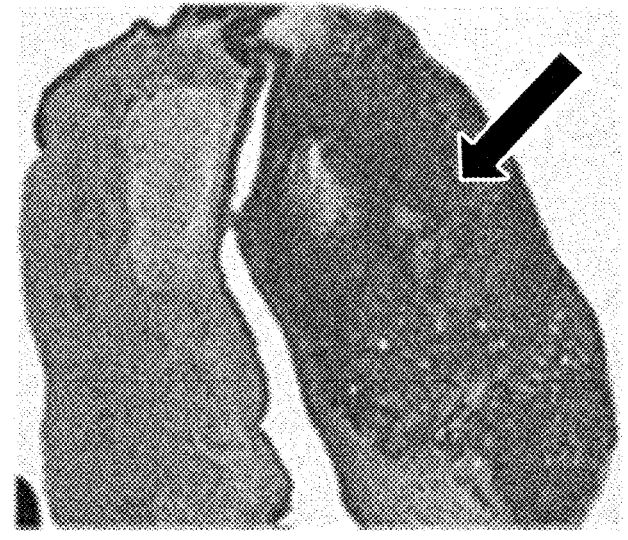

5 and Utx$^{\Delta/\Delta}$, p53$^{+/-}$ mice, ten weeks after administration of N-butyl-N-(4-hydro-oxybutyl) nitorosamine (BBN). B of FIG. 1 is a photograph showing the results of hematoxylin-eosin staining of tissue sections collected from the bladder of Utx$^{\Delta/\Delta}$, p53$^{+/-}$ mice to which BBN was administered. An arrow in the figure indicates cancer infiltrated into the muscle layer.

Figure 2:
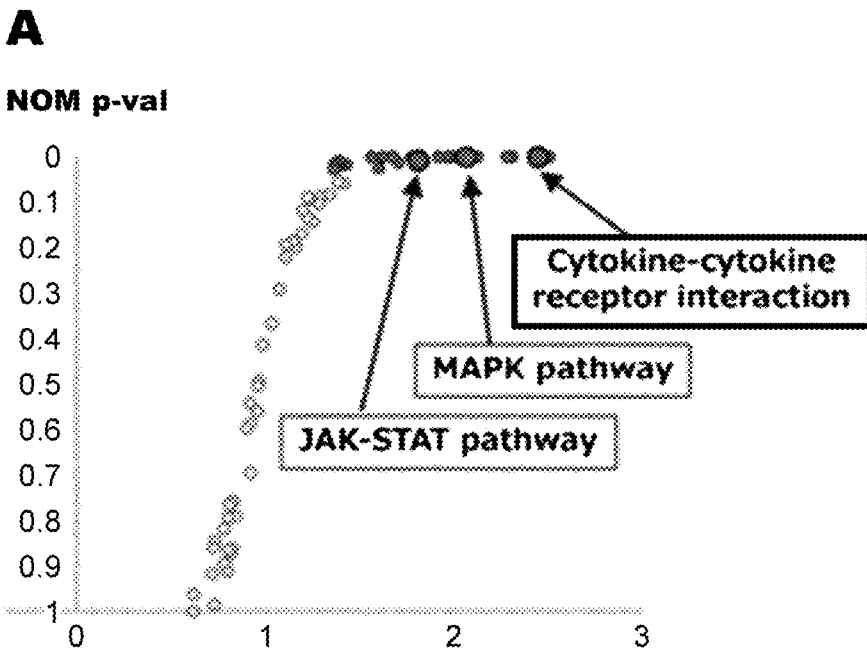
Figure 2:
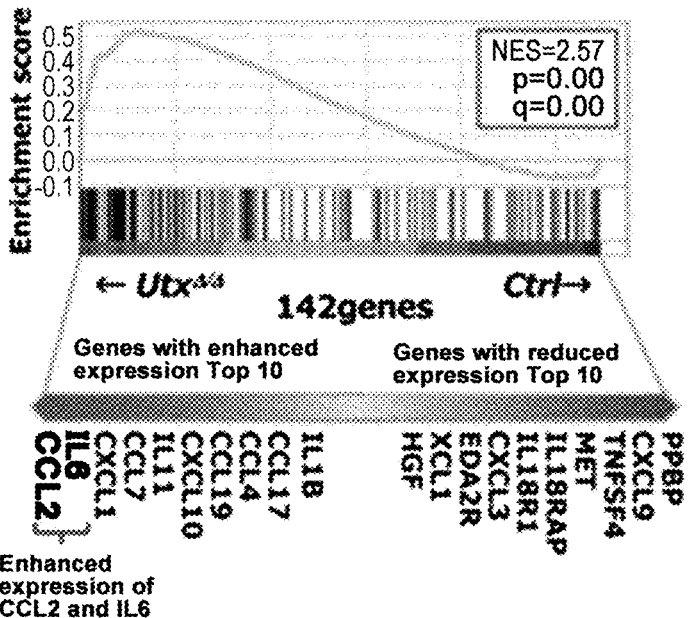

FIG. 2 shows the results of transcriptome analysis and pathway analysis by KEGG using RNAs extracted from the urothelium of control Utx$^{+/+}$ mice and Utx$^{\Delta/\Delta}$ mice at 4 weeks of BBN administration. In FIG. 2, A is a diagram of pathway comparison results between control mice and Utx$^{\Delta/\Delta}$ mice, where pathways showing enhanced expression in Utx$^{\Delta/\Delta}$ mice as compared to in the control mice are indicated. In FIG. 2, B shows the results of comparing the expression of 142 genes in the "cytokine-cytokine receptor interaction" pathway between control mice and Utx$^{4/4}$ mice.

Figure 3:
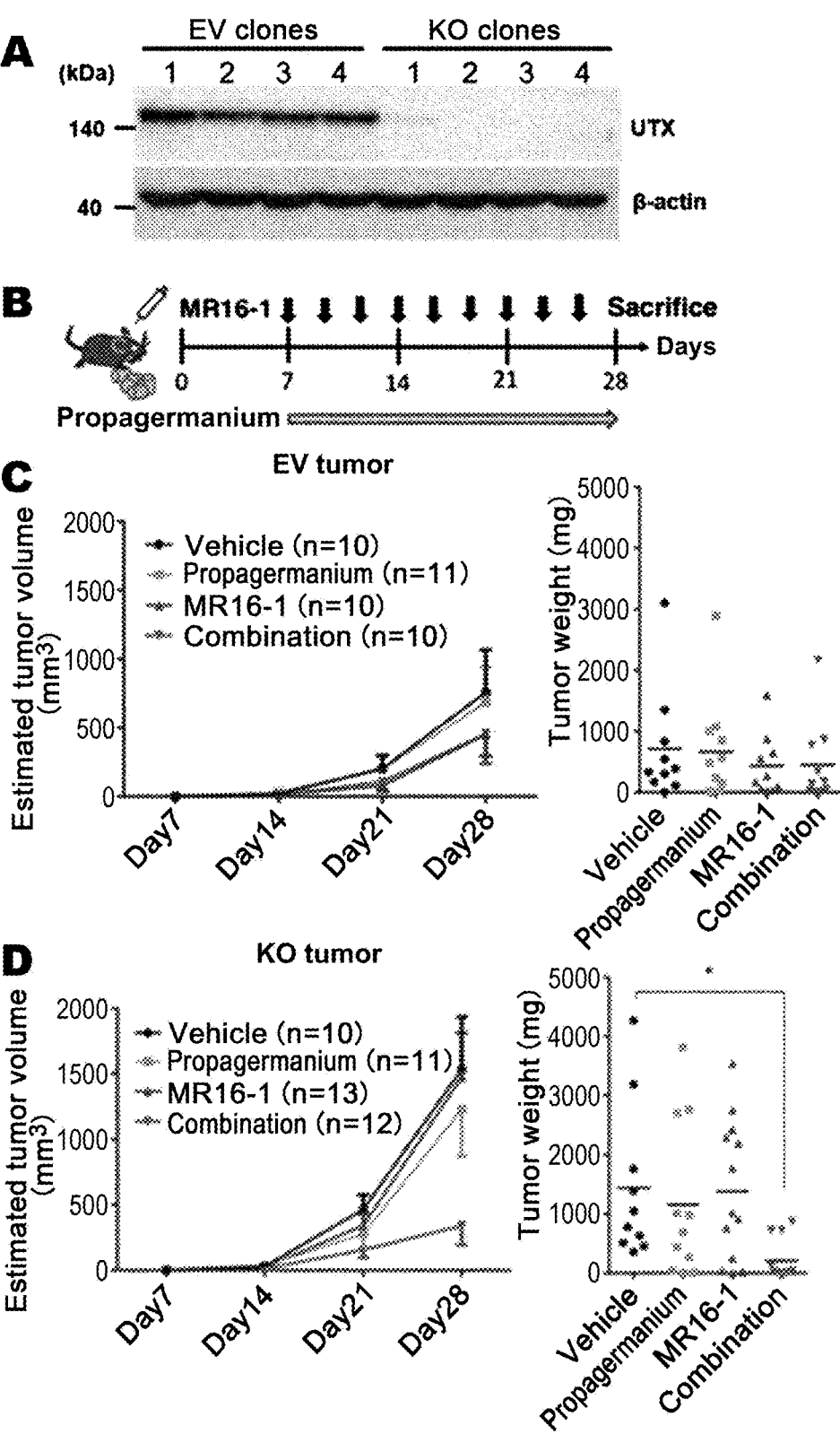

In FIG. 3, A is a photograph showing the results of analyzing the expression of UTX protein in the Utx-expressing strain (EV clones) and the Utx-deficient strain (KO clones) derived from mouse bladder cancer cell line MBT2 by Western blotting using an anti-UTX antibody or an anti-β-actin antibody. In FIG. 3, B is a diagram showing the administration schedule of propagermanium and/or MR16-1 in tumor-transplanted mice. C and D of FIG. 3 are diagrams showing the tumor volume (Estimated tumor volume) and tumor weight (Tumor weight) of a tumor resulting from transplantation of an Utx-expressing strain (C) or an Utx-deficient strain (D) into C3H mice.

DESCRIPTION OF EMBODIMENTS

A non-limiting aspect of the present invention provides therapeutic or prophylactic agents for urologic cancers (also expressed as pharmaceutical compositions for treating or preventing urologic cancers) and combination therapies for urologic cancers, the agents and therapies being characterized by suppressing both IL-6 activity and CCR2/CCL2 activity. In one embodiment of this aspect, the urologic cancer is bladder cancer, prostate cancer, kidney cancer, or penile cancer. In an embodiment of this aspect, the urologic cancer is a cancer with reduced expression of lysine (K)-specific demethylase 6A (KDM6A) or a cancer with reduced KDM6A function, and optionally, it is a cancer having a mutation (for example, a loss-of-function mutation) in the KDM6A gene. In one embodiment of this aspect, the urologic cancer is a urologic cancer having a mutation in p53. In an embodiment of this aspect, the combined use of an IL-6 inhibitor and a CCR2 inhibitor yields a synergistic effect in the treatment or prevention of urologic cancer, as compared to treatment with an IL-6 inhibitor or a CCR2 inhibitor alone.

In one embodiment of the above-mentioned aspect, provided is a therapeutic or prophylactic agent for urologic cancer for administration in combination with a CCR2 inhibitor, the agent comprising an IL-6 inhibitor as an active ingredient. In the embodiment, the therapeutic or prophylactic agent for urologic cancer comprising an IL-6 inhibitor is administered simultaneously with, separately from, or sequentially with a CCR2 inhibitor. The dosage forms of these inhibitors may be the same or different. For example, the two may have different dosage forms, each one of which is any one of a parenteral preparation, an injection, a drip, and an intravenous drip but not the same; alternatively, the two may have the same dosage form, which is any one of a parenteral preparation, an injection, a drip, and an intravenous drip. This embodiment can be expressed as an IL-6 inhibitor for use in treatment or prevention of urologic cancer in combination with a CCR2 inhibitor; a method of treatment or prevention of urologic cancer, the method comprising administering an IL-6 inhibitor and administering a CCR2 inhibitor; or use of an IL-6 inhibitor in the manufacture of a therapeutic or a prophylactic agent for urologic cancer for administration in combination with a CCR2 inhibitor.

In another embodiment of the above-mentioned aspect, provided is a therapeutic or prophylactic agent for urologic cancer for administration in combination with an IL-6 inhibitor, the agent comprising a CCR2 inhibitor as an active ingredient. In the embodiment, the therapeutic or prophylactic agent for urologic cancer comprising a CCR2 inhibitor is administered simultaneously with, separately from, or sequentially with an IL-6 inhibitor. The dosage forms of these inhibitors may be the same or different. For example, the two may have different dosage forms, each of which is any one of a parenteral preparation, an injection, a drip, and an intravenous drip but not the same; alternatively, the two may have the same dosage form, which is any one of a parenteral preparation, an injection, a drip, and an intravenous drip. This embodiment can be expressed as a CCR2 inhibitor for use in treatment or prevention of urologic cancer in combination with an IL-6 inhibitor; a method of treatment or prevention of urologic cancer, the method comprising administering an effective amount of an IL-6 inhibitor to an individual and administering an effective amount of a CCR2 inhibitor to an individual; or use of a CCR2 inhibitor in the manufacture of a therapeutic or a prophylactic agent for urologic cancer for administration in combination with an IL-6 inhibitor.

In other embodiments of the above-mentioned aspect, provided is a therapeutic or prophylactic agent for urologic cancer, the agent comprising a combination of an IL-6 inhibitor and a CCR2 inhibitor as active ingredients. This embodiment can be expressed as a combination of an IL-6 inhibitor and a CCR2 inhibitor for use in treatment or prevention of urologic cancer; a method of treatment or prevention of urologic cancer, the method comprising administering an effective amount of a combination of an IL-6 inhibitor and a CCR2 inhibitor to an individual; or use of a combination of an IL-6 inhibitor and a CCR2 inhibitor in the manufacture of a therapeutic or a prophylactic agent for urologic cancer.

"IL-6 inhibitors" of the present invention are substances that block signal transduction by IL-6, and inhibit the biological activities of IL-6. IL-6 inhibitors are preferably substances that have inhibitory effects against binding to any one of IL-6, IL-6 receptor, and gp130. Examples of an IL-6 inhibitor of the present invention include, but are not particularly limited to, anti-IL-6 antibodies, anti-IL-6 receptor antibodies, anti-gp130 antibodies, IL-6 variants, soluble IL-6 receptor variants, or partial peptides of IL-6 or IL-6 receptor, and low-molecular-weight substances showing a similar activity. Examples of an IL-6 inhibitor of the present invention may be preferably IL-6 receptor-recognizing antibodies.

IL-6 transmits its biological activity via two types of proteins on cells. One of them is the IL-6 receptor, which is a ligand-binding protein that has a molecular weight of approximately 80 kD to which IL-6 binds (NPLs 4 and 5). The IL-6 receptor exists as a soluble IL-6 receptor, which is mainly composed of its extracellular region, in addition to a membrane-bound form expressed on the cell membrane and penetrates through the cell membrane.

The other one is non-ligand-binding membrane protein gp130, which has a molecular weight of about 130 kDa and is involved in signal transduction. The biological activity of IL-6 is transmitted into a cell through formation of an IL-6/IL-6 receptor complex by IL-6 and the IL-6 receptor, followed by binding of the complex with gp130 (Taga, T. et al, Cell (1989) 58, 573-581).

"CCR2 inhibitors" in the present invention are substances that block signal transduction by CCL2, CCL7, or CCL8; inhibit the biological activities of CCL2, CCL7, and/or CCL8; and include CCL2 inhibitors, CCL7 inhibitors, and CCL8 inhibitors. The "CCL2 inhibitors" in the present invention are substances that block signal transduction by CCL2, and block the biological activities of CCL2.

Examples of an CCL2 inhibitor of the present invention include, but are not particularly limited to, anti-CCL2 antibodies, antibodies against CCR2 which is a receptor for CCL2 (anti-CCR2 antibodies), and low-molecular-weight substances that bind to CCR2 and block the signal transduction by CCL2. Examples of a CCL2 inhibitor of the present invention may be preferably anti-CCL2 antibodies and low-molecular-weight substances that bind to CCR2 and block the signal transduction by CCL2 (for example, propagermanium).

CCL2 is a chemokine related to innate immunity, Th2 effector response, CD4+ T cell differentiation, and such, and is also referred to as CC-chemokine ligand 2, monocyte chemotactic protein 1, and MCP-1 (Paul, W. E., Fundamental Immunology, 5$^{th}$ Edition, Lippincott Williams & Wilkins, (Philadelphia, 2003) p. 801-840). CCL2 is known to bind via chemokine receptor CCR2 and transduce signals. CCR2 is a 7-transmembrane G protein-coupled receptor expressed on numerous cells, including monocytes, T cells, B cells, and basophils.

The origin of the antibodies of the present invention is not particularly limited, but it is preferably a mammal and more preferably human.

An anti-IL-6 antibody, anti-IL-6 receptor antibody, anti-gp130 antibody, anti-CCL2 antibody, and anti-CCR2 antibody used in the present invention can be obtained as either a polyclonal or monoclonal antibody using known methods. A monoclonal antibody derived from a mammal is particularly preferred for the anti-IL-6 antibody, anti-IL-6 receptor antibody, anti-gp130 antibody, anti-CCL2 antibody, and anti-CCR2 antibody used in the present invention. The monoclonal antibodies derived from a mammal include those produced by a hybridoma and those produced by a host transformed with an expression vector containing an antibody gene using genetic engineering methods. By binding to IL-6, such an anti-IL-6 antibody inhibits the binding of IL-6 to an IL-6 receptor, and blocks transduction of the IL-6 biological activity into cells.

Examples of such an anti-IL-6 antibody include the MH166 antibody (Matsuda, T. et al., Eur. J. Immunol. (1988) 18, 951-956) and the SK2 antibody (Sato, K. et al., The abstracts of the 21st Annual Meeting of the Japanese Society for Immunology (1991) 21, 166). Production methods and such of an anti-IL-6 antibody, as an example of various antibodies to be used in the present invention, are described below. Basically, other antibodies can be produced using the same procedures and known techniques (an anti-CCL2 antibody can be also produced with reference to the teachings of Japanese Patent No. 9067399, JP-A (Kokai) H05276986, WO03048083, US20040047860, US20060039913, and WO2006/125202).

Basically, hybridomas that produce an anti-IL-6 antibody can be produced using known techniques as below. Specifically, the hybridomas can be produced by performing immunization by a conventional immunization method using IL-6 as a sensitizing antigen, fusing the resulting immune cells with known parent cells by a conventional cell fusion method, and then screening for cells that produce monoclonal antibodies using a conventional screening method.

Specifically, anti-IL-6 antibodies can be produced as below. Human IL-6 to be used as a sensitizing antigen for obtaining antibodies can be obtained by, for example, using the IL-6 gene/amino acid sequences disclosed in Eur. J. Biochem. (1987) 168, 543-550; J. Immunol. (1988) 140, 1534-1541; and Agr. Biol. Chem. (1990) 54, 2685-2688.

After an appropriate host cell is transformed with a known expression vector system inserted with an IL-6 gene sequence, the target IL-6 protein is purified from the inside of the host cell or from the culture supernatant using a known method. This purified IL-6 protein may be used as a sensitizing antigen. Alternatively, a fusion protein of the IL-6 protein and another protein may be used as a sensitizing antigen.

An anti-IL-6 receptor antibody used in the present invention can be obtained as either a polyclonal or monoclonal antibody using known methods. A monoclonal antibody derived from a mammal is particularly preferred for the anti-IL-6 receptor antibody used in the present invention. The monoclonal antibodies derived from a mammal include those produced by a hybridoma and those produced by a host transformed with an expression vector containing an antibody gene using genetic engineering methods. By binding to an IL-6 receptor, this antibody inhibits the binding of IL-6 to an IL-6 receptor, and blocks transduction of the IL-6 biological activity into cells.

Examples of such an antibody include the MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (International Patent Application Publication No. WO 92-19759). Among them, the PM-1 antibody is listed as an example of a preferred monoclonal antibody against the human IL-6 receptor, and the MR16-1 antibody is listed as an example of a preferred monoclonal antibody against the mouse IL-6 receptor.

Basically, hybridomas that produce an anti-IL-6 receptor monoclonal antibody can be produced using known techniques as below. Specifically, the hybridomas can be produced by performing immunization by a conventional immunization method using an IL-6 receptor as a sensitizing antigen, fusing the resulting immune cells with known parent cells by a conventional cell fusion method, and then screening for cells that produce monoclonal antibodies using a conventional screening method.

Specifically, anti-IL-6 receptor antibodies can be produced as below. A human IL-6 receptor or mouse IL-6 receptor to be used as a sensitizing antigen for obtaining antibodies can be obtained by, for example, using the IL-6 receptor gene and/or amino acid sequences respectively disclosed in European Patent Application Publication No. EP 325474 and Japanese Patent Application Kokai Publication No. (JP-A) H03-155795 (unexamined, published Japanese patent application).

There are two types of IL-6 receptor proteins: one expressed on the cell membrane and the other separated from the cell membrane (soluble IL-6 receptor) (Yasukawa, K. et al., J. Biochem. (1990) 108, 673-676). The soluble IL-6 receptor is essentially composed of the extracellular region of the IL-6 receptor bound to the cell membrane, and differs from the membrane-bound IL-6 receptor in that it lacks the transmembrane region or both the transmembrane and intracellular regions. Any IL-6 receptor may be employed as the IL-6 receptor protein, as long as it can be used as a sensitizing antigen for producing an anti-IL-6 receptor antibody to be used in the present invention.

After an appropriate host cell is transformed with a known expression vector system inserted with an IL-6 receptor gene sequence, the target IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

An anti-gp130 antibody used in the present invention can be obtained as either a polyclonal or monoclonal antibody using known methods. A monoclonal antibody derived from a mammal is particularly preferred for the anti-gp130 antibody used in the present invention. The monoclonal antibodies derived from a mammal include those produced by a hybridoma and those produced by a host transformed with an expression vector containing an antibody gene using a genetic engineering method. By binding to gp130, this antibody inhibits the binding of an IL-6/IL-6-receptor complex to gp130, and blocks transduction of the IL-6 biological activity into cells.

Examples of such an antibody include the AM64 antibody (JP-A (Kokai) H03-219894), 4B11 and 2H4 antibodies (U.S. Pat. No. 5,571,513), and the B-S12 and B-P8 antibodies (JP-A (Kokai) H08-291199).

Basically, hybridomas that produce an anti-gp130 monoclonal antibody can be produced using known techniques as below. Specifically, the hybridomas can be produced by performing immunization by a conventional immunization method using gp130 as a sensitizing antigen, fusing the resulting immune cells with known parent cells by a conventional cell fusion method, and then screening for cells that produce monoclonal antibodies using a conventional screening method.

Specifically, the monoclonal antibodies can be produced as below. For example, gp130 to be used as a sensitizing antigen for obtaining antibodies can be obtained by using the gp130 gene and/or amino acid sequences disclosed in European Patent Application Publication No. EP 411946.

After an appropriate host cell is transformed with a known expression vector system inserted with a gp130 gene sequence, the target gp130 protein is purified from the inside of the host cell or from the culture supernatant using a known method. This purified gp130 protein may be used as a sensitizing antigen. Alternatively, a gp130-expressing cell or a fusion protein of the gp130 protein and another protein may be used as a sensitizing antigen.

Mammals to be immunized with a sensitizing antigen are not particularly limited, but are preferably selected in consideration of the compatibility with parent cells used for cell fusion. Typically, rodents such as mice, rats, and hamsters are used.

Animals are immunized with a sensitizing antigen according to known methods. Typically, immunization is performed by, for example, intraperitoneal or subcutaneous injection of the sensitizing antigen to a mammal. Specifically, it is preferable to dilute or suspend the sensitizing antigen in Phosphate-Buffered Saline (PBS), physiological saline, and such, to an appropriate volume, and mix it with an appropriate amount of a conventional adjuvant such as Freund's complete adjuvant if desired and emulsify, and then administer to the mammal every four to 21 days for several times. An appropriate carrier may also be used for immunization with the sensitizing antigen.

After immunizing the mammal in this manner, and confirming that the serum level of a desired antibody has increased, immunized cells are removed from the mammal and subjected to cell fusion. Spleen cells are particularly preferred as the immunized cells to be subjected to cell fusion.

Myeloma cells from mammals are used as parent cells to be fused with the immunized cells. So far, various known cell lines such as P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), and R210 (Galfre, G. et al., Nature (1979) 277, 131-133) are suitably used.

Basically, cell fusion of the aforementioned immune cells with myeloma cells can be performed according to known methods such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. For example, polyethylene glycol (PEG) or Sendai virus (HVJ) is used as the fusion promoter, and if desired, an adjuvant such as dimethyl sulfoxide can be further added for use in improving the fusion efficiency.

The ratio of immune cells to myeloma cells used is preferably, for example, 1 to 10 immune cells for each myeloma cell. The culture medium used for the cell fusion is, for example, an RPMI1640 or MEM culture medium suitable for the proliferation of the myeloma cell lines. Other conventional culture media used for this type of cell culture can also be used. Furthermore, serum supplements such as fetal calf serum (FCS) can also be used in combination.

For cell fusion, the fusion cells (hybridomas) of interest are formed by thoroughly mixing predetermined amounts of the aforementioned immune cell and myeloma cell in the aforementioned culture medium, adding a PEG solution (for example, a solution of PEG with an average molecular weight of about 1,000 to 6,000) pre-heated to about 37° C., usually at a concentration of 30% to 60% (w/v), and then mixing them. Then, cell fusion agents and such that are unsuitable for the growth of hybridomas can be removed by repeating the operation of sequentially adding an appropriate culture medium and removing the supernatant by centrifugation.

The hybridomas are selected by culturing in a general selection culture medium, for example, the HAT culture medium (a culture medium containing hypoxanthine, aminopterin, and thymidine). Culturing in the HAT culture medium is continued for a sufficient period, generally from several days to several weeks, to kill cells other than the hybridomas of interest (unfused cells). Then, a standard limiting dilution method is performed to screen for and clone hybridomas that produce an antibody of interest.

Besides obtaining the hybridomas by immunizing non-human animals with an antigen, desired human antibodies having a binding activity to a desired antigen or antigen-expressing cell can be obtained by sensitizing a human lymphocyte with a desired antigen protein or antigen-expressing cell in vitro, and fusing the sensitized B lymphocyte with a human myeloma cell such as U266 (see, Japanese Patent Application Kokoku Publication No. (JP-B) H01-59878 (examined, approved Japanese patent application published for opposition)). Further, an antigen or antigen-expressing cell may be administered to a transgenic animal having a repertoire of human antibody genes, and then a desired human antibody may be obtained following the aforementioned method (see, International Patent Application Publication Nos. WO 93/12227, WO 92/03918, WO 94/02602, WO 94/25585, WO 96/34096, and WO 96/33735).

The hybridomas prepared as such that produce monoclonal antibodies can be subcultured in a conventional culture medium and stored in liquid nitrogen for a long period.

To obtain monoclonal antibodies from the hybridomas, the following methods may be employed: culturing the hybridomas according to conventional methods and obtaining the antibodies as a culture supernatant or proliferating the hybridomas by administering them to a compatible mammal and obtaining the antibodies from ascites; and so on. The former method is suitable for obtaining antibodies with high purity, and the latter is suitable for large-scale antibody production.

For example, hybridomas that produce anti-IL-6 receptor antibodies can be prepared by the method disclosed in JP-A (Kokai) H03-139293. Such a preparation can be carried out by injecting hybridomas that produce PM-1 antibodies into the abdominal cavity of a BALB/c mouse, obtaining ascites, and then purifying the PM-1 antibodies from the ascites; or by culturing the hybridomas in an appropriate medium (such as an RPMI 1640 medium containing 10% fetal bovine serum, and 5% BM-Condimed H1 (Boehringer Mannheim); the hybridoma SFM medium (GIBCO-BRL); or the PFHM-II medium (GIBCO-BRL)) and then purifying the PM-1 antibodies from the culture supernatant.

Recombinant antibodies can be used as the monoclonal antibodies of the present invention, wherein the recombinant antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., THERAPEUTIC MONOCLONAL ANTIBODIES, Published in the United Kingdom by MACMILLAN PUBLISHERS LTD, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using an mRNA Purification Kit (Pharmacia) and such. Alternatively, mRNAs can be directly prepared using the QuickPrep mRNA Purification Kit (Pharmacia).

cDNAs of the antibody V regions are synthesized from the obtained mRNAs using reverse transcriptase. cDNAs may be synthesized using the AMV Reverse Transcriptase First-strand cDNA Synthesis Kit and such. Further, to synthesize and amplify the cDNAs, the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and PCR may be used. A DNA fragment of interest is purified from the obtained PCR products and then ligated with a vector DNA. Then, a recombinant vector is prepared by using the above, and introduced into *Escheri-*

*chia coli* and such, and then its colonies are selected to prepare a desired recombinant vector. The nucleotide sequence of the DNA of interest is confirmed by a known method such as the dideoxy method.

When a DNA encoding the V region of the antibody of interest is obtained, the DNA is ligated with a DNA encoding the constant region (C region) of a desired antibody, and inserted into an expression vector. Alternatively, a DNA encoding an antibody V region may be inserted into an expression vector comprising a DNA of an antibody C region.

To produce an antibody to be used in the present invention, an antibody gene is inserted into an expression vector such that it is expressed under the control of an expression-regulating region such as an enhancer and promoter, as described below. Then, the antibody can be expressed by transforming a host cell with this expression vector.

In the present invention, artificially modified recombinant antibodies, for example, chimeric antibodies, humanized antibodies, or human antibodies can be used, for example, to reduce heteroantigenicity against humans. These modified antibodies can be prepared using known methods.

A chimeric antibody can be obtained by ligating a DNA encoding an antibody V region obtained as above with a DNA encoding a human antibody C region, inserting it into an expression vector, and introducing the vector into a host to produce the chimeric antibody (see, European Patent Application Publication No. EP 125023; International Patent Application Publication No. WO 92-19759). This known method can be used to obtain chimeric antibodies useful for the present invention.

Humanized antibodies are also referred to as reshaped human antibodies or antibodies made into the human type. They are produced by transplanting the complementarity determining regions (CDRs) of an antibody from a non-human mammal (for example, a mouse) into the CDRs of a human antibody. General methods for this gene recombination are also known (see, European Patent Application Publication No. EP 125023, International Patent Application Publication No. WO 92-19759).

More specifically, DNA sequences designed to ligate the CDRs of a mouse antibody with the framework regions (FRs) of a human antibody are synthesized by PCR from several oligonucleotides produced to contain overlapping portions at their termini. The obtained DNA is ligated with a DNA encoding a human antibody C region and inserted into an expression vector, and the expression vector is introduced into a host to produce the humanized antibody (see, European Patent Application Publication No. EP 239400, International Patent Application Publication No. WO 92-19759).

Human antibody FRs to be ligated via the CDRs are selected so that the CDRs form satisfactory antigen binding sites. The amino acid(s) within the framework regions of the antibody variable regions may be substituted as necessary so that the CDRs of the reshaped human antibody form appropriate antigen binding sites (Sato, K. et al., Cancer Res. (1993) 53, 851-856).

Human antibody C regions are used for the chimeric and humanized antibodies. Examples of human antibody C regions include Cγ, and for example, Cγ1, Cγ2, Cγ3, or Cγ4 may be used. Furthermore, to improve the stability of the antibodies or their production, the human antibody C regions may be modified.

Chimeric antibodies are composed of the variable region of an antibody derived from a non-human mammal and the C region derived from a human antibody; and humanized antibodies are composed of the CDRs of an antibody derived from a non-human mammal and the framework regions and C regions derived from a human antibody. Their antigenicity in the human body is reduced, and thus they are useful as antibodies for use in the present invention.

Preferred specific examples of humanized antibodies of an anti-IL-6 receptor antibody for use in the present invention include a humanized PM-1 antibody (see, International Patent Application Publication No. WO 92-19759).

Furthermore, in addition to the aforementioned methods for obtaining human antibodies, techniques for obtaining human antibodies by panning using a human antibody library are also known. For example, the variable region of a human antibody can be expressed on a phage surface as a single chain antibody (scFv) by using the phage display method, and antigen-binding phages can then be selected. By analyzing the genes of the selected phages, the DNA sequence encoding the variable region of the human antibody which binds to the antigen can be determined. Once the DNA sequence of an scFv which binds to the antigen is revealed, an appropriate expression vector comprising the sequence can be prepared to obtain a human antibody. These methods are already known, and the publications, WO 92/01047, WO 92/20791, WO93/06213, WO 93/11236, WO 93/19172, WO 95/01438, and WO 95/15388, can be used as references.

The antibody gene constructed as described above can be expressed according to known methods. When a mammalian cell is used, the antibody gene can be expressed by using a DNA in which a commonly used effective promoter gene, the antibody gene to be expressed, and a poly A signal on the 3' side (downstream) of the antibody gene are operatively linked together, or by using a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and mammalian cell-derived promoters/enhancers such as human elongation factor 1α (HEF1α).

The expression can be easily performed, for example, by following the method in Mulligan et al. (Mulligan, R. C. et al., Nature (1979) 277, 108-114) when using the SV40 promoter/enhancer, or by following the method in Mizushima et al. (Mizushima, S. and Nagata S., Nucleic Acids Res. (1990) 18, 5322) when using the HEF1α promoter/enhancer.

When E. coli is used, the antibody gene can be expressed by operatively linking a commonly used effective promoter gene, a signal sequence for antibody secretion, and the antibody gene to be expressed. Examples of the promoter include a lacZ promoter and an araB promoter. A lacZ promoter can be used according to the method of Ward et al. (Ward, E. S. et al., Nature (1989) 341, 544-546; Ward, E. S. et al., FASEB J. (1992) 6, 2422-2427); and an araB promoter can be used according to the method of Better et al. (Better, M. et al., Science (1988) 240, 1041-1043).

When the antibody is produced into the periplasm of E. coli, the pel B signal sequence (Lei, S. P. et al., J. Bacteriol. (1987) 169, 4379-4383) may be used as a signal sequence for antibody secretion. The antibody produced into the periplasm is isolated, and then appropriately refolded the antibody structure to be used (see, for example, WO 96/30394).

As the replication origin, those derived from SV40, polyoma virus, adenovirus, bovine papilloma virus (BPV)

and such may be used. In addition, to increase the gene copy number in a host cell system, the expression vector may comprise the aminoglycoside phosphotransferase (APH) gene, thymidine kinase (TK) gene, E. coli xanthine-guanine phosphoribosyltransferase (Ecogpt) gene, dihydrofolate reductase (dhfr) gene, and such, as a selection marker.

Any production system may be used to prepare the antibodies for use in the present invention. The production systems for antibody preparation include in vitro and in vivo production systems. In vitro production systems include those using eukaryotic cells or those using prokaryotic cells.

When eukaryotic cells are used, the production systems include those using animal cells, plant cells, or fungal cells. Such animal cells include (1) mammalian cells such as CHO, COS, myeloma, baby hamster kidney (BHK), HeLa, and Vero; (2) amphibian cells such as Xenopus oocytes; and (3) insect cells such as sf9, sf21, and Tn5. Known plant cells include cells derived from Nicotiana tabacum, which may be cultured in callus. Known fungal cells include yeasts such as Saccharomyces (e.g., Saccharomyces cerevisiae) and mold fungi such as Aspergillus (e.g., Aspergillus niger).

When prokaryotic cells are used, production systems include those using bacterial cells. Known bacterial cells include E. coli and Bacillus subtilis.

Antibodies can be obtained by introducing the antibody gene of interest into these cells by transformation, and then culturing the transformed cells in vitro. Cells are cultured according to known methods. For example, DMEM, MEM, RPMI 1640, or IMDM may be used as the culture medium, and serum supplements such as fetal calf serum (FCS) may be used in combination. Alternatively, cells introduced with the antibody gene may be transferred into the abdominal cavity and such of an animal to produce the antibodies in vivo.

Meanwhile, in vivo production systems include those using animals or those using plants. When using animals, production systems include those using mammals or insects.

Mammals that can be used include goats, pigs, sheep, mice, and bovines (Vicki Glaser, SPECTRUM Biotechnology Applications, 1993). Further, insects that can be used include silkworms. When using plants, tobacco and such may be used.

An antibody gene is introduced into these animals or plants, and the antibodies are produced in the body of the animals or plants and then recovered. For example, an antibody gene can be prepared as a fusion gene by inserting it into the middle of a gene encoding a protein uniquely produced into milk, such as goat β casein. DNA fragments comprising the fusion gene, which includes the inserted antibody gene, are injected into goat embryos, and the embryos are introduced into female goats. The desired antibodies are obtained from milk produced by transgenic goats born from the goats that received the embryos, or their progenies. When appropriate, the transgenic goats may be given hormones to increase the volume of milk containing the desired antibodies that they produce (Ebert, K. M. et al., Bio/Technology (1994) 12, 699-702).

When silkworms are used, the silkworms are infected with a baculovirus inserted with the antibody gene of interest, and the desired antibodies are obtained from the body fluids of these silkworms (Maeda, S. et al., Nature (1985) 315, 592-594). Moreover, when tobacco is used, the antibody gene of interest is inserted into a plant expression vector such as pMON530, and the vector is introduced into bacteria such as Agrobacterium tumefaciens. This bacterium is used to infect tobacco such as Nicotiana tabacum, and then the desired antibody is obtained from the leaves of this tobacco (Julian, K.-C. Ma et al., Eur. J. Immunol. (1994) 24, 131-138).

When producing antibodies using in vitro or in vivo production systems as described above, DNAs encoding an antibody heavy chain (H chain) and light chain (L chain) may be inserted into separate expression vectors, and a host is then co-transformed with the vectors. Alternatively, the H chain-encoding DNA and L chain-encoding DNA may be inserted into a single expression vector for transforming a host (see International Patent Application Publication No. WO 94-11523).

The antibodies used in the present invention may be antibody fragments or modified products thereof, as long as they can be suitably used in the present invention. For example, antibody fragments include Fab, F(ab')2, Fv, and single chain Fv (scFv) in which the Fvs of the H and L chains are linked via an appropriate linker.

Specifically, the antibody fragments are produced by treating antibodies with enzymes such as papain or pepsin, or alternatively, by constructing genes encoding these antibody fragments and introducing them into expression vectors, and then expressing the vectors in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; and Bird, R. E. et al., TIBTECH (1991) 9, 132-137).

An scFv can be obtained by linking the H-chain V region and the L-chain V region of an antibody. In this scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, an arbitrary single chain peptide consisting of 12 to 19 amino acid residues.

A DNA encoding an scFv can be obtained by amplifying a DNA portion that encodes the desired amino acid sequence in template sequences with PCR using a primer pair which defines the termini of the portion, wherein a DNA encoding an H chain or an H-chain V region and a DNA encoding an L chain or an L-chain V region of the aforementioned antibodies are used as the templates, and then further amplifying the amplified DNA portion with a DNA that encodes a peptide linker portion and a primer pair that defines both ends of the linker so that it may be linked to each of the H and L chains.

Once an scFv-encoding DNA has been prepared, an expression vector comprising the DNA and a host transformed with the expression vector can be obtained according to conventional methods. In addition, an scFv can be obtained according to conventional methods by using the host.

Similar to the above, the antibody fragments can be produced by obtaining their genes, expressing them, and then using a host. An "antibody" as used herein encompasses such antibody fragments.

Antibodies bound to various molecules such as polyethylene glycol (PEG) may also be used as modified antibodies. An "antibody" as used herein encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and purified by affinity chromatography. Columns used for the affinity chromatography include protein A columns and protein G columns. Carriers used for the protein A columns include HyperD, POROS, and Sepharose F.F. Other methods used for the isolation and/or purification of ordinary proteins may be used without limitation.

For example, the antibodies used for the present invention may be isolated and purified by appropriately selecting and combining chromatographies other than the above-described affinity chromatography, filtration, ultrafiltration, salting-out, dialysis, and such. Examples of chromatographies include ion-exchange chromatography, hydrophobic chromatography, and gel filtration. These chromatographies can be applied to high performance liquid chromatography (HPLC). Alternatively, reverse phase HPLC may be used.

The concentration of the antibodies obtained as above can be determined by absorbance measurement, ELISA, and such. Specifically, when using absorbance measurement, the concentration can be determined by appropriately diluting the antibody solution with PBS(−), measuring its absorbance at 280 nm, and calculating the concentration by using the conversion factor 1.35 OD/1 mg/ml. Alternatively, when using ELISA, the concentration can be determined as below. Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody to be used in the present invention or an appropriately diluted sample comprising the antibody, or human IgG (CAPPEL) as a standard is added, and the plate is incubated for one hour at room temperature.

After washing, 100 µl of 5,000× diluted alkaline phosphatase-labeled anti-human IgG (BIO SOURCE) is added, and the plate is incubated for one hour at room temperature. After another wash, the substrate solution is added, the plate is incubated, and absorbance at 405 nm is measured using MICROPLATE READER Model 3550 (Bio-Rad) to calculate the concentration of the antibody of interest.

The IL-6 variants used in the present invention are substances that have binding activity to an IL-6 receptor and which do not transmit IL-6 biological activity. That is, the IL-6 variants compete with IL-6 for binding to an IL-6 receptor, but do not transmit IL-6 biological activity, and thus block IL-6-mediated signal transduction.

The IL-6 variants are produced by introducing mutation(s) by substituting amino acid residue(s) in the amino acid sequence of IL-6. Any IL-6 from which the IL-6 variant is derived can be used, but human IL-6 is preferred, considering antigenicity and such.

More specifically, the amino acid substitutions are performed by predicting the secondary structure of IL-6 from the IL-6 amino acid sequence using known molecular modeling programs such as WHATIF (Vriend et al., J. Mol. Graphics (1990) 8, 52-56), and further assessing the influence of the substituted amino acid residue(s) on the whole molecule. After determining the appropriate amino acid residue(s) to be substituted, mutation(s) are introduced by a commonly performed PCR method using a vector comprising a nucleotide sequence encoding a human IL-6 gene as a template to cause amino acid substitution(s), and the gene encoding the IL-6 variant is thereby obtained. If needed, this gene is inserted into an appropriate expression vector, and the IL-6 variant can be obtained according to the aforementioned methods for expression, production, and purification of recombinant antibodies.

Specific examples of the IL-6 variants are disclosed in Brakenhoff et al., J. Biol. Chem. (1994) 269, 86-93; Savino et al., EMBO J. (1994) 13, 1357-1367; WO 96-18648; and WO 96-17869.

Partial peptides of IL-6 or the IL-6 receptor to be used in the present invention are substances that have a binding activity to the IL-6 receptor or IL-6, respectively, and which do not transmit the IL-6 biological activities. That is, the partial peptides of IL-6 or the IL-6 receptor bind to and capture the IL-6 receptor or IL-6, and thereby specifically inhibit binding of IL-6 to the IL-6 receptor. As a result, the IL-6 biological activities are not transmitted, and thus, IL-6-mediated signal transduction is blocked.

Partial peptides of IL-6 or the IL-6 receptor are peptides that are composed of the whole amino acid sequence of the region of the IL-6 or IL-6 receptor amino acid sequence or a part thereof involved in the binding between IL-6 and the IL-6 receptor. Such peptides are usually composed of 10 to 80, preferably 20 to 50, more preferably 20 to 40 amino acid residues.

Partial peptides of IL-6 or the IL-6 receptor can be produced by specifying the region of the IL-6 or IL-6 receptor amino acid sequence involved in the binding between IL-6 and the IL-6 receptor, and applying generally known methods such as genetic engineering techniques and peptide synthesis methods to the whole amino acid sequence of the specified region or a portion thereof.

To prepare a partial peptide of IL-6 or an IL-6 receptor by genetic engineering methods, a DNA sequence encoding the desired peptide is inserted into an expression vector, and then the peptide can be obtained by applying the aforementioned methods for expressing, producing, and purifying recombinant antibodies.

To produce a partial peptide of IL-6 or an IL-6 receptor by peptide synthesis methods, generally used peptide synthesis methods such as solid phase synthesis methods and liquid phase synthesis methods may be used.

Specifically, the peptides can be synthesized according to the method described in "The sequel of Development of Pharmaceuticals (Zoku Iyakuhin no Kaihatsu), Vol. 14, Peptide Synthesis (ed. Haruaki Yajima, 1991, Hirokawa Shoten)". As a solid phase synthesis method, the following method and such can be employed: binding the amino acid corresponding to the C terminus of the peptide to be synthesized to a support that is insoluble in organic solvents, and then elongating the peptide strand by alternately repeating: the reaction of condensing amino acids whose α-amino groups and branch chain functional groups are protected with appropriate protecting groups, one at a time in a C terminus to N terminus direction; and the reaction of removing the protecting groups from the α-amino groups of the resin-bound amino acids or peptides. Solid-phase peptide synthesis is broadly classified into the Boc method and the Fmoc method, depending on the type of protecting groups used.

After synthesizing the peptide of interest as above, deprotection reaction and cleavage reaction of the peptide strand from the support are carried out. For the cleavage reaction of the peptide strand, hydrogen fluoride or trifluoromethane sulfonic acid is generally used for the Boc method, and TFA is generally used for the Fmoc method. In the Boc method, for example, the protected peptide-bound resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, the deprotection reaction and the cleavage reaction of the peptide strand from the support can be performed in TFA and such by operations similar to those described above.

The obtained crude peptides can be separated and purified by applying HPLC. Elution may be performed under optimum conditions using a water-acetonitrile solvent system, which is generally used for protein purification. The fractions corresponding to the peaks of the obtained chromatographic profile are collected and freeze-dried. Peptide fractions purified this way are identified by molecular weight analysis via mass spectrum analysis, amino acid composition analysis, amino acid sequence analysis, and such.

Specific examples of the partial peptides of IL-6 and the IL-6 receptor are disclosed in JP-A (Kokai) H02-188600, JP-A (Kokai) H07-324097, JP-A (Kokai) H08-311098, and U.S. Pat. No. 5,210,075.

The antibodies used in the present invention may be conjugate antibodies that are bound to various molecules such as polyethylene glycol (PEG), radioactive substances, and toxins. Such conjugate antibodies can be obtained by chemically modifying the obtained antibodies. Methods for antibody modification have been already established in this field. Accordingly, the term "antibody" as used herein encompasses such conjugate antibodies.

"Antibodies" of the present invention include those that have been post-translationally modified. Post-translational modifications include, but are not limited to, modification of a heavy-chain or light-chain N-terminal glutamine or glutamic acid into a pyroglutamic acid by pyroglutamylation.

Preferred examples of the "anti-IL-6 receptor antibody" of the present invention include tocilizumab which is a humanized anti-IL-6 receptor IgG1 antibody, humanized anti-IL-6 receptor antibodies produced by modifying the constant and variable regions of tocilizumab, and antibodies that bind to the same epitope bound by tocilizumab.

Specific examples include an antibody containing the heavy chain variable region of SEQ ID NO: 1 (heavy chain variable region of tocilizumab) and the light chain variable region of SEQ ID NO: 2 (light chain variable region of tocilizumab), and an antibody containing the heavy chain variable region of SEQ ID NO: 5 (heavy chain variable region of SA237) and the light chain variable region of SEQ ID NO: 6 (light chain variable region of SA237).

More specifically, examples include an antibody containing the heavy chain of SEQ ID NO: 3 (heavy chain of tocilizumab) and the light chain of SEQ ID NO: 4 (light chain of tocilizumab), and an antibody containing the heavy chain of SEQ ID NO: 7 (heavy chain of SA237) and the light chain of SEQ ID NO: 8 (light chain of SA237).

Such antibodies can be obtained according to the methods described in WO2010/035769, WO2010/107108, WO2010/106812, and such. Specifically, antibodies can be produced using genetic recombination techniques known to those skilled in the art, based on the sequence of the above-mentioned anti-IL-6 receptor antibody (see, for example, Borrebaeck C A K and Larrick J W, THERAPEUTIC MONOCLONAL ANTIBODIES, Published in the United Kingdom by MACMILLAN PUBLISHERS LTD, 1990). A recombinant antibody can be obtained by cloning a DNA encoding the antibody from a hybridoma or an antibody-producing cell such as an antibody-producing sensitized lymphocyte, inserting the DNA into an appropriate vector, and introducing the vector into a host (host cell) to produce the antibody.

Such antibodies can be isolated and purified using isolation and purification methods conventionally used for antibody purification, without limitation. For example, the antibodies can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Specifically, an "antibody that binds to the same epitope" as a reference antibody refers to an antibody that blocks binding of the reference antibody to its antigen in a competition assay by 60% or more, by 70% or more, by 80% or more, or by 90% or more.

In another aspect, competition assays may be used to identify an antibody that competes with tocilizumab for binding to IL-6 receptor. In certain embodiments, such a competing antibody binds to the same epitope (e.g., a linear or a conformational epitope) that is bound by tocilizumab. Detailed exemplary methods for mapping an epitope to which an antibody binds are provided in Morris (1996) "Epitope Mapping Protocols" in Methods in Molecular Biology vol. 66 (Humana Press, Totowa, NJ).

In an exemplary competition assay, immobilized IL-6 receptor is incubated in a solution comprising a first labeled antibody that binds to IL-6 receptor (e.g., tocilizumab) and a second unlabeled antibody that is being tested for its ability to compete with the first antibody for binding to IL-6 receptor. The second antibody may be present in a hybridoma supernatant. As a control, immobilized IL-6 receptor is incubated in a solution comprising the first labeled antibody but not the second unlabeled antibody. After incubation under conditions permissive for binding of the first antibody to IL-6 receptor, excess unbound antibody is removed, and the amount of label associated with immobilized IL-6 receptor is measured. If the amount of label associated with immobilized IL-6 receptor is substantially reduced in the test sample relative to the control sample, then that indicates that the second antibody is competing with the first antibody for binding to IL-6 receptor. See Harlow and Lane (1988) Antibodies: A Laboratory Manual ch. 14 (Cold Spring Harbor Laboratory, Cold Spring Harbor, NY).

Examples of an "anti-CCL2 antibody" in the present invention include, but are not limited to, the antibodies described in Japanese Patent No. 9067399, JP-A (Kokai) H05276986, WO03048083, US20040047860, US20060039913, and WO2006/125202. More specific examples include ABN912 and CNT0888 (carlumab). These antibodies can be produced by using any known techniques according to the methods described in Japanese Patent No. 9067399, JP-A (Kokai) H05276986, WO03048083, US20040047860, US20060039913, and WO2006/125202.

When the CCR2 inhibitor is a low-molecular-weight substance, examples of the substance include, but are not limited to, propagermanium (3-oxygermylpropionic acid polymer), INCB3344, RS-504393, or substances described in WO2016/187393.

Therapeutic or prophylactic agents of the present invention can be formulated to produce freeze-dried formulations or solution formulations by mixing, if necessary, with suitable pharmaceutically acceptable carriers, vehicles, and such. The suitable pharmaceutically acceptable carriers and vehicles include, for example, sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. Other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol may also be contained. When preparing an aqueous solution for injection, physiological saline and isotonic solutions comprising glucose and other adjuvants such as D-sorbitol, D-mannose, D-mannitol, and sodium chloride may be used; and appropriate solubilizers such as alcohol (for example, ethanol), polyalcohols (such as propylene glycol and PEG), and nonionic surfactants (such as polysorbate 80, polysorbate 20, poloxamer 188, and HCO-50) may be used in combination. By mixing hyaluronidase into the formulation, a larger fluid volume can be administered subcutaneously (Expert Opin. Drug Deliv. 2007 July; 4(4): 427-40). Furthermore, syringes may be prefilled with the pharmaceutical composition of the present invention. Solution formulations can be prepared according to the method described in WO2011/090088.

If necessary, the therapeutic or prophylactic agents of the present invention may be encapsulated in microcapsules (e.g., those made of hydroxymethylcellulose, gelatin, and poly(methylmetacrylate)), or incorporated into colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also known, and such methods may be applied to the therapeutic or prophylactic agents of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); and EP 133,988).

When a low-molecular-weight substance is comprised as an active ingredient, the therapeutic or prophylactic agent of the present invention can be prepared by mixing with an appropriate pharmaceutically acceptable carrier, or such, and formulated into tablets, capsules, granules, powders, or pills.

Examples of pharmaceutically acceptable carriers or such include, but are not limited to, sugars such as lactose, glucose, and sucrose; starches such as corn starch and potato starch; cellulose and derivatives such as sodium carboxymethyl cellulose, ethyl cellulose, and methyl cellulose; tragacanth gum powder; malt; gelatin; talc; solid lubricants such as stearic acid and magnesium stearate; calcium sulfate; plant oils such as peanut oil, cottonseed oil, sesame oil, olive oil, corn oil, vegetable oil, and cacao oil; polyhydric alcohols such as propylene glycol, glycerin, sorbitol, mannitol, and polyethylene glycol; alginic acid; emulsifiers such as TWEEN; humectants such as lecithin; colorants; fragrances; tableting agents; stabilizers; antioxidants; preservatives; pyrogen-free water; isotonic aqueous salt solution; and a phosphate buffer solution.

The therapeutic agent of the present invention can be administered to a patient via any appropriate route. For example, it can be administered to a patient intravenously by bolus injection or by continuous infusion, intramuscularly, intraperitoneally, intracerebrospinally, transdermally, subcutaneously, intracutaneouly, intraarticularly, sublingually, intrasynovially, orally, by inhalation, locally, or externally, for a certain period of time.

The dose can be selected, for example, in the range of 0.0001 mg to 100 mg of active ingredient per 1 kg of body weight per dose. Alternatively, for example, when administering to a human patient, the active ingredient per patient may be selected in the range of 0.001 mg to 1000 mg per 1 kg of body weight. Regarding an IL-6 inhibitor or CCR2 inhibitor, the active ingredient of which is an antibody, the amount included in a single dose is preferably, for example, approximately 0.01 mg to 50 mg per 1 kg of body weight. Combination Therapies and Pharmaceutical Compositions In a non-limiting embodiment of the present invention, the combination therapy of the present invention provides methods for suppressing cell proliferation, for suppressing tumor weight, for suppressing tumor volume, for treating cancer, or for preventing cancer, each of the methods comprising administering effective amounts of an IL-6 inhibitor and a CCR2 inhibitor. In several embodiments, the combination therapy of the present invention is highly effective for suppressing cell proliferation, suppressing tumor weight, suppressing tumor volume, treating cancer, or preventing cancer, as compared to monotherapy using the IL-6 inhibitor or CCR2 inhibitor. In another embodiment, the combination therapy of the present invention has synergistic effects or additive effects of suppressing cell proliferation, suppressing tumor weight, suppressing tumor volume, treating cancer, or preventing cancer.

In several embodiments, the term "effective amount" in the present invention refers to a dose of an IL-6 inhibitor and/or a CCR2 inhibitor that is effective for treating or preventing a disease (in the present invention, in particular, urologic cancer) in an individual. For example, if the IL-6 inhibitor is an antibody, the antibody is administered, for example, once every one to ten weeks, preferably once every one to eight weeks, or more preferably once every one to four weeks, at a dose, for example, in the range of 0.0001 mg to 1000 mg, preferably 0.001 mg to 100 mg, or more preferably 0.01 to 50 mg per 1 kg of body weight for a single administration, but the administration is not limited thereto. If the CCR2 inhibitor is an anti-CCL2 antibody, the antibody is administered, for example, once every one to ten weeks, preferably once every one to eight weeks, or more preferably once every one to four weeks, at a dose in the range of 0.0001 mg to 1000 mg, preferably 0.001 mg to 100 mg, or more preferably 0.01 to 50 mg per 1 kg of body weight for a single administration, but the administration is not limited thereto. If the CCR2 inhibitor is a low-molecular-weight substance that binds to CCR2 and blocks the signal of CCL2, the substance is administered every day, for example, in the range of 0.01 mg to 40 mg per 1 kg of body weight per day, or preferably 0.25 mg to 10 mg per 1 kg of body weight per day, for a single administration. If the CCR2 inhibitor is propagermanium, propagermanium is administered, for example, in the range of 20 to 40 mg per day, or preferably 30 mg per day, which amount is given, for example, into two to four divided doses, or preferably into three divided doses, but the administration is not limited thereto.

The above-mentioned urologic cancer in the present invention is not particularly limited, but is preferably bladder cancer.

In several embodiments, "treatment/treating/therapeutic" in the present invention means that the combination therapy of the present invention suppresses tumor growth in urinary organ, decreases the number of cancer cells, suppresses cancer cell proliferation, decreases tumor volume, decreases tumor weight, suppresses cancer cell metastasis, or ameliorates various symptoms caused by cancer in individuals. Furthermore, in several embodiments, "prevention/preventing/prophylactic" in the present invention refers to inhibiting increase in the number of cancer cells due to repopulation of cancer cells that have been decreased, inhibiting repopulation of cancer cells whose proliferation has been suppressed, inhibiting the decreased tumor size to become large again, or preventing macroscopic reappearance of cancer that has disappeared macroscopically (or has been cured) by topical treatment.

In several embodiments, the combination therapy of the present invention provides methods for enhancing therapeutic or prophylactic effects of a CCR2 inhibitor by using an IL-6 inhibitor, in cancer treatment or prevention with the CCR2 inhibitor. In another embodiment, the combination therapy of the present invention provides methods for enhancing therapeutic or prophylactic effects of an IL-6 inhibitor by using a CCR2 inhibitor, in cancer treatment or prevention with the IL-6 inhibitor. Herein, enhancement of therapeutic or prophylactic effects refers to, for example, increase in efficacy rate of the treatment, decrease in the amount of the IL-6 inhibitor or the CCR2 inhibitor that is administered for the treatment, and/or shortening of the period of the treatment with an IL-6 inhibitor or a CCR2 inhibitor, but is not limited thereto. In another embodiment, the combination therapy of the present invention provides methods for extending progression-free survival in individuals, the method comprising administering an effective amount of an IL-6 inhibitor and a CCR2 inhibitor.

In several embodiments, the combination therapy of the present invention comprises administering an IL-6 inhibitor and a CCR2 inhibitor. The IL-6 inhibitor and the CCR2 inhibitor can be administered by any appropriate methods known in the art. For example, the IL-6 inhibitor and the CCR2 inhibitor can be administered in parallel (i.e., simultaneously) or successively (i.e., at different time points). In several embodiments, when the IL-6 inhibitor and the CCR2 inhibitor are administered successively (i.e., at different time points), the interval between administration of the IL-6 inhibitor and the CCR2 inhibitor is not particularly limited and the interval can be determined by taking account for factors such as the administration route and dosage form. The interval is, for example, 0 to 168 hours, preferably 0 to 72 hours, more preferably 0 to 24 hours, and even more preferably 0 to 12 hours, but is not limited thereto.

In several embodiments, the IL-6 inhibitor and the CCR2 inhibitor are administered simultaneously. In several embodiments, the IL-6 inhibitor is administered at intervals (i.e., intermittently). In several embodiments, the IL-6 inhibitor is administered before administration of the CCR2 inhibitor. In several embodiments, the IL-6 inhibitor is administered after administration of the CCR2 inhibitor.

In several embodiments, the CCR2 inhibitor is administered at intervals (i.e., intermittently). In several embodiments, the CCR2 inhibitor is administered before administration of the IL-6 inhibitor. In several embodiments, the CCR2 inhibitor is administered after administration of the IL-6 inhibitor.

In several embodiments, IL-6 inhibitors and CCR2 inhibitors which are known or described herein can be used in the above-described combination therapies of the present invention.

In several embodiments, an additional therapy can be performed in addition to the combination therapies using the IL-6 inhibitor and the CCR2 inhibitor. In several embodiments, a therapy to add to the combination therapy of the present invention may comprise administration of an additional IL-6 inhibitor and/or CCR2 inhibitor.

A non-limiting embodiment of the present invention provides agents for suppressing cell proliferation (agents for inhibiting cell proliferation), agents for suppressing volume or weight of cancer cells or cancer cell-comprising tumor tissues, and therapeutic or prophylactic agents for cancer (herein below, collectively referred to as pharmaceutical compositions and such of the present invention), each comprising an IL-6 inhibitor, a CCR2 inhibitor, or a combination of the IL-6 inhibitor and the CCR2 inhibitor. In several embodiments, the pharmaceutical compositions of the present invention can be used in the combination therapy of the present invention. In several embodiments, the pharmaceutical compositions of the present invention are highly effective for suppressing cell proliferation, suppressing volume or weight of cancer cells or cancer cell-comprising tumor tissues, or treating or preventing cancer, due to combined use of the IL-6 inhibitor and the CCR2 inhibitor, as compared to monotherapy using the IL-6 inhibitor or the CCR2 inhibitor. In another embodiment, the pharmaceutical compositions of the present invention have synergistic effects or additive effects on suppressing cell proliferation, suppressing volume or weight of cancer cells or cancer cell-comprising tumor tissues, or treating or preventing cancer due to combined use of the IL-6 inhibitor and the CCR2 inhibitor.

In several embodiments, the pharmaceutical compositions according to the present invention "comprising a combination of an IL-6 inhibitor and a CCR2 inhibitor" refers to pharmaceutical compositions in which the IL-6 inhibitor and the CCR2 inhibitor are combined for use in simultaneous, separate, or sequential administration in treatment or prevention of a disease (in particular, urologic cancer in the present invention). For example, the pharmaceutical compositions of the present invention can be provided in the form of a combination preparation containing both an IL-6 inhibitor and a CCR2 inhibitor. Alternatively, for example, as the pharmaceutical compositions of the present invention, a pharmaceutical agent containing an IL-6 inhibitor and a pharmaceutical agent containing a CCR2 inhibitor can be separately provided, and these pharmaceutical agents may be used simultaneously or sequentially. The urologic cancer is not particularly limited but is preferably bladder cancer.

In several embodiments, the present invention provides pharmaceutical compositions for use in combination with a CCR2 inhibitor, the compositions comprising an IL-6 inhibitor as an active ingredient.

In several embodiments, the present invention provides pharmaceutical compositions for use in combination with an IL-6 inhibitor, the compositions comprising a CCR2 inhibitor as an active ingredient.

In several embodiments, the present invention provides pharmaceutical compositions for enhancing therapeutic effects of a CCR2 inhibitor in cancer treatment with the CCR2 inhibitor, by using an IL-6 inhibitor in combination with the CCR2 inhibitor.

In several embodiments, the present invention provides pharmaceutical compositions for enhancing therapeutic effects of an IL-6 inhibitor in cancer treatment, by using a CCR2 inhibitor in combination with the IL-6 inhibitor.

In several embodiments, the present invention provides use of an IL-6 inhibitor and/or a CCR2 inhibitor for the production of pharmaceutical compositions comprising as active ingredients the IL-6 inhibitor and/or the CCR2 inhibitor.

In the present invention, "comprising as active ingredients an IL-6 inhibitor and/or a CCR2 inhibitor" means "comprising the IL-6 inhibitor and/or the CCR2 inhibitor as major active component(s)", and does not limit the content of the IL-6 inhibitor and/or the CCR2 inhibitor.

KDM6A is a histone-modifying protein, and its gene is located on the X chromosome. KDM6A is known to promote demethylation of the lysine residue at the 27th position of tri-/dimethylated histone H3 (H3K27) via the JmjC domain, bind to mixed lineage leukemia 3 (MLL3, KMT2C) or mixed lineage leukemia 4 (MLL4, KMT2D), which are histone methylases, via a protein interaction domain called tetratricopeptide repeat (TPR), and play role in methylation of the lysine residue at the 4th position of histone H3 (H3K4) as a component of complex of proteins associated with Sett (COMPASS)-like complex, which is a protein complex. H3K27 methylation is a transcription-suppressing histone mark, H3K4 methylation is a transcription-promoting histone mark, and KDM6A is thought to promote transcriptional activation of target genes through the above-mentioned functions.

In one embodiment of the above-mentioned aspect, the present invention provides a pharmaceutical composition for treating or preventing urologic cancer (a therapeutic or prophylactic agent for urologic cancer), the pharmaceutical composition comprising an IL-6 inhibitor, a CCR2 inhibitor, or a combination of an IL-6 inhibitor and a CCR2 inhibitor, wherein the pharmaceutical composition is for administration to an individual who has been selected by the steps of evaluating a biological sample obtained from an individual (for example, a urologic cancer patient) for the presence or absence of reduced KDM6A function, reduced KDM6A expression, and/or a mutation (preferably a loss-of-function mutation) of the KDM6A gene, and selecting the individual when the individual has reduced KDM6A function, reduced KDM6A expression, and/or a mutation (preferably a loss-of-function mutation) of the KDM6A gene as a responder to treatment or prevention with the pharmaceutical composition.

In another embodiment, the present invention provides an IL-6 inhibitor, a CCR2 inhibitor, or a combination of an IL-6 inhibitor and a CCR2 inhibitor for use in treatment or prevention of urologic cancer, wherein the IL-6 inhibitor, the CCR2 inhibitor, or the combination of an IL-6 inhibitor and a CCR2 inhibitor is for administration to an individual who has been selected by the steps of evaluating a biological sample obtained from an individual (for example, a urologic cancer patient) for the presence or absence of reduced KDM6A function, reduced KDM6A expression, and/or a mutation (preferably a loss-of-function mutation) of the KDM6A gene, and selecting the individual when the individual has reduced KDM6A function, reduced KDM6A expression, and/or a mutation (preferably a loss-of-function mutation) of the KDM6A gene as a responder to the treatment or prevention.

In another embodiment, the present invention provides a method of treatment or prevention of urologic cancer, the method comprising the steps of administering an effective amount of an IL-6 inhibitor to an individual (for example, a urologic cancer patient) and administering an effective amount of a CCR2 inhibitor to the individual, or the step of administering a combination of an IL-6 inhibitor and a CCR2 inhibitor, wherein the method of treatment or prevention of urologic cancer comprises the step of evaluating a biological sample obtained from an individual for the presence or absence of reduced KDM6A function, reduced KDM6A expression, and/or a mutation (preferably a loss-of-function mutation) of the KDM6A gene, and selecting the individual when the individual has reduced KDM6A function, reduced KDM6A expression, and/or a mutation (preferably a loss-of-function mutation) of the KDM6A gene as a responder to the treatment or prevention. The step of evaluating and the step of selecting are preferably performed before the step of administering.

In these embodiments, the presence or absence of reduced p53 expression, reduced p53 function, and/or a p53 mutation in an individual may be evaluated, and an individual who has reduced p53 expression, reduced p53 function, and/or a p53 mutation may be selected as a responder to the treatment or prevention. Methods for evaluating the presence or absence of p53 mutation are known in the art.

In the present invention, reduced KDM6A function, reduced KDM6A expression, a mutation of the KDM6A gene, and a loss-of-function mutation of the KDM6A gene can be checked, for example, by immunostaining a sample collected from a urologic cancer patient using an antibody against KDM6A, or by performing Western blotting or exon sequencing method on a sample collected from a patient.

For example, when KDM6A protein expression is markedly reduced in comparison with a KDM6A-positive control (for example, a biological sample collected from a patient who does not have reduced KDM6A function, does not have reduced KDM6A expression, does not have a mutation of the KDM6A gene, or does not have a loss-of-function mutation of the KDM6A gene) as a result of immunostaining using an antibody against KDM6A, it can be determined that KDM6A function is reduced, KDM6A expression is reduced, the KDM6A gene has a mutation, or the KDM6A gene has a loss-of-function mutation.

In the present invention, reduction of KDM6A function includes KDM6A function deficiency and inactivation of KDM6A.

In the present invention, reduction of KDM6A expression includes marked reduction of KDM6A protein expression and the absence of KDM6A protein expression.

In the present invention, a mutation of the KDM6A gene include loss-of-function mutations of the KDM6A gene. Specific mutations include nonsense mutations, frameshift mutations, splice mutations, and deletions.

The p53 gene is a tumor suppressor gene that has functions such as regulating DNA repair and cell cycle and inducing apoptosis, and p53 gene mutation has been observed in various cancers. A mutant p53 protein has a long half-life and accumulates intracellularly; therefore, p53 antibodies appear in the serum (Lowe S W, Bodis S, McClatchey A et al: p53 status and the efficacy of cancer therapy in vivo. Science 266: 807-810, 1994). Accordingly, measuring p53 antibodies in the serum by the ELIZA method is considered to be useful for finding cancers associated with p53 gene mutations (Shimada H, Ochiai T, Nomura F et al: Titration of serum p53 antibodies in 1085 patients with various types of malignant tumors. Cancer 97: 682-689, 2003), and the measuring has been approved for health care insurance coverage as a tumor marker test for esophageal cancer, colorectal cancer, and breast cancer since November 2007.

In the present invention, reduced p53 function includes p53 function deficiency and inactivation of p53.

In the present invention, reduced p53 expression includes marked reduction in p53 protein expression and no detection of p53 protein expression.

In the present invention, specific examples of mutations of the p53 gene include missense mutations, nonsense mutations, frameshift mutations, and deletions.

Examples

Next, the present invention will be specifically described with reference to Examples, but the present invention is not limited to the following Examples.

Mice that lack UTX specifically in bladder epithelium ($Utx^{\Delta/\Delta}$) were prepared and analyzed to investigate the involvement of UTX (KDM6A) deletion in bladder cancer. Deletion of Utx was confirmed in the bladder epithelium of $Utx^{\Delta/\Delta}$ mice, but no tumor onset was observed in the bladder after long-term observation, and UTX deficiency alone was considered insufficient for the onset of bladder cancer.

The most frequently mutated gene in bladder cancer is p53, and Utx deletion and p53 mutation are known to frequently coexist (The Cancer Genome Atlas Research Network, Nature 2014, vol. 507, p. 315-322). Therefore, Utx mice were crossed with p53 heterozygous mice to produce $Utx^{\Delta/\Delta}$, $p53^{+/-}$ mice. Interestingly, after long-term observation of $Utx^{\Delta/\Delta}$, $p53^{+/-}$ mice, onset of carcinoma in situ (CIS) was seen, indicating that Utx deletion is involved in the onset of bladder cancer in coordination with p53 mutation.

Furthermore, since exposure to mutagens such as smoking is considered to be important for the onset of bladder cancer, N-butyl-N-(4-hydro-oxybutyl) nitorosamine (BBN), which is an experimental bladder cancer inducer, was administered to mice. As a result, 10 weeks after the administration, about 60% of the control $Utx^{+/+}$, $p53^{+/-}$ mice showed dysplasia to carcinoma in situ (Dysplasia to CIS), whereas 100% of $Utx^{\Delta/\Delta}$, $p53^{+/-}$ mice showed onset of dysplasia to carcinoma in situ (FIG. 1A) and some had further progressed to cancer infiltrating into the muscle layer (Muscle invasive cancer) (FIG. 1B). These results indicate that Utx deletion and p53 mutation enhance bladder cancer susceptibility and this, with mutagens acting on coordinately, allows progress into advanced cancer. Our mice may be the first in vivo model of human bladder tumors produced from the viewpoint of accumulation of gene mutations and effects of environmental mutagens.

To analyze the involvement of UTX deletion in the onset of bladder cancer, we collected urothelium from the bladder of control $Utx^{+/+}$ mice and the Utx mice at 4 weeks after BBN administration, extracted RNAs, and performed transcriptome analysis and pathway analysis by KEGG. As a result, the most enhanced pathway in the bladder epithelium of the $Utx^{\Delta/\Delta}$ mice was the "cytokine-cytokine receptor interaction" (FIG. 2A; thick frame), and additionally, enhancements of the "MAPK pathway" and "JAK-STAT pathway" were observed. These results indicate that UTX deletion activates cytokine pathways in the bladder epithelium, resulting in activation of intracellular signaling systems such as MAPK and JAK-STAT. Furthermore, the genes whose expressions were enhanced in the "cytokine-cytokine receptor interaction" pathway were looked into, and it was found that the most highly expressed was chemokine CCL2, and the next was the cytokine IL6 (FIG. 2B; bold letters).

Therefore, a model-based treatment experiment was conducted to investigate whether the progression of bladder cancer could be suppressed by suppressing the functions of these cytokine and chemokine. MBT2 is a bladder cancer tumor strain established from the mouse line C3H. We constructed a Utx-expressing strain (EV clones) and a Utx-deficient strain (KO clones) by introducing an empty vector (EV) and an Utx knockout (KO) vector into MBT2 (FIG.

3A). These clones were transplanted into syngeneic C3H mice and, after a 7-day engraftment period, the animals were subjected to treatment with vehicle only, propagermanium only (an inhibitor of CCL2-receptor CCR2, daily administration of the inhibitor mixed with feed at 0.005% concentration), MR16-1 only (a neutralizing antibody against mouse IL6 receptor, intraperitoneal injection at 100 μg per animal 3 times a week), and combined use of propagermanium and MR16-1 (Combination).

As a result, as shown in FIG. 3C, for the EV tumor resulting from transplantation of the Utx-expressing strain, any of the treatment methods did not show a significant therapeutic effect as compared to the vehicle alone; whereas, as shown in FIG. 3D, for the KO tumors resulting from transplantation of the Utx-deficient strain, combination therapy using propagermanium and MR16-1 (Combination) was found to significantly suppress tumor weight.

These results indicate that tumor growth can be significantly suppressed by suppressing both CCL2/CCR2 activity and IL6 activity in Utx-deficient bladder cancer.

As for articles showing the involvement of Utx in the onset of bladder cancer, there is a report of an experimental model of transplantation into immunodeficient mice using a human bladder cancer cell line carrying an Utx mutation (Deer Lee et al. Sci Trans. Med 2017); however, this is the result of performing xenotransplantation using cultured cells, and it is difficult to say that it is a model reflecting Utx function deficiency in vivo. So far, studies focusing on bladder cancer and performing production and analyses of bladder-specific Utx-deficient (Utx$^{\Delta/\Delta}$) mice using a genetic modification technique have not been reported, and studies and the techniques relating to the present invention can be considered original.

INDUSTRIAL APPLICABILITY

The present invention provides novel therapeutic agents for urologic cancers, particularly urologic cancers with reduced lysine (K)-specific demethylase 6A (KDM6A) function.

The invention claimed is:

1. A method for treating bladder cancer in a bladder of an individual, the method comprising administering to the individual an anti-IL-6 receptor antibody and propagermanium, wherein the individual's bladder cancer has one or more of: lysine (K)-specific demethylase 6A (KDM6A) func-
tion deficiency, inactivation of KDM6A, and absence of KDM6A protein expression.

2. The method of claim 1, wherein the individual is a human and the anti-IL-6 receptor antibody is a chimeric antibody, a humanized antibody, or a human antibody.

3. The method of claim 1, wherein cells of the bladder cancer comprise a mutated KDM6A gene.

4. The method of claim 3, wherein the mutated KDM6A gene comprises a loss-of-function mutation.

5. The method of claim 1, wherein the bladder cancer additionally has one or more of: p53 function deficiency, inactivation of p53, and no detectable p53 protein expression.

6. The method of claim 1, wherein cells of the bladder cancer comprise a p53 gene comprising a mutation.

7. The method of claim 1, wherein the method reduces growth of bladder cancer cells within a bladder, compared to growth of bladder cancer cells in a bladder in the absence of treatment.

8. The method of claim 1, further comprising determining that the individual's bladder cancer has one or more of: KDM6A function deficiency, inactivation of KDM6A, and absence of KDM6A protein expression.

9. A method for inhibiting growth of a bladder tumor in a bladder of an individual, the method comprising administering to the individual an anti-IL-6 receptor antibody and propagermanium, wherein the individual's bladder tumor has one or more of: KDM6A function deficiency, inactivation of KDM6A, and absence of KDM6A protein expression.

10. The method of claim 9, wherein the bladder tumor additionally has one or more of: p53 function deficiency, inactivation of p53, and no detectable p53 protein expression.

11. The method of claim 9, wherein cells of the bladder tumor comprise a p53 gene comprising a mutation.

12. The method of claim 9, wherein the method reduces growth of bladder cancer cells within a bladder, compared to growth of bladder cancer cells in a bladder in the absence of treatment.

13. The method of claim 9, further comprising determining that the individual's bladder cancer has one or more of: KDM6A function deficiency, inactivation of KDM6A, and absence of KDM6A protein expression.

* * * * *